United States Patent
Burgess et al.

(10) Patent No.: US 6,613,531 B2
(45) Date of Patent: Sep. 2, 2003

(54) SIGMA BINDING REGION OF RNA POLYMERASE AND USES THEREOF

(75) Inventors: Richard R. Burgess, Madison, WI (US); Terrance M. Arthur, Madison, WI (US); Larry C. Anthony, Madison, WI (US); Veit Bergendahl, Madison, WI (US); Bradley C. Pietz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/823,266

(22) Filed: Mar. 30, 2001

(65) Prior Publication Data

US 2002/0127688 A1 Sep. 12, 2002

Related U.S. Application Data

(60) Provisional application No. 60/193,116, filed on Mar. 30, 2000.

(51) Int. Cl.$^7$ .............................................. G01N 33/53
(52) U.S. Cl. ...................................................... 435/7.1
(58) Field of Search ......................................... 435/7.1

(56) References Cited

U.S. PATENT DOCUMENTS

| | | | | |
|---|---|---|---|---|
| 5,824,546 A | * | 10/1998 | Bishai et al. | 435/325 |
| 6,004,764 A | * | 12/1999 | Bishai et al. | 435/7.8 |
| 6,355,469 B1 | * | 3/2002 | Lam | 435/252.3 |

FOREIGN PATENT DOCUMENTS

| | | | | |
|---|---|---|---|---|
| CA | 2180077 | | 1/1997 | ........... C12N/15/31 |
| GB | G 2 298 862 A | * | 9/1996 | |
| GB | 2298862 | | 9/1996 | ........... C07K/14/35 |
| WO | WO-99/64866 | | 12/1999 | ......... G01N/33/569 |

OTHER PUBLICATIONS

Meghan M. Sharp et al, The interface of o with core RNA polymerase . . . , Aug. 24, 1999, pp. 3015–3026.*
Terrance Arthur and Richard Burgess, Localization of a o70 Binding Site . . . , Jul. 15, 1998, pp. 31381–31387.*
Arthur, T..M., et al., "Mutational Analysis of Beta 260–309, a o70 Binding Site Located on *Escherichia coli* Core RNA Polymerase", *J. Biol. Chem.*, 275, (2000),23113.
Burgess, Richard.R., et al., "How sigma docks to RNA polymerase and what sigma does", *Current Opinion in Microbiology*, (Mar., 2001), 11 pages.
Burgess, R..R., et al., "Interaction of *Escherichia culi* o70 with Core RNA Polymerase", *Cold Spring Harbor Symposium,* Cold Spring Harbor Press, NY, 63, (1998),277.
Burgess, R..R., et al., "Mapping Protein—Protein Interaction Domains Using Ordered Fragment Ladder Far–Western Analysis of Hexahistidine–Tagged Fusion Proteins", *Methods Enzymol.*, 328, (2000),141.
Burgess, R..R., "Purification of Overproduced *Escherichia coli* RNA Polymerase o Factors by Solubilizing Inclusion Bodies and Refolding from Sarkosyl", *Methods Enzymol.,* 273, (1996),145.
Dearruda, M.., et al., "pET–33b(+): A pET Vector that Contains a Protein Kinase A Recognition Sequence", *InNovations (Novagen Newsletter)*, 4A, (1996),7.
Harpur, Ailsa.G., et al., "Imaging FRET between spectrally similar GFP molecules in single cells", *Nat. Biotechnol., 19,* (2000),167.
Heyduk, E.., et al., "Architecture of a Complex between the o70 Subunit of *Escherichia coli* RNA Polymerase and the Nontemplate Strand Oligonucleotide", *J. Biol. Chem., 274,* (1999),3315.
Owens, J..T., et al., "Mapping the o70 subunit contact sites on *Escherichia coli* RNA polymerase with a o70–conjugated chemical protease", *Proc. Natl. Acad. Sci. U.S.A., 95,* (1998),6021.
Pollok, Brian.A., et al., "Using GFP in FRET–based applications", *Trends Cell Biol., 9,* (1999),57.
Severinov, K.., et al., "Assembly of functional *Escherichia coli* RNA polymerase containing Beta subunit fragments", *Proc. Natl. Acad. Sci. U.S.A., 92,* (1995),4591.
Severinov, K.., et al., "Dissection of the Beta Subunit in the *Escherichia coli* RNA Polymerase into Domains by Proteolytic Cleavage", *J. Biol. Chem., 267,* (1992),12813.
Severinov, K.., et al., "Structural Modules of the Large Subunits of RNA Polymerase", *J. Biol. Chem., 271,* (1996), 27969.
Severinov, K.., et al., "Tethering of the Large Subunits of *Escherichia coli* RNA Polymerase", *J. Biol. Chem., 272,* (1997),24137.
Thompson, N..E., et al., "Isolation and Characterization of a Polyol–Responsive Monoclonal Antibody Useful for Gentle Purification of *Escherichia coli* RNA Polymerase", *Biochemistry, 31,* (1992),7003.

* cited by examiner

*Primary Examiner*—Kenneth R. Horlick
(74) *Attorney, Agent, or Firm*—Schwegman, Lundberg, Woessner & Kluth, P.A.

(57) ABSTRACT

The invention provides a method to identify inhibitors of the formation of holoenzyme from core RNA polymerase and sigma.

30 Claims, 22 Drawing Sheets

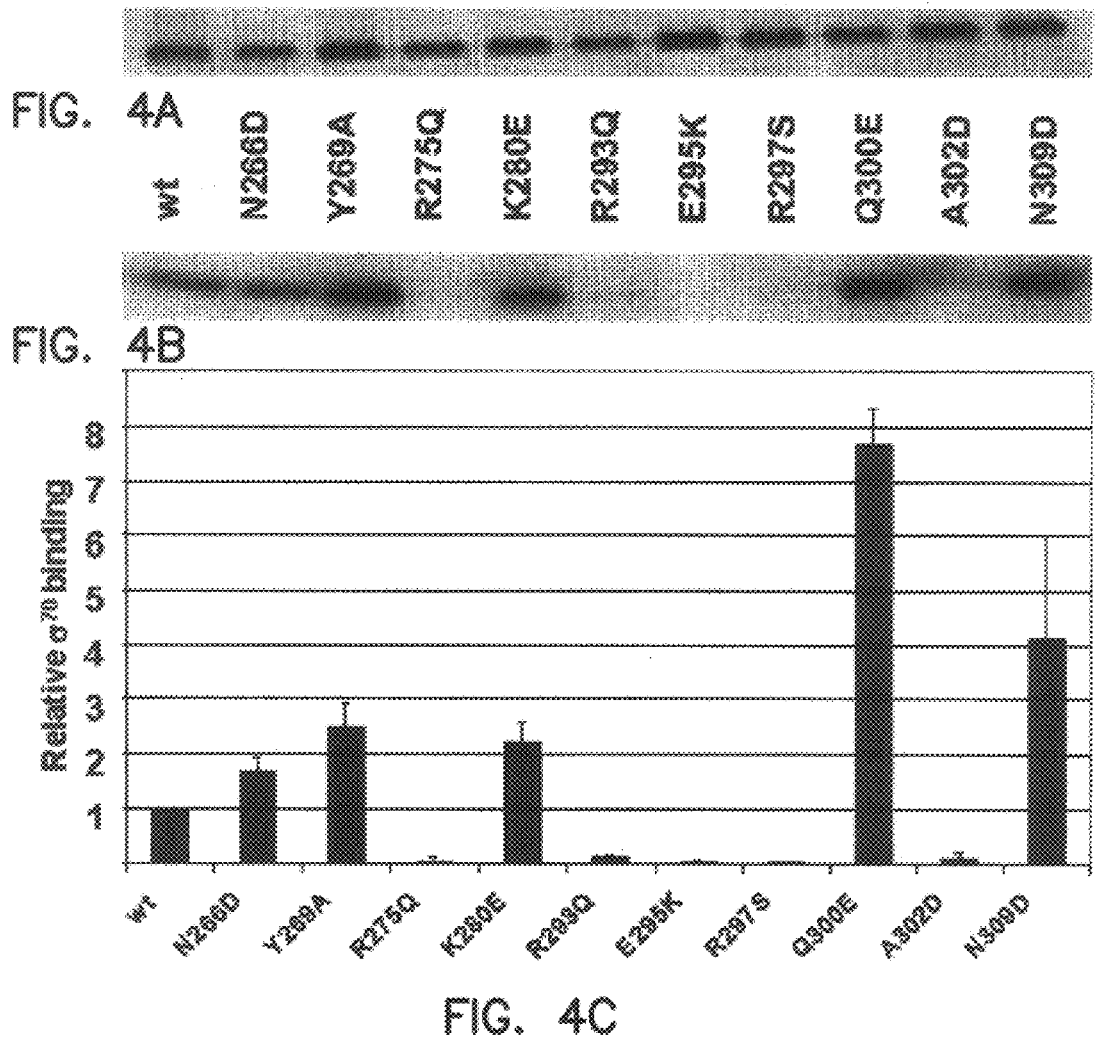

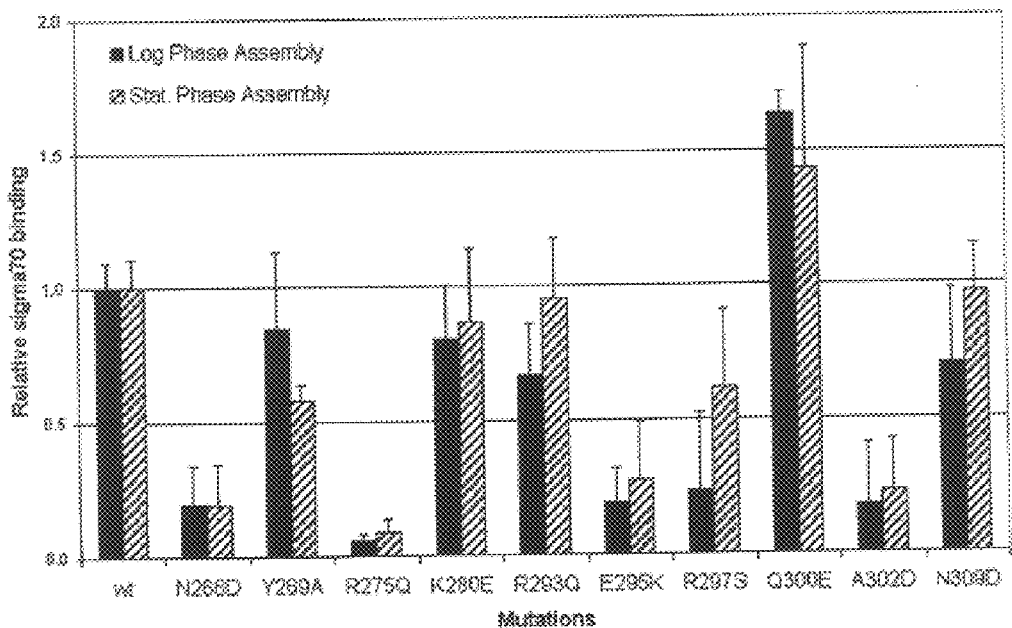
FIG. 6C
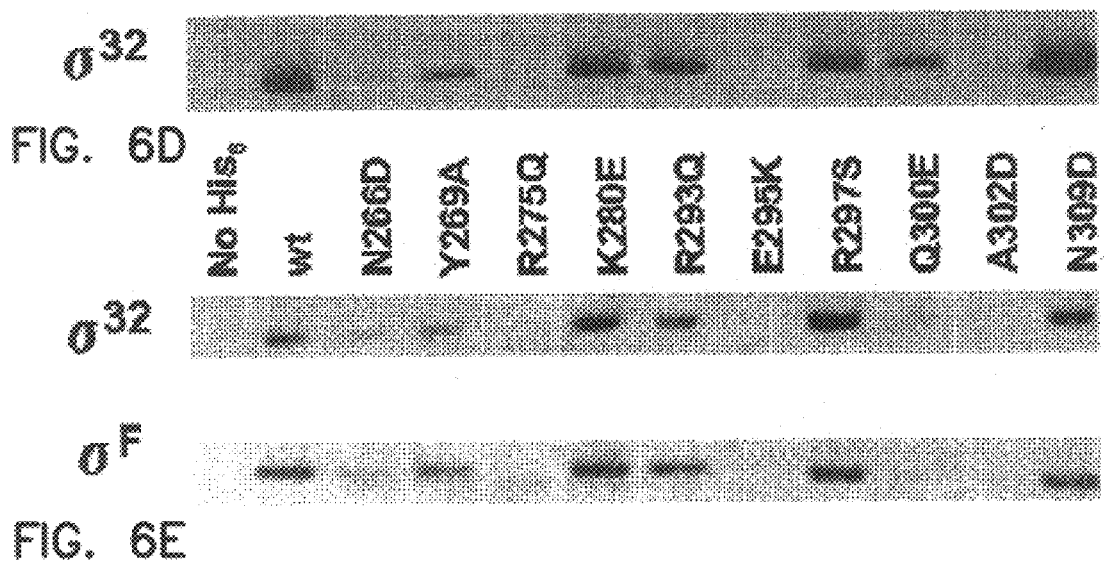
FIG. 6D
FIG. 6E

| PLASMID # | | ForWestern BINDING | GROWTH AT 42° C | ASSEMBLY E$\sigma^{70}$HOLO LOG PHASE | ASSEMBLY E$\sigma^{70}$HOLO STAT. PHASE |
|---|---|---|---|---|---|
| | WILD TYPE | 1.00 +/- 0 | + | 1.00 +/- 0.0 | 1.00 +/- 0.0 |
| TMA600 | N266D | 1.68 +/- 0.25 | +/- | 0.20 +/- 0.1 | 0.19 +/- 0.1 |
| TMA601 | Y269A | 2.49 +/- 0.45 | + | 0.84 +/- 0.3 | 0.58 +/- 0.0 |
| TMA602 | R275Q | 0.04 +/- 0.07 | - | 0.06 +/- 0.0 | 0.09 +/- 0.0 |
| TMA603 | K280E | 2.22 +/- 0.36 | + | 0.80 +/- 0.2 | 0.87 +/- 0.3 |
| TMA604 | R293Q | 0.11 +/- 0.05 | + | 0.67 +/- 0.2 | 0.95 +/- 0.2 |
| TMA605 | E295K | 0.03 +/- 0.03 | - | 0.19 +/- 0.1 | 0.27 +/- 0.2 |
| TMA606 | R297S | 0.02 +/- 0.03 | + | 0.24 +/- 0.3 | 0.62 +/- 0.3 |
| TMA607 | Q300E | 7.69 +/- 0.63 | + | 1.64 +/- 0.1 | 1.43 +/- 0.5 |
| TMA608 | A302D | 0.11 +/- 0.10 | - | 0.18 +/- 0.2 | 0.23 +/- 0.2 |
| TMA609 | N309D | 4.13 +/- 1.89 | + | 0.70 +/- 0.3 | 0.97 +/- 0.2 |

FIG. 7

```
                     260         270          280           290          300
E. c.             FATSDLNDLYRRVINRNNRLKRLLDLAAPDIIVRNEKRMLQEAVDALLDN(SEQ ID NO:)
T. a.             FATSDLNDLYRRNRNNRLKKLLAQQAPERNEKRMLQEAVDAMDN(SEQ ID NO:)
                     535         545          555           565          575
```

FIG. 8A

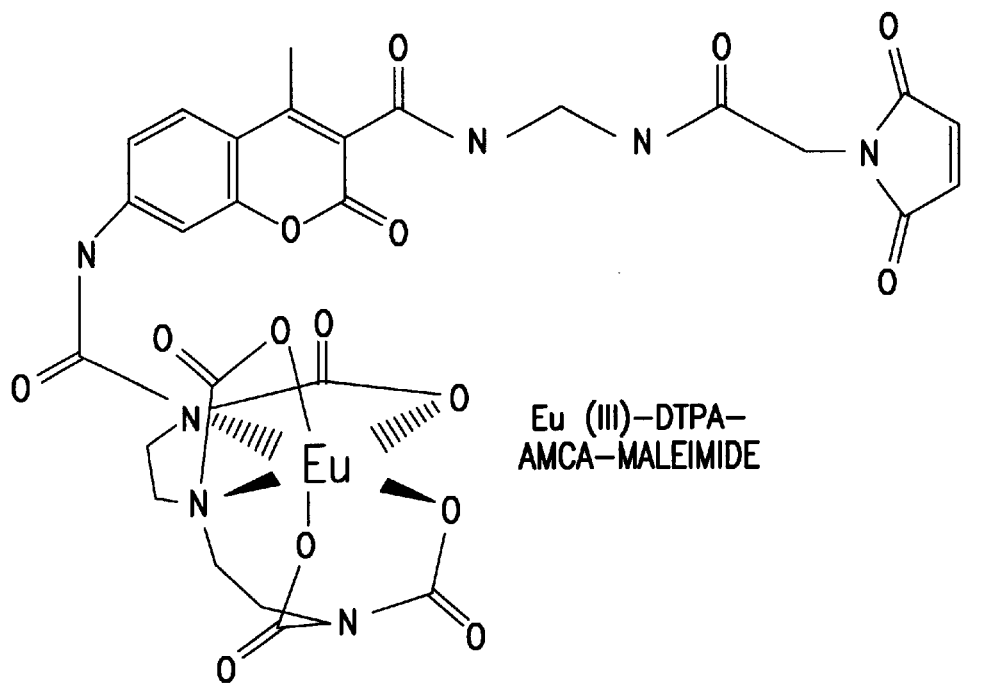
Eu (III)–DTPA–AMCA–MALEIMIDE
DIETHYLENE TRIAMINE PENTATEIC ACID–7–AMINO–4–METHYL–COUMARIN–3–ACETIC–ACID MALEIMIDE (Eu+3–CHELATE)
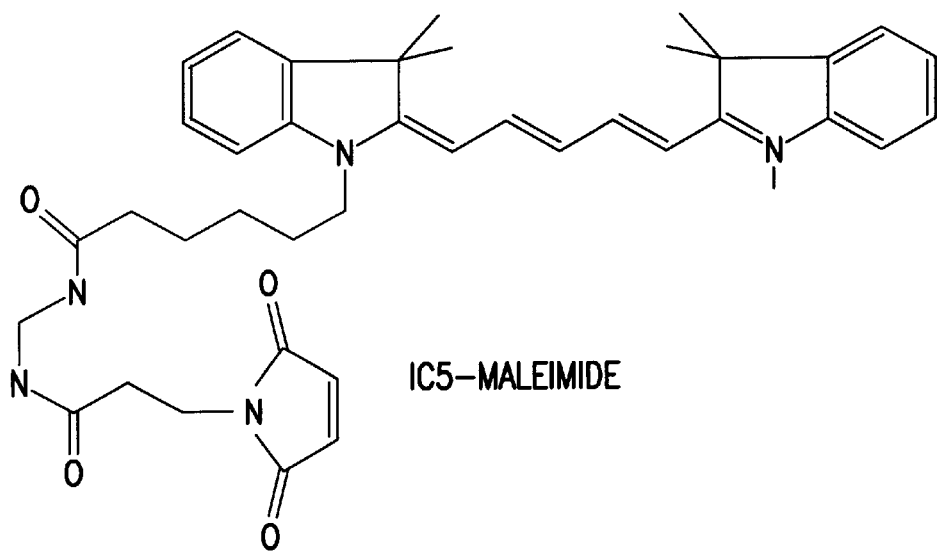
IC5–MALEIMIDE
5–N–N'–DIEHTYLTETRAMETHYLINDODICARBOCYANINE
FIG. 10

A *E.coli* σ70 schematic

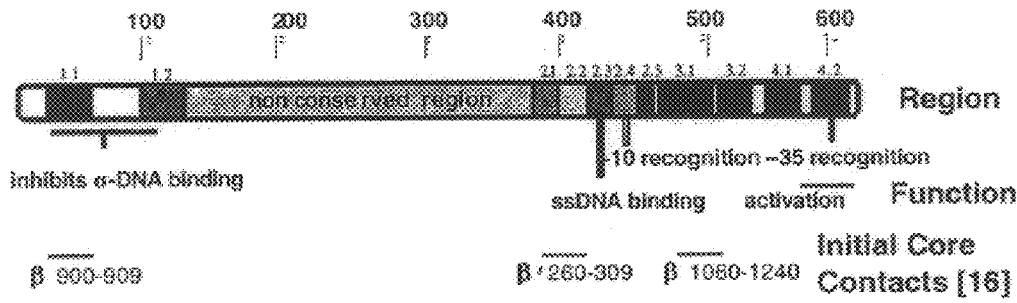

B σ70 region 2.1-2.2 homologs

```
                370       380       390       400       410
                 |         | x     x  |          | xx   xxx x|   x
E.coli           AKARRAKKEMVEANLRLVISIAKKYTNRGLQFLDLIQEGNIGLMKAV
C.crescentus     REARQAKKEMVEANLRLVISIAKKYTNRGLQFLDLIQEGNIGLMKAV
P.putida         AKARRAKKEMVEANLRLVISIAKKYTNRGLQFLDLIQEGNIGLMKAV
H.influenza      QKARRAKKEMVEANLRLVISIAKKYTNRGLQFLDLIQEGNIGLMKAV
M.xanthus        RRAERAKSELVEANLRLVVSIAKKYTNRGLQFLDLIQEGNIGLMKAV
S.aureus         QGDEVAKSRLAEANLRLVVSIAKRYVGRGMLFLDLIQEGNMGLIKAV
B.subtilis       EGDEESKRELAEANLRLVVSIAKRYVGRGMLFLDLIHEGNDGLMKAV
T.maritima       MGDKKAKEKLIESNLRLVVSIAKRYMGRGLSFQDLIQEGNIGLLKAV
                  :*   ;  ;*****;*****.* .**; *  ***;***;**;***
```

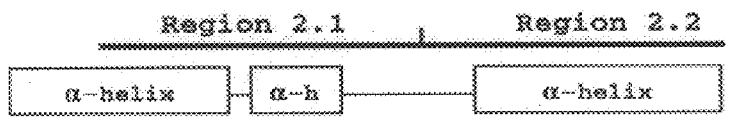

C *E.coli* σ's

```
                370       380       390       400       410
                 |         |          |          |          |
E.coli σ70      . AKARRAKKEMVEANLRLVISIAKKYTNRGLQFLDLIQEGNIGLMKAV
E.coli σS       ----VASRRRMIESNLRLVVKIAKRYGNRGLALLDLIEBGNLCLIRAV
E.coli σ32      ----LEAAKTLILSHLRFVVHIARNYAGYGLPQADLIQEGNIGLMKAV
E.coli σF       -----YVPLVRHEA-LRLQVRLP-----ASVELDDLLQAGGIGLLNAV
                     :  **;  ; :.    .:  : **::  **.;.;**;.**
```

D β'260-309 homologs

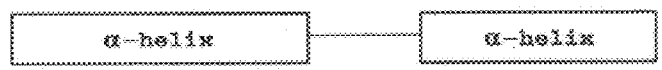

```
                260       270       280       290       300
                 |         | x         |          | x x x |   x
E.coli           FATSDLNDLYRRVINRNNRLKRLLDLAAPDIIVRNEKRMLQEAVDALLDN
T.aquaticus      FATSDLNDLYRRLINRNNRLKKLLAQGAPEIIRNEKRMLQEAVDAVIDN
P.putida         FATSDLNDLYRRVINRNNRLKRQLDLSAPDIIVRNEKPMLQRAVEPLLDN
H.influenza      FATSDLNDLYRRVINRNNRLKRLLDLIAPDIIVRNEKRMLQESVDALLDN
S.aureus         FATSDLNDLYRRVINRNNRLKRLLDLGAPGIIVQNEKRMLQEAVDALIDN
B.subtilis       FATSDLNDLYRRVINRNNRLKRLLDLGAPSIIVQNEKRMLQEAVDALIDN
T.maritima       FATTDLNELYRRLINRNNRLKKLLELGAPEIILRNEKRMLQEAVDALIHN
                 ***;***,****;*********;  *;;  **  **;;*** ****;*;:*;;.*
```

FIG. 20

SIGMA BINDING REGION OF RNA POLYMERASE AND USES THEREOF

CROSS-REFERENCE TO RELATED APPLICATIONS

This application claims the benefit of the filing date of U.S. application Ser. No. 60/193,116 filed Mar. 30, 2000, under 35 U.S.C. §119(e).

STATEMENT OF GOVERNMENT RIGHTS

This invention was made, at least in part, with a grant from the Government of the United States of America (grant GM 28575 from the National Institutes of Health). The Government may have certain rights to the invention.

BACKGROUND OF THE INVENTION

The RNA polymerase of *Escherichia coli* is a large, multisubunit enzyme existing in two forms. The core enzyme, consisting of subunits β and β' and an α subunit dimer, carries out processive transcription elongation followed by termination (Helmann et al., 1988). When one of a variety of sigma (σ) factors is added to core, the holoenzyme is formed (Burgess et al., 1969). The σ subunit confers promoter-specific DNA binding and transcription initiation capabilities to the enzyme (Helmann et al., 1988; Burgess et al., 1969; Gross et al., 1996; Gross et al., 1992). $\sigma^{70}$ of *E. coli* was the first a factor to be described and characterized (Burgess et al., 1969). Since then, numerous a factors have been discovered throughout the Eubacterial kingdom, including six alternative a factors in *E. coli*. Each σ subunit directs its cognate holoenzyme to start transcription from only those promoters containing DNA sequences specifically recognized by the σ factor. Thus, generally, each a directs transcription initiation from a specific set of promoters to transcribe genes with related functions. This control of transcription is mediated partially through the competition of the individual σ factors for the core enzyme and is a major part of global gene regulation in bacteria (Zhou et al., 1992).

As the number of identified σ factors increased, it became apparent that they shared several regions of amino acid sequence similarity (Helmann et al., 1988; Gribskov et al., 1986; Lonetto et al., 1992), and the function of the conserved regions is of continuing interest (Waldburger et al., 1994; Dombrowski et al., 1993; Siegele et al., 1989; Gardella et al., 1989; Lesley et al., 1989). Deletion analysis of $\sigma^{70}$ identified a segment of the protein that overlaps conserved region 2.1 (residues 361–390) as being necessary and sufficient for core binding (Lesley et al., 1989). A mutation in a homologous region of *Bacillus subtilis* $\sigma^E$ has also been shown to affect core binding (Shuler et al., 1995). However, recent findings of core binding mutations in other conserved and nonconserved regions of $\sigma^{32}$ have led to the idea of multiple binding sites for the σ subunit on the core enzyme (Joo et al., 1997; Zhou et al., 1992; Joo et al., 1998; Sharp et al., 1999).

The β and β' subunits each contain regions that have high sequence homology with the two largest subunits of eukaryal polymerases (Allison et al., 1985; Sweetser et al., 1987; Jokerst et al., 1989). Some of these conserved regions may act as interaction domains. An interaction domain is the minimal region of a protein that can independently fold to form the secondary and tertiary structure required to interact with another protein, DNA, RNA, or ligand. Interaction domains are larger than the actual binding site which is formed by the amino acids in direct contact with the binding partner. Severinov et al. (Severinov et al., 1992, 1995 and 1996) demonstrated the domain-like properties of β and β' by reconstitution of functional RNA polymerase from fragmented β and β' subunits. Thus, the properties of the polymerase do not require the entire intact length of the subunit but rather can be generated with smaller domain modules.

There have been two observations that have identified deletions in the β or β' subunits that produce subunits still capable of forming core enzyme structures but not the holoenzyme. First, a β subunit truncation, missing approximately 200 amino acids of the C terminus, was shown by glycerol gradient centrifugation to migrate with the other core subunits but was never seen in the σ-containing fractions (Glass et al., 1986). Second, when immunoprecipitation assays were performed using reconstituted RNA polymerase containing β' deletion mutants missing amino acids 201–477, the core subunits were recovered in the same fraction but lacked σ (Luo et al., 1996). However, it was unclear whether the β' deletion was non-specific, e.g., prevented correct formation of the interaction domain.

The idea that σ binding is affected by perturbations of the C terminus of β and the N terminus of β' is consistent with experiments showing that these two subunit termini are physically close together and can be fused through a flexible linker and still form a functional enzyme (Severinov et al., 1997). Recent protein-protein footprinting data have identified a similar region on β' and two new sites on β for possible interactions with the $\sigma^{70}$ subunit (Owens et al., 1998). While Owens et al. showed that residues 228–461 of β' are physically close to σ, the authors did not conclude that there is a direct interaction between β' and σ.

Burgess et al. (1998) report that residues 260 to 309 of β' bind to a based on the use of in vitro far-Western and co-immobilization assays. However, in vitro cell-free binding results do not evidence that the region involved in binding in vitro is involved in binding in vivo. For example, it is possible that this region of β' is buried in the native structure, e.g., a hydrophobic region, and so would not play a role in vivo binding. Structural analysis programs indicate that $\beta'_{260-309}$ has two α helices joined by a random coil, and that these two helices are amphipathic and have the potential for coiled coil formation, based on a heptad repeat motif (Chao et al., 1998; Cohen et al., 1986; Lupas et al., 1991). In particular certain positions known as a and d in the coiled coil motif are hydrophobic and so may be buried in native β'

Thus, what is needed is the identification of a region in the subunits of core RNA polymerase that interacts with σ in vivo. What is also needed is a method to identify specific inhibitors of the binding of σ to core RNA polymerase.

SUMMARY OF THE INVENTION

The invention provides an isolated and purified β' subunit of RNA polymerase or a portion (i.e., fragment) thereof which specifically binds to σ in vivo. Preferably, the portion comprises at least 39, more preferably at least 44, and even more preferably at least 49, residues of the β' subunit, although smaller fragments which specifically bind to σ in vivo are also envisioned. Also preferably, the isolated and purified portion of the β' subunit comprises residues 270 to 309, and even more preferably residues 260 to 309. As described hereinbelow, a region on the β' subunit of RNA polymerase was identified that interacts directly with σ (the interaction domain). The in vitro interaction domain of the β' subunit with σ was identified by far-Western blot analysis, which is a general method for mapping a domain on one protein that is necessary for binding another protein, and a co-immobilization assay. As used herein, an "interaction domain" refers to the minimal region of a protein that can independently fold to form the secondary and tertiary structures required to interact with another protein, DNA, RNA or ligand. The σ binding region of β' was found to interact with various a factors, including $\sigma^{70}$ and several other E. coli σ's, T4 phage σ gp 55, and $\sigma^A$ from Bacillus subtilis.

As also described hereinbelow, proteins were prepared which had single point mutations in the predicted coiled coils located within residues 260–309 of β'. Several of the mutants were defective for binding $\sigma^{70}$ in vitro. Of these mutants, three (R275Q, E295K, and A302D which are change-of-charge mutants at the e and g residues of the $\beta'_{260-309}$ predicted coiled coil) were completely defective for growth in an in vivo assay where the mutant β' is the sole source of β' subunit. All of the mutants were able to assemble into the core enzyme, however, R275Q, E295K, and A302D were defective for $E\sigma^{70}$-holoenzyme formation. Several of the mutants were also defective for holoenzyme assembly with various minor σ factors. Some mutations were nonfunctional in some of the assays but functional in others, indicating that binding of other sites may compensate for loss of binding at the $\beta'_{260-309}$ site. Thus, these results showed that residues 260 to 309 of the β' subunit specifically bind to σ in vivo, and that mutations in this region can greatly diminish core binding of $\sigma^{70}$ and other minor σ's. In the recently published crystal structure of Thermus aquaticus core RNA polymerase (Zhang et al., 1999), the region homologous to $\beta'_{260-309}$ of E. coli forms a coiled coil. Modeling of the β' mutations described herein onto that coiled coil places the most defective mutations on one face of the helix, which may indicate where most of the contact surface with $\sigma^{70}$ occurs. As RNA polymerase is a large multi-subunit complex (having about 3300 amino acids), and the β' subunit of RNA polymerase is a large protein, e.g., the β' subunit of E. coli is about 155,000 daltons, the identification of the region of the core RNA polymerase which specifically interacts with σ in vivo represents a significant finding as it provides a specific target for drug discovery, e.g., drugs which specifically interfere with the core-σ interaction.

Thus, the invention provides a method to identify an agent which inhibits or prevents the binding of σ to core RNA polymerase, a subunit thereof or a portion of the subunit. The method comprises contacting the agent with core RNA polymerase, e.g., isolated core RNA polymerase, or an isolated subunit of RNA polymerase or a portion thereof so as to form a complex. As used herein, "isolated and/or purified" refers to in vitro preparation, isolation and/or purification of a protein or a complex of biomolecules, e.g., core RNA polymerase, so that it is not associated with in vivo substances or is substantially purified from in vitro substances. Preferably, the portion of the subunit comprises at least 39 amino acids, more preferably at least 44 amino acids, even more preferably at least 49 amino acids, of the β' subunit. The complex is then contacted with σ or a portion thereof and it is determined whether the agent inhibits or prevents the binding of σ to core RNA polymerase, the isolated subunit of RNA polymerase or portion thereof. A portion of a comprises at least 30, preferably at least 55, more preferably at least 100, and even more preferably at least 140 residues of σ, although smaller fragments which specifically bind to β' in vivo are also envisioned. Alternatively, the agent is contacted with the core RNA polymerase, a subunit and or portion thereof and σ or a portion thereof, i.e., simultaneously. The σ may be a homologous σ, for example, if the core RNA polymerase or the isolated subunit of RNA polymerase is that of E. coli, the σ is a σ which is encoded by the genome of E. coli. Alternatively, the σ may be a heterologous σ, e.g., a phage-encoded σ.

Further provided is a method which comprises contacting the agent with isolated σ or a portion thereof so as to form a complex. The complex is then contacted with isolated core RNA polymerase, or an isolated subunit of RNA polymerase or a portion thereof and it is determined whether the agent inhibits or prevents the binding of σ to core RNA polymerase, the isolated subunit of RNA polymerase or portion thereof.

To find new inhibitors of bacterial transcription, a homogenous luminescence resonance energy transfer (LRET) based assay was developed on the basis of the fluorescent-labeled proteins $\sigma^{70}$ and β'-fragment (residues 100–309). For the assay, $\sigma^{70}$ was labeled with a europium chelate (Eu(III)-DTPA-AMCA-maleimide) as the LRET donor and β' was labeled with IC5-maleimide as the acceptor. Measuring time-resolved fluorescence with the labeled proteins permitted the monitoring of binding of $\sigma^{70}$ to β' by observing the emission of the LRET acceptor (IC5-labeled β'-fragment). The emission of the acceptor is sensitized by an energy transfer from the LRET donor (DTPA-AMCA-Eu-complex-labeled $\sigma^{70}$) that occurs when the dyes come into close proximity to each other (<75 Å). Due to its naturally short lifetime of several nanoseconds, the residual IC5-fluorescence acquired after 50 microseconds is due solely to LRET, reducing the background signal to a minimum and hence providing a good signal-to-noise ratio. The assay was used to measure the effect of the environment (solvents, denaturants, and salt) and can be used to measure the effect of potential inhibitors on the binding of $\sigma^{70}$ to the β'-fragment. Such an assay is particularly well suited for high-throughput screening.

Also provided is a method to identify a region on a subunit of core RNA polymerase which specifically binds σ. The method comprises contacting core RNA polymerase, e.g., isolated core RNA polymerase, an isolated subunit thereof or a portion thereof with σ or a portion thereof so as to form a complex. The core RNA polymerase, isolated subunit or portion thereof comprises at least one amino acid substitution. Then complex formation is detected or determined and, for example, compared to complex formation between core RNA polymerase, an isolated subunit or portion thereof, which does not comprise an amino acid substitution, and σ or a portion thereof.

The invention further provides a method to identify an agent which inhibits or prevents the binding of σ to the β' subunit of core RNA polymerase. The method comprises contacting a prokaryotic cell with the agent and detecting or determining whether the agent inhibits or prevents the binding of σ to the β' subunit of RNA polymerase in the cell. The cell may be a recombinant cell, i.e., a cell which is augmented by exogenously introduced nucleic acid, e.g., by transformation or transduction. Thus, the invention also provides a host cell comprising a recombinant DNA encoding a β' subunit of RNA polymerase.

The invention further provides agents identified by the methods of the invention and, in particular, agents which inhibit the growth of prokaryotic cells which are associated with disease, see e.g., Zinsser Microbiology (17th ed., Appleton-Century-Crofts, NY (1980).

BRIEF DESCRIPTION OF THE FIGURES

FIG. 4. Western and far-Western blots of cell extracts containing wild type or mutant β'$_{1-319}$. Cell extracts were analyzed by 8–16% Tris-glycine SDS-PAGE, blotted to nitrocellulose, and probed with (A) anti-β' antibody, or (B) $^{32}$P-labeled σ$^{70}$. (C) Relative binding of σ$^{70}$ by wild type and mutant β' fragments. The values for relative σ$^{70}$ binding by wild type versus mutant β'$_{1-319}$ fragments as determined from far Western blotting analysis were normalized to the amount of β'$_{1-319}$ fragment loaded as determined by quantitative Western blot analysis (wild type=1.0). Error bars represent standard deviation. Results are the average of three different experiments.

FIG. 6C. Quantitation of relative σ$^{70}$ binding for the mutants versus wild type β', normalized to the amount of the α subunit retained (wild type=1.0). Results are the average of three different experiments. Error bars represent standard deviation.

FIG. 6D. Log phase samples probed for minor σ factors.

FIG. 6E. Stationary phase samples probed for minor σ factors.

FIG. 7. Summary of data for mutants.

FIG. 8A. Protein sequence alignment of E. coli β'$_{260-309}$ and the homologous region from T. aquaticus. Shaded letters represent those not identical to E. coli.

FIG. 10. Dyes used to derivatize the proteins and serve as the fluorophores in the LRET assay.

FIG. 20. A) Schematic of structural and functional regions of E. coli σ$^{70}$. B) Sequence alignment of σ$^{70}$ region 2.1–2.2 homologs. C) Sequence alignment of E. coli σ's. D) Sequence alignment of β' 260–309 from various organisms.

DETAILED DESCRIPTION OF THE INVENTION

Bacterial RNA polymerase synthesizes RNA from cellular genes and thus plays a central role in the regulation of gene expression. Core RNA polymerase can synthesize RNA but is unable to specifically bind DNA at promoter sites. To specifically bind DNA and initiate transcription of genes, σ binds to core to form the holoenzyme. A drug which prevents σ binding to core polymerase would prevent cell growth. In vitro methods (Example 2 and Burgess et al., 1998) identified a 49 amino acid region of the β' subunit of core polymerase which is important for σ binding and which is highly conserved in bacterial polymerases. However, to establish that this region is important for σ binding in vivo, mutational studies were necessary (Example 3). Once the region in core RNA polymerase which binds to σ in vivo is identified, the identification of broad-range antibiotics, e.g., small molecules such as peptides or other molecules, which specifically interfere with the binding is greatly facilitated.

The invention will be further described by the following non-limiting examples.

EXAMPLE 1

Far-Western Blot Mapping

Transferring materials out of SDS gels (blotting) onto a nitrocellulose membrane has become a widely used technique. It not only takes advantage of the high resolving power of polyacrylamide gel electrophoresis but also allows ready access to the blotted target material by a variety of interaction probes. A Western blot is generally probed or detected with an antibody, while a south-Western blot is probed with a labeled DNA. In a far-Western blot, instead of probing with an antibody, one probes with another protein, taking advantage of specific protein-protein interactions. This approach requires that at least some region (the interaction domain) of a fraction of the blotted target protein be able to refold on the membrane and form a 3-dimensional structure containing the interaction site. This approach is particularly useful in determining which subunit of a multisubunit complex is involved in an interaction with the probe protein.

Figure 1:
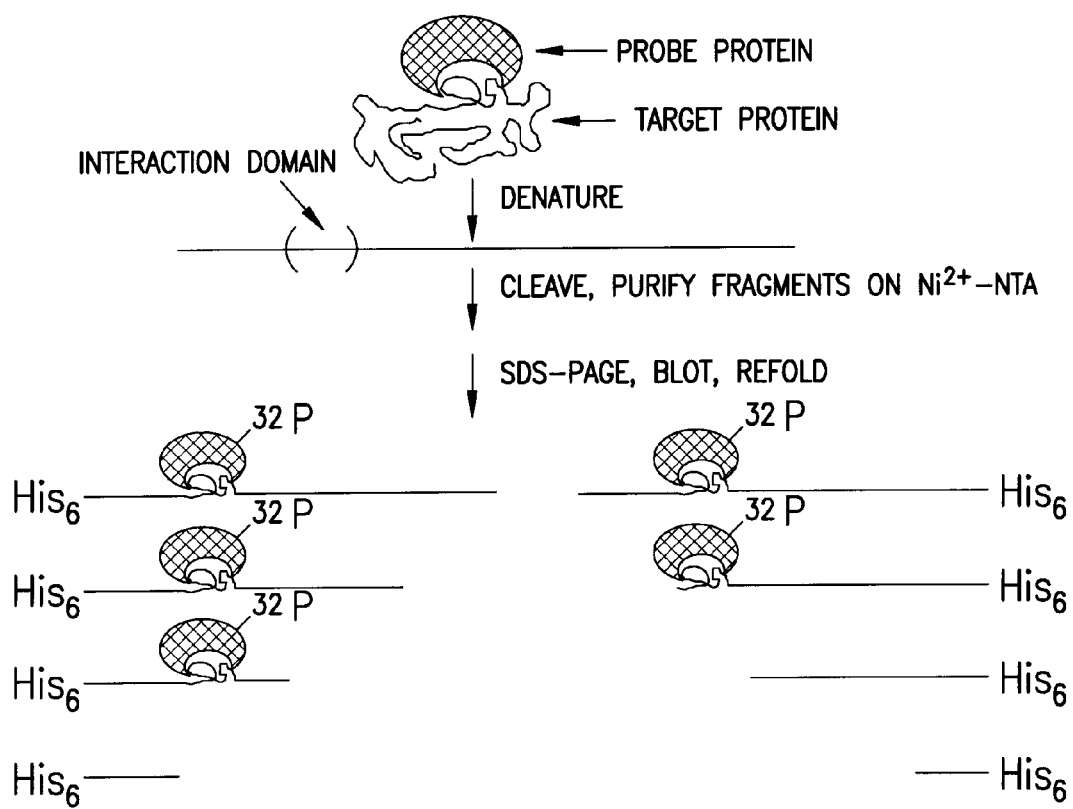
FIG. 1. A schematic of the ordered fragment ladder far-Western method. His$_6$-tagged target protein is cleaved, and the fragments are purified on a Ni$^{2+}$-NTA column, fractionated on SDS-PAGE, and electroblotted onto nitrocellulose. The denaturant is washed away from the blotted protein fragments, and the interaction domains on fragments are allowed to refold. The interaction domains can be identified by probing with a radioactively-labeled protein. The interaction domain is mapped by identifying fragments that have part of their interaction domain missing and can no longer bind the probe.

The use of an ordered fragment ladder far-Western analysis takes advantage of the ease of constructing hybrid proteins containing a tag, for example, a hexahistidine tag (His$_6$-tags), at either terminus. His$_6$-tagged proteins bind to Ni-chelate columns, even in the presence of denaturants. This method is potentially applicable to any protein-protein interaction study. A schematic that illustrates the principle of this method using a His$_6$-tag is shown in FIG. 1.

Ordered fragment ladder far-Western analysis includes:

A. cloning and purification of a protein of interest with a His$_6$-tag fused to either the N-terminus or C-terminus of that protein;

B. chemical or enzymatic partial cleavage of the His6-tagged protein to create a series of fragments;

C. purification of His$_6$-tagged fragments on a Ni-chelate affinity column under denaturing conditions to obtain a set of fragments all containing the His$_6$-tagged end;

D. fractionating these fragments on the basis of size by SDS-polyacrylamide gel electrophoresis to form an ordered fragment ladder;

E. transferring the protein fragments out of the gel and onto a nitrocellulose membrane and allowing these protein fragments to refold on the membrane;

F. preparing a $^{32}$P-labeled protein probe, e.g., by labeling a heart muscle protein kinase (HMK) recognition site-tagged protein with γ$^{32}$P-ATP and heart muscle protein kinase;

G. probing the membrane with the labeled probe, washing and detection; and

H. validating and characterizing the far-Western complex.

A. Cloning and Purification of Protein with a $His_6$-tag

Standard cloning methods are used to place the gene of interest into an overproducing vector that results in the addition of a $His_6$-tag on either the—or C-terminus of the protein. A variety of such vectors are available, e.g., pET vectors (Studier et al., 1990) are a T7 polymerase-based expression system available from Novagen (Madison, Wis.). The appropriate overexpression strain is induced with isopropyl-β-D-thiogalactopyranoside (IPTG), the cells lysed, and inclusion bodies prepared (Arthur and Burgess, 1998). The resuspended inclusion bodies are aliquoted into 1 mg portions and frozen at −70° C. until use.

B. Chemical and Enzymatic Cleavage of Proteins

Figure 2:
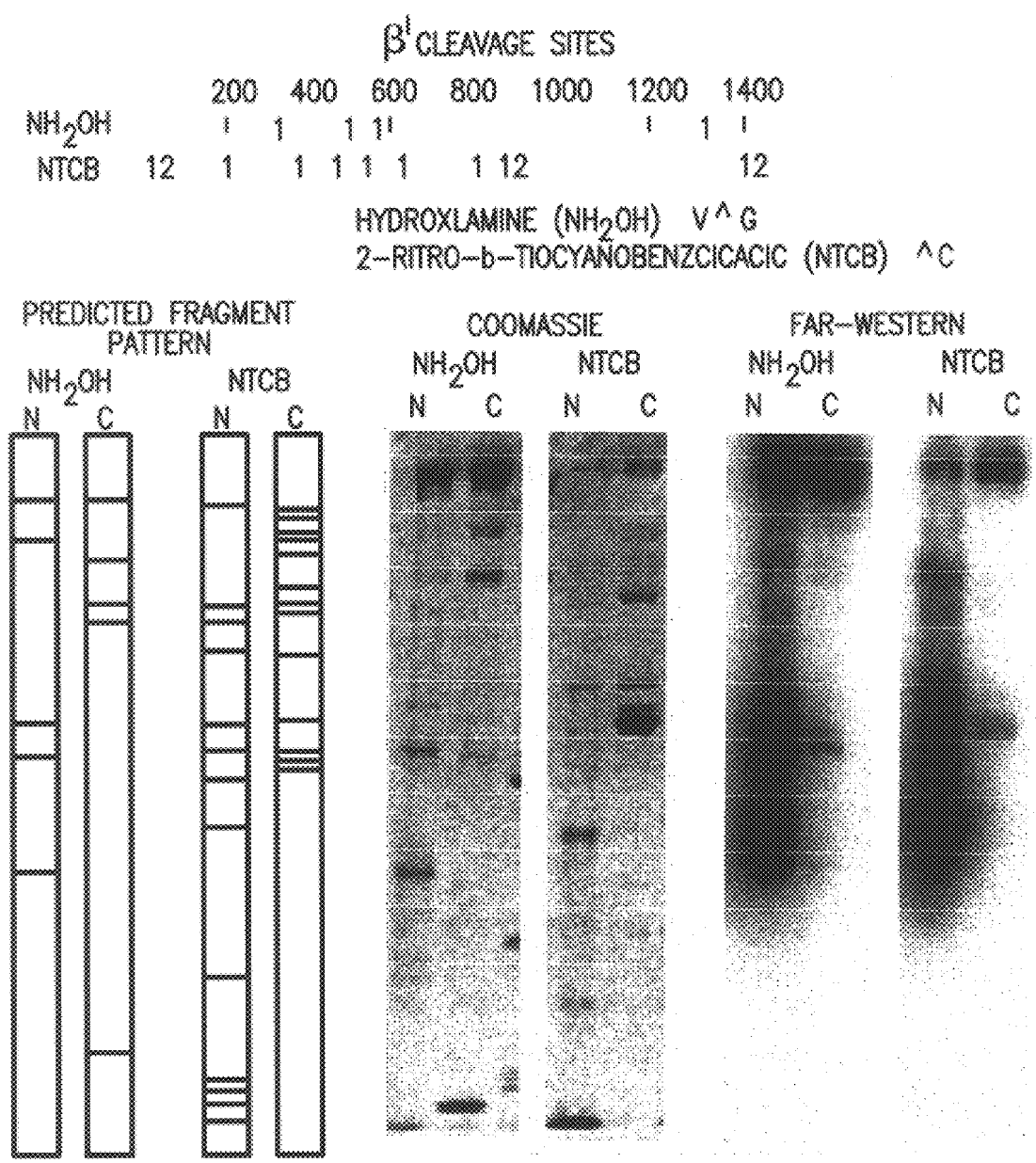
FIG. 2. Example of an ordered fragment ladder far-Western analysis. A) A schematic indicating the position of the chemical cleavage sites on the E. coli RNA polymerase β' subunit for chemical cleavage agents hydroxylamine (NH$_2$OH, "Hyd") and 2-nitro-5-thiocyanobenzoic acid (NTCB). These cleavage sites were predicted from the amino acid sequence using the MacVector program (Oxford Molecular Group). The numbers refer to the amino acid positions from the N-terminus at the left. A "1" indicates the position of a cleavage site, while a "2" indicates two sites very close together. B) The ordered fragment ladder of—and C-terminal His$_6$-tagged β' subunit cleaved with NH$_2$OH or NTCB. On the left is shown a schematic of the expected bands on a SDS gel. In the middle is the actual coomassie-stained gel, and on the right is an identical gel blotted onto nitrocellulose and probed with $^{32}$P-labeled σ$^{70}$. It can be seen from the NH$_2$OH cleavage fragment results that most of the N-terminal His$_6$-tagged fragments bind the probe, while only the full-length C-terminal His$_6$-tagged protein binds the probe. Thus, the interaction domain is within the region from amino acid 1 to 309 of β'.

To predict the chemical and enzymatic cleavage sites of an overproduced, $His_6$-tagged target protein, the amino acid sequence of a target protein can be entered into a computer program that predicts protein cleavage sites (e.g., there are such programs as part of the MacVector or DNA STAR packages). Based on the predicted pattern of cleavage, one or more cleavage protocols are selected. An example of the predicted cleavage sites for *Escherichia coli* RNA polymerase β' subunit for two chemical cleavage agents is shown in FIG. 2A.

Cleavage Protocols

The conditions described below are exemplary and can be varied, by varying the time of cleavage or the amount of the cleavage reagent, to accommodate proteins that are particularly easy or difficult to cleave. Preferably, cleavage conditions are employed which result in as even as possible a distribution of fragments. This often is a reaction that leaves 10–30% of the polypeptide uncleaved.

Iodosobenzoic Acid Cleavage (Fontana et al., 1983) (cleaves after Trp)

1) Dissolve 1 mg protein in 200 µl 8 M GuHCl.
2) Add 800 µl 100% acetic acid, 3 µl p-cresol, and 2 mg iodosobenzoic acid (IBA; Sigma Cat. # I=8000).
3) Incubate at room temperature for 20 hours.
4) Speed Vac to dryness (about 1 hour).
5) Resuspend in 1 ml urea buffer (Buffer B+8 M urea; Buffer B is 20 mM Tris-HCl, pH 7.9; 500 mM NaCl; 5 mM imidazole (Fisher Catalog # BP305-50); 0.1% (v/v) Tween 20; and 10% (v/v) glycerol).
6) Load on Ni-column.

2-nitro-5-thiocyanobenzoic acid (NTCB) Cleavage (Jacobson et al., 1973) (cleaves before Cys)

1) Dissolve 1 mg protein in 1 ml urea buffer without glycerol.
2) Add 5-fold molar excess (to Cys in protein) of dithiothreitol (DTT) made fresh (1 M stock).
3) Incubate 15 minutes at 37° C. to reduce disulfides.
4) Add 5-molar excess (over total Cys) NTCB (Sigma Cat. # N-7009) and adjust pH to 9.5 with NaOH.
5) Incubate at room temperature for 2–6 hours for partial cleavage or 24–30 hours for total cleavage.
6) Dilute 1:10 in urea buffer and load on Ni-column.

Hydroxylamine Cleavage (Bornstein and Bolian 1970) (cleaves between Asn-Gly)

1) Dissolve 1 mg protein in 1 ml urea buffer.
2) Incubate 15 minutes at 37° C.
3) To 500 µl of urea-solubilized protein, add 500 µl of hydroxylamine buffer (400 mM CHES buffer pH 9.5; 4 M hydroxylamine-hydrochloride (Aldrich Cat. No. 15,941-7); and adjust pH to 9.5 with 10 M NaOH) and incubate 2 hours at 42° C.
4) Add 7 µl 2-mercaptoethanol (to 0.1 M), mix, and incubate for 15 minutes at 37° C.
5) Dilute 1:10 in urea buffer and load on Ni-column.

Thermolysin Cleavage (Rao et al., 1996) (cleaves before hydrophobic amino acids)

1) Resuspend 1 mg of inclusion body protein in 100 µl of urea buffer.
2) Incubate for 15 minutes at 37° C.
3) Add thermolysin (from *Bacillus thennoproteolyticus*, Boehringer Mannheim) at protein:protease ratios of 4,000:1, 8,000:1 and 16,000:1 (w/w).
4) Digest for 30 minutes at room temperature.
5) Load on Ni-column.

Trypsin Cleavage (Rao et al., 1996) (cleaves after Arg and Lys)

1) Resuspend 1 mg of inclusion body protein in 1 ml of urea buffer.
2) Incubate for 15 minutes at 37° C.
3) Dilute to 4 M urea by adding an equal volume of buffer B.
4) Add trypsin (TPCK treated, Worthington Biochemicals) at protein:protease ratios of 4,000:1, 8,000:1 and 16,000:1 (w/w).
5) Digest for 30 minutes at room temperature.
6) Load on Ni-column.

Chemical cleavage ladders are very useful in determining the precise size of fragments since one knows exactly where the cleavage occurs. This is particularly important since many proteins migrate abnormally upon SDS polyacrylamide gel electrophoresis.

Since most chemical cleavage reagents only produce a few cuts per polypeptide chain, the ordered fragment ladder generated by chemical cleavage has only a few "rungs" on the ladder. Therefore, partial cleavage with one or more proteases can be used to create a ladder with more rungs that is capable of higher resolution mapping of interaction domains. Light, moderate, and heavy cleavage reactions can be performed with a given protease, and the resulting cleavage reactions mixed together before or after purification on the Ni-chelate column. This helps to produce a ladder containing similar amounts of each fragment size.

Sometimes it is difficult to generate a good ladder by partial cleavage methods, either because of a scarcity or uneven distribution of chemical cleavage sites or because the protein is relatively resistant to proteolysis. In these cases one can also produce ladders by cloning individual truncated fragments.

C. Ni-Chelate Column Purification of His6-tag Fragments

Procedure

1) Load $Ni^{2+}$-NTA resin ($Ni^{2+}$-NTA agarose, Qiagen) slurry into BioRad mini column to generate a 300 µl column bed.
2) Wash with 5 column volumes of MilliQ water. All column operations are carried out at room temperature.
3) Wash with 5 column volumes of urea buffer.
4) Load cleavage reaction (see above) and let drain to top of resin.
5) Wash with 10 column volumes of urea buffer to remove non-His-tagged fragments.
6) Wash with 10 column volumes of buffer B to remove urea.
7) Elute with 500 µl buffer B with 200 mM imidazole.
8) Check extent of cleavage by SDS-PAGE.
9) Store fragments as 50 µl aliquots frozen at −20° C.

The use of Ni-chelate column purification permits His-tagged proteins or fragments to bind to $Ni^{2+}$-NTA column, even in the presence of 8 M urea or 6 M GuHCl. Washing with a solution containing a denaturant prevents interactions between hydrophobic protein fragments and ensures that only His$_6$-tagged fragments are purified.

Once a set of ordered fragments are produced, they may be stored at −20° C. or −70° C. for over a year until they are needed to map the binding of a monoclonal antibody or interacting protein.

D. Gel Electrophoresis

Standard SDS polyacrylamide gel electrophoresis procedures are employed. Colored MW markers (such as the Novex MultiMark Multi-Color Standards) may aid in determining if the transfer to nitrocellulose is efficient and to aid in cutting the nitrocellulose filter if probing with several different radioactive probes or antibodies. Pre-poured 8–16% gradient polyacrylamide Tris-glycine gels (Novex) are useful to visualize both large polypeptides like the E. coli RNA polymerase β' subunit and smaller, e.g., partial proteolysis, fragments on the same gel.

E. Transfer of Protein Fragments from an SDS Gel to a Nitrocellulose Membrane

The proteins or peptides separated by SDS gel electrophoresis are electrophoretically transferred to nitrocellulose membrane as described below prior to either Western analysis or far-Western analysis.

Procedure

1) Cut 1 piece nitrocellulose and 2 pieces Whatman paper (3 MM chromatography paper, Fisher cat. #05-714-5) slightly larger than gel.

2) Pre-wet 1 sponge and 1 piece Whatman paper with Towbin Buffer (TB) (Towbin et al., 1979) (for 2 liters-400 ml methanol (20% final); 500 ml 4×Tris-glycine (1×final; for 1 L of 4×Tris-glycine, pH 8.5–57.6 g glycine and 12.0 g. Tris base); 10 ml 10% SDS (0.05% final).

3) Place Whatman paper on top of the sponge, then place the gel on top of paper.

4) Wet nitrocellulose (Schleicher & Schuell Protran 0.05 μm, cat. #00870) and place it on the gel (avoid bubbles between gel and nitrocellulose) followed by wet Whatman paper and 2 sponges.

5) Place the resulting sandwich in the cage and put it into the transfer box with the nitrocellulose membrane towards the positive terminal.

6) Fill the transfer box with TB and transfer for 3 hours at a constant current of 200 mA (about 60 volts).

7) Remove the nitrocellulose, place it protein side up in a petri dish, add 10–25 ml of Blotto (2% (w/v) Carnation nonfat dry milk in TBST; for 1 liter of TBST-10 ml of 1 M Tris-HCl, pH 7.9 (10 mM final); 37.5 ml of 4 M NaCl (150 mM final); 1 ml Tween 20 (0.1% final)) to cover the blot, and block the membrane for 1–2 hours at room temperature with shaking or overnight at 4° C.

8) For Western analysis: Wash 1× with TBST for about 30 seconds at room temperature; incubate 1 hour at room temperature in 10 ml with 1:1000 dilution of primary antibody; wash 3× with 10 ml TBST for 5 minutes each; incubate 1 hour at room temperature in 10 ml Blotto with 1:1000 dilution of secondary antibody conjugated with horseradish peroxidase (HP) or alkaline phosphatase (AP); wash 3 times with 10 ml TBST for 5 minutes each; and develop with an appropriate calorimetric or chemiluminescent detection reagent.

9) For far-Western analysis: proceed as described in section G below.

F. $^{32}$P Labeling Proteins with Protein Kinase A for Far-Western Probing

If the 5-amino acid recognition site for the catalytic subunit of the cAMP-dependent protein kinase A from heart muscle (RRASV) is attached to the terminus of a cloned protein, the protein can readily be labeled by reaction with $\gamma^{32}$P-ATP and protein kinase A (Li et al., 1989; Blanar et al., 1992; Destka et al., 1999). A cloning vector was prepared that was based on the pET vector pET-28b+ (Novagen), which contains the HMK recognition site and results in an N-terminal addition to a cloned protein of 25 amino acids (deArruda and Burgess, 1996). The vector is available from Novagen as pET-33b(+). Several additional vectors were prepared for the purpose of producing HMK site-tagged protein probes. These constructs contain either a NdeI or NcoI cloning site that allows one to fuse the N-terminal Met of the probe protein to a 13-amino acid N-terminal HMK-His$_6$ tag and provides the choice of either kan$^R$ or an amp$^R$ antibiotic resistance marker. The relevant information about these vectors is summarized below in Table 1.

TABLE 1

| Vector Name | Derived From | N-terminal tag | Cloning Site | Resistance Marker |
|---|---|---|---|---|
| pAP1 | pET-28b | MARRASVHHHHHH (SEQ ID NO:2) | NdeI | kan$^R$ |
| pAP2 | pET-21a | MARRASVHHHHHH (SEQ ID NO:3) | NdeI | amp$^R$ |
| pAP3 | pET-32b | MRRASVHHHHHHA (SEQ ID NO:4) | NcoI | amp$^R$ |

Preparation of HMK Recognition Site-tagged Probe Protein

A BL21 (DE3) E. coli strain (Studier et al., 1990), containing the probe protein cloned into a suitable vector such as one of those described above, is cultured, induced and the inclusion bodies purified as described in Arthur and Burgess (1998). The washed inclusion body may be solubilized with GuHCl or the detergent sodium-N-lauroyl sarcosine (Sarkosyl) and refolded as described in Burgess (1996) and Marshak et al. (1996). Often the washed inclusion bodies are solubilized with 8 M urea and purified either before or after refolding by affinity chromatography on a Ni-chelate column (Burgess et al., 1998).

Procedure

1) Add 5 μl of 10×10×protein kinase A (PKA) Buffer (Pkase Kit, cat. #70510-3 from Novagen) (200 mM Tris-HCl, pH 8.0, 1.5 M NaCl, 200 mM MgCl$_2$, 100 μM ATP) to a 1.5 ml microfuge tube.

2) Add 20–40 μg (about 500 pmol) of protein to be labeled (often stored in 50% glycerol) and bring total volume to 43 μl with MilliQ water. The final glycerol concentration should be 20–25%.

3) Add 5 μl PKA (Novagen; 20 U/μl stock) and 2 μl $\gamma^{32}$P-ATP (NEN/DuPont, 600 Ci/mmol, 5 mCi/33 μl; 300 μCi=6.6×10$^8$ dmp), mix, and incubate for 60 minutes at room temperature.

4) Add 50 μl of 1×Labeling Buffer (1×LB) (25% glycerol; 40 mM Tris-HCl, pH 7.4; 100 mM NaCl; 12 mM MgCl$_2$; 0.1 mM DTT (added fresh)) to reaction, add the resulting 100 μl of diluted reaction to a washed spin column (BioSpin P6 from Bio Rad), and spin 4 minutes at 1000 g. Just before use, vortex the column to resuspend the resin, remove the column bottom, and allow the column to drain. Add 1 ml 1×LB and allow it to flow through by gravity. Spin in Beckman TJ-6 centrifuge (TH-4 swinging bucket rotor) in 50 ml conical plastic tube at 1000 g for 2 minutes at room temperature and discard flow-through.
5) Collect flow through in a microfuge tube.
6) Store labeled probe frozen at −20° C. until use. It can be stored for up to 30 days.

Approximately 30–50% of the label is incorporated into protein, and after the spin column, about 90% of the label is in protein. A typical labeling of HMK-$\sigma^{70}$ at 35 µg in a 50 µl reaction gives about 1–4×$10^6$ cpm/µg. The above protocol yields about 100 µl of material, suitable for probing 10–20 far-Western blots. One can also label with $\gamma^{33}$P-ATP (deArruda and Burgess, 1996). While this gives a lower specific activity, and thus a lower detection sensitivity, it does result in a labeled probe that has a longer half-life and which gives sharper bands on imaging.

G. Probing Far-Western Blots with $^{32}$P-Labeled Protein
Procedure
1) Transfer proteins or fragments from gel or spot proteins onto nitrocellulose membrane.
2) Block the membrane 2 hours in probe buffer (ProB; final 20 mM Hepes, pH 7.2; 200 mM KCl; 2 mM $MgCl_2$-$6H_2O$; 0.1 mM $ZnCl_2$; 1 mM DTT; 0.5% Tween 20; 1% Nonfat dried milk; 10% glycerol; in MilliQ water) at room temperature with shaking (or overnight at 4° C.).
3) Add 5–10 µl of labeled probe ($^{32}$P-labeled protein) solution to 15 ml of ProB and incubate for 2 hours with the membrane at room temperature with shaking.
4) Wash the membrane 3 times for 3 minutes each with 10 ml ProB.
5) Air dry the membrane (about 15 minutes), wrap in Saran Wrap, and expose it to film or a PhosphorImager screen (Molecular Dynamics).

This method is more powerful if one can generate ordered fragment ladders of both—and C-terminally $His_6$-tagged versions of the target protein. That way one can map the interaction domain from both directions. FIG. 2B shows a predicted fragment pattern and a coomassie blue-stained SDS gel for the ordered fragment ladders that results from cleaving both N-terminal (N) and C-terminal (C) $His_6$-tagged E. coli RNA polymerase β' subunit with hydroxy-lamine ($NH_2OH$) or with NTCB. The right-hand part of FIG. 2B shows the results of a far-Western analysis of an identical gel, probed with $^{32}$P-labeled $\sigma^{70}$ (See Example 2).

Ordered fragment ladder far-Western analysis requires that at least a fraction of the molecules in a blotted fragment band are able to refold at least that part of the polypeptide (the interaction domain) needed to create the 3-dimensional interaction surface or interaction site. A number of papers have reported increased refolding and thus sensitivity in far-Western analysis when the blotted target protein is subjected to denaturation followed by renaturation prior to probing (Lieberman and Berk, 1991; Vinson et al., 1988). Presumably, the SDS transferred with the blotted protein is removed (by becoming bound to the large excess of casein in the probe buffer), allowing the target protein to refold, at least partially, on the membrane.

Nitrocellulose pore sizes larger than 0.05 µm can be used, however, 0.05 µm has better retention of small protein fragments.

Several different labeled probes bind non-specifically to colored MW markers, most likely an interaction between the $His_6$-tag or the HMK-tag and the dyes that are attached to the markers. This, however, provides a useful set of labeled markers to help one orient the resulting data.

H. Validating and Characterizing the Far-Western Complex

If a positive signal is detected in a far-Western analysis, additional evidence may be necessary to show that the binding observed is due to a specific, relevant interaction and not merely a non-specific ionic or hydrophobic interaction. These other methods include the co-immobilization assay (Example 2; Arthur and Burgess, 1998; Burgess et al., 1998), and site-directed mutagenesis of the interaction domain (Example 3). The co-immobilization assay involves cloning the putative interaction domain into a vector which links the domain to a $His_6$-tag and passing the resulting protein over a Ni-chelate column. If the probe (lacking a $His_6$-tag) binds to the immobilized target domain and elutes from the column when the target is eluted with imidazole, then one can infer that the two proteins interact. Smaller target domains can be observed in the co-immobilization assay, possibly due to the fact that the refolded target domain is attached to the Ni-chelate column through interaction of its terminal $His_6$-tag and so can display the smallest functional interaction domain. By contrast, the blotted fragment must be attached by at least one or more contacts between the protein and the membrane. It requires that extra amino acids be present to allow binding without interfering with refolding of the minimal interaction domain on the membrane.

Significant non-specific interaction can be ruled out by demonstrating that the labeled probe does not give a signal above background when used to probe a blot of a number of proteins such as BSA or major bacterial proteins in a bacterial extract.

The nature of the probe-target complex can be partially characterized in an ordered fragment ladder far-Western analysis. This can be accomplished by probing as described in section G and then washing the membrane with probe buffer for varying lengths of time and measuring the amount of labeled probe remaining bound to the membrane. In this way, one can determine the approximate half-life of the complex on the membrane. For example, the complexes between $\sigma^{70}$ and fragments of β' dissociate with half-lives of about 2.5 hours. Similarly, one can vary the salt during such a wash and determine the effect of salt on the rate of dissociation.

Conclusions

A positive result is useful provided you can show it is specific. This is a rapid means of detecting binding and locating the region containing an interaction domain. It can direct one to focus more tedious mapping approaches, such as cloning individual truncated fragments or making multiple mutations, to a relatively small segment of the target polypeptide. The use of the $^{32}$P-labeled protein probe allows relatively weak interactions to be detected. The probe can easily be labeled to over $10^6$ cpm/µg and the final wash after incubation of the blot with the probe and before exposure to PhosphorImaging can be as little as 5–10 minutes. In contrast, the detection of bound probe by immunological methods requires incubation with primary and secondary antibodies that can take several hours or more. The extended incubation and wash time can allow the probe to dissociate from the target.

This method does not map the interaction site, but rather the whole region (the interaction domain) needed to form the contact surface or interaction site. An important interaction might not be detected if the interaction domain is difficult to refold or binds the probe protein too weakly. In order to detect binding, one must be within the "window of the assay", i.e., the half-life must be longer than the time of the wash. Convincing results are not obtained if the binding is weak, on the order of the non-specific binding to random proteins or background. This method is ineffective if the interaction domain involves regions of two different-sized polypeptides and might not work if it involves two distant regions of the same polypeptide. It also would work poorly if there were a strong nitrocellulose membrane-binding site in the middle of the interaction domain that prevented refolding on the membrane.

This method is useful to map epitopes of antibodies, protein-protein interaction domain mapping, DNA or RNA binding site mapping, and mapping sites of modification, e.g., sites of radioactive modification, such as phosphorylation or the labeled tag from a tag-transfer cleavable crosslinker (Chen et al., 1994) along a polypeptide. One could start with a $His_6$-tagged protein, allow the modification to occur, chemically or enzymatically cleave the target protein, isolate the $His_6$-tagged fragments on a Ni-chelate column, fractionate by SDS gel electrophoresis, transfer to a membrane, and expose to film or a PhosphorImager screen to determine at which point as you move down the ordered fragment ladder you no longer detect the label.

EXAMPLE 2

Far-Western Blot Analysis of β', β and σ

Materials and Methods

Plasmids

Plasmid characteristics are described in Table 2.

TABLE 2

| Plasmid | Subunit | Residues | Modifications | Ref. |
| --- | --- | --- | --- | --- |
| pTA499 | β' | 1-1407 | N-terminal $His_6$ | Arthur and Burgess, 1998 |
| pTA500 | β' | 1-1407 | C-terminal $His_6$ | Arthur and Burgess, 1998 |
| pTA501 | β | 1-1342 | N-terminal $His_6$ | Arthur and Burgess, 1998 |
| pTA502 | β | 1-1342 | C-terminal $His_6$ | Arthur and Burgess, 1998 |
| pTA515 | β' | 1-260 | None | Arthur and Burgess, 1998 |
| pTA516 | β' | 1-280 | None | Arthur and Burgess, 1998 |
| pTA517 | β' | 1-300 | None | Arthur and Burgess, 1998 |
| pTA518 | β' | 1-309 | None | Arthur and Burgess, 1998 |
| pTA519 | β' | 150-309 | None | Arthur and Burgess, 1998 |
| pTA522 | β' | 1-260 | N-terminal $His_6$-HMK | Arthur and Burgess, 1998 |
| pTA523 | β' | 1-280 | N-terminal $His_6$-HMK | Arthur and Burgess, 1998 |
| pTA524 | β' | 1-300 | N-terminal $His_6$-HMK | Arthur and Burgess, 1998 |
| pTA525 | β' | 1-309 | N-terminal $His_6$-HMK | Arthur and Burgess, 1998 |
| pTA528 | β' | 60-309 | None | Arthur and Burgess, 1998 |
| pTA530 | β' | 100-309 | None | Arthur and Burgess, 1998 |
| pTA531 | β' | 33-309 | N-terminal $His_6$-HMK | Arthur and Burgess, 1998 |
| pTA532 | β' | 60-309 | N-terminal $His_6$-HMK | Arthur and Burgess, 1998 |
| pTA533 | β' | 100-309 | N-terminal $His_6$-HMK | Arthur and Burgess, 1998 |
| pTA534 | β' | 150-309 | N-terminal $His_6$-HMK | Arthur and Burgess, 1998 |
| pTA535 | β' | 178-309 | None | Arthur and Burgess, 1998 |
| pTA536 | β' | 200-309 | None | Arthur and Burgess, 1998 |
| pTA537 | β' | 178-309 | N-terminal $His_6$-HMK | Arthur and Burgess, 1998 |
| pTA538 | β' | 200-309 | N-terminal $His_6$-HMK | Arthur and Burgess, 1998 |
| pTA540 | β' | 260-1407 | C-terminal $His_6$ | Arthur and Burgess, 1998 |
| pTA546 | β' | 260-309 | C-terminal $His_6$ | Arthur and Burgess, 1998 |
| pTA547 | β' | 270-1407 | C-terminal $His_6$ | Arthur and Burgess, 1998 |
| pTA548 | β' | 280-1407 | C-terminal $His_6$ | Arthur and Burgess, 1998 |
| pTA549 | β' | 290-1407 | C-terminal $His_6$ | Arthur and Burgess, 1998 |
| pRL663 | β' | 1-1407 | C-terminal $His_6$ | Wang et al., 1995 |
| pRL706 | β | 1-1342 | C-terminal $His_6$ | Severinov et al., 1999 |
| pHMK-$His_6$-$σ^{70}$ | $σ^{70}$ | 1-613 | N-terminal $His_6$-HMK | Arthur and Burgess, 1998 |
| pLN12 | $σ^{70}$ | 1-613 | None | Rao et al., 1996 |

Construction of Plasmids

An overexpression vector for C-terminal hexahistidine ($His_6$)-tagged β' (pTA500) was constructed by removing the XbaI-HindIII fragment from pRL663 and placing it in pET28b (Novagen) (Studier et al., 1990). N-terminally $His_6$-tagged β' was expressed from pTA499 that was constructed using PCR to place the $His_6$ tag on the N terminus of a fragment that overlapped the NruI site of β'. This fragment was placed into the pET28b vector followed by the insertion of the C-terminal portion of the gene on a NruI-HindIII fragment from pRL663. The C-terminal $His_6$ tag from the pRL663 fragment was removed by replacement of the RsrII-HindIII fragment with a PCR product coding for the wild-type C terminus. pTA501 was constructed by creating an N-terminal $His_6$ tag via PCR for a fragment of β, which overlapped the KpnI site of β. The fragment was placed into the pET28b vector. The C terminus of the gene was added by insertion of a KpnI-HindIII fragment containing the wild type coding sequence. pTA502, coding for the C-terminal $His_6$-tagged β subunit, was derived using PCR to insert a N-terminal NcoI site onto a fragment overlapping KpnI. The C-terminal $His_6$-containing fragment was inserted on a KpnI-HindIII fragment from pRL706 (Severinov et al., 1997).

Vectors expressing unmodified fragments of β' were obtained by PCR cloning of the desired fragment and placement of the fragment into either pET21a (Novagen) for pTA528, pTA530, pTA535, and pTA536 or pET24a (Novagen) for pTA519 using NdeI and XhoI restriction sites. pTA522–525, pTA531, and PTA533 were all created by amplifying the specified β' region via PCR and inserted into a pET21a derivative that had been modified to fuse a N-terminal $His_6$ and heart muscle kinase (HMK) recognition site to the expressed proteins. pTA532 and pTA534 were constructed in the same fashion with the exception that the $His_6$-HMK vector derivative was constructed from pET28b. pTA547–549 were created by inserting the fragments, N-terminally truncated via PCR, that overlapped the SnaBI site of β' into pET24a. The C-terminal coding region of the gene was inserted on a SnaBI-HindIII fragment from pTA500. pTA546 was created by fusing a C-terminal $His_6$ tag directly after residue 309 via PCR. The fragment was placed into the pET24a vector using NdeI and XhoI sites. To use $σ^{70}$ as a radioactive probe, the HMK site was fused to the N terminus of $\sigma^{70}$ along with a His$_6$ purification tag. pHMK-His$_6$-$\sigma^{70}$ was created by placing the $\sigma^{70}$ gene into a derivative of pET28b vector that contained the N-terminal His$_6$ and HMK fusion and adds a total of 13 extra amino acids (MHHHHHHARRASV; SEQ ID NO:5) to the N terminus of $\sigma^{70}$. All products created by PCR were sequenced to ensure that no mutations had been introduced.

Expression and Purification of Proteins

Plasmids were transformed into BL21(DE3) (Novagen) for expression. The cells were grown in 1 liter cultures at 37° C. in LB medium with either 100 µg/ml ampicillin or 50 µg/ml kanamycin. The cultures were grown to an A$_{600}$ between 0.6 and 0.8 and then induced with 1 mM isopropyl-β-D-thiogalactopyranoside. Three hours after induction, the cells were harvested by centrifugation at 8,000×g for 15 minutes and frozen at −20° C. until use.

The cells were thawed and resuspended in 10 ml of lysis buffer (40 mM Tris-HCl, pH 7.9, 0.3 M KCl, 10 mM EDTA, and 0.1 mM phenylmethylsulfonyl fluoride), and lysozyme was added to 100 µg/ml. The cells were incubated on ice for 15 minutes then sonicated three times in 60 second bursts. The recombinant protein in the form of inclusion bodies was separated from the soluble lysate by centrifugation at 27,000×g for 15 minutes. The inclusion body pellet was resuspended, by sonication, in 10 ml of lysis buffer +2% (w/v) sodium deoxycholate. The mixture was centrifuged at 27,000×g for 15 minutes and the supernatant discarded. The deoxycholate-washed inclusion bodies were resuspended in 10 ml deionized water and centrifuged at 27,000×g for 15 minutes. The water wash was repeated, and the inclusion bodies were aliquoted into 1 mg pellets and frozen at −20° C. until use.

$\sigma^{70}$ inclusion bodies were solubilized, refolded, and purified according to a variation of the procedure of Gribskov and Burgess (1983). The inclusion bodies were solubilized by resuspension in 6 M guanidine HCl (GuHCl). The proteins were allowed to refold by diluting the denaturant 64-fold with buffer A (50 mM Tris-HCl, 0.5 mM EDTA, and 5% (v/v) glycerol) in 2-fold steps over 2 hours. One gram of DE52 resin (Whatman) was added and mixed with slow stirring for 24 hours at 4° C. The resin was then collected in a 10 ml column, washed, and the protein eluted with a gradient from 0.1 to 1 M NaCl in buffer A. The $\sigma^{70}$ fractions were pooled and dialyzed overnight against 1 liter of storage buffer (50 mM Tris-HCl, 0.5 mM EDTA, 0.1 M NaCl, 0.1 mM DTT, and 50% (v/v) glycerol) and stored at −20° C.

Whole cell lysates were prepared as follows. Cells containing truncated β' expression plasmids were grown to an A$_{600}$ of 0.6–0.8 and induced with 1 mM isopropyl-β-D-thiogalactopyranoside. The cells were grown for an additional 30 minutes. A 200 µl sample was removed and sonicated 3×30 seconds. Twenty µl of glycerol and 20 µl of SDS-sample buffer were added and heated for 2 minutes at 95° C. then stored at −20° C. until use.

Protein Cleavage

β and β' inclusion bodies were subjected to chemical or enzymatic cleavage (see below) and then purified by nickel affinity chromatography as follows. The cleavage reaction was loaded onto 300 µl of Ni$^{2+}$-NTA resin (Qiagen) in a Bio-Rad mini-column. The resin had been pre-equilibrated with buffer B (20 mM Tris-HCl, pH 7.9, 500 mM NaCl, 5 mM imidazole, 0.1% (v/v) Tween 20, and 10% (v/v) glycerol)+8 M urea. The protein bound resin was washed with 10 column volumes of buffer B+8 M urea followed by 10 column volumes of buffer B to allow refolding. The resin was then washed with 500 µl of buffer B+40 mM imidazole. The protein was eluted with 500 µl of buffer B+200 mM imidazole. The eluted fractions were stored at −20° C.

NTCB Cleavage (Jacobson et al., 1983)

One mg of inclusion body protein was resuspended in 1 ml of buffer B+8 M urea. DTT was added to 5-fold molar excess over the thiol groups in the protein. The mixture was incubated for 15 minutes at 37° C. to reduce any disulfide bonds. NTCB was added to 5-fold molar excess over total sulfhydryl groups. The pH was adjusted to 9.5 with NaOH. The reaction mixture was incubated for 2 hours at room temperature. The cleavage mixture was diluted 1:10 in buffer B+8 M urea and loaded onto a Ni$^{2+}$-NTA column as described above.

Hydroxylamine Cleavage (Bornstein et al. 1970)

One mg of inclusion body protein was resuspended in 1 ml of buffer B plus 8 M urea. Five-hundred microliters of the solubilized protein were added to 500 µl of hydroxylamine cleavage solution (0.4 M CHES, pH 9.5, 4 M hydroxylamine HCl) and incubated 2 hours at 42° C. β-Mercaptoethanol was added to 0.1 M and incubated 10 minutes at 37° C. The mixture was diluted 1:10 in buffer B+8 M urea and loaded onto a Ni$^{2+}$-NTA column as described above.

Themolysin Cleavage (Rao et al. 1996)

One mg of inclusion body protein was resuspended in 100 µl of buffer B+8 M urea and incubated for 15 minutes at 37° C. Thermolysin was added at protein:protease ratios of 4,000:1, 8,000:1, and 16,000:1 (w/w). Reactions were carried out for 30 minutes at room temperature. The reactions were loaded onto a Ni$^{2+}$-NTA column as described above.

Trypsin Cleavage (Rao et al. 1996)

One mg of inclusion body protein was resuspended in 1 ml of buffer B+8 M urea and incubated for 15 minutes at 37° C. The mixture was diluted to 4 M urea by adding an equal volume of buffer B. Trypsin was added at protein:protease ratios of 4,000:1, 8,000:1, and 16,000:1 (w/w). Digestion was performed at room temperature for 30 minutes. The reactions were loaded onto a Ni$^{2+}$-NTA column as described above.

Far-Western Blotting

Dot Blot

Inclusion body proteins that were resuspended in buffer B+8 M urea were spotted directly onto a nitrocellulose membrane (Schleicher & Schuell) using a Schleicher & Schuell "MINIFOLD" dot blot apparatus. The wells were washed three times with buffer B. The nitrocellulose was blocked by incubation in HYB buffer (20 mM Hepes, pH 7.2, 200 mM KCl, 2 mM MgCl$_2$, 0.1 mM ZnCl$_2$, 1 mM DTT, 0.5% (v/v) Tween 20, 1% (w/v) non-fat dry milk) for 16 hours at 4° C.

Gel Blot

Protein cleavage fragments or whole cell lysates were separated by SDS-polyacrylamide gel electrophoresis (PAGE). The proteins were electrophoretically transferred onto 0.05 µm nitrocellulose. The nitrocellulose was blocked by incubating in HYB buffer for 16 hours at 4° C.

Labeling

Labeling of $\sigma^{70}$ was done in a 100-µl reaction volume. Fifty µl of 2×kinase buffer (40 mM Tris-HCl, pH 7.4, 200 mM NaCl, 24 mM MgCl$_2$, 2 mM DTT, and 50% (v/v) glycerol) was added to 50 µg of $\sigma^{70}$ protein. 240 units of cAMP-dependent kinase-catalytic subunit (Promega) was added, and the total volume was brought up to 99 µl with deionized water. One microliter of [γ-$^{32}$P]ATP (0.15 mCi/µl) was added. The mixture was incubated at room temperature for 30 minutes. The reaction mixture was then loaded onto a Biospin-P6 column (Bio-Rad) pre-equilibrated with 1×kinase buffer and spun at 1,100×g for 4 minutes. The flow-through was collected and stored at −20° C.

Probing

The blocked nitrocellulose was incubated in 10 ml of HYB buffer with $4 \times 10^5$ cpm/ml $^{32}$P-labeled $\sigma^{70}$ for 3 hours at room temperature. The blot was washed three times with 10 ml of HYB buffer for 3 minutes each. The blot was then dried and exposed to film or PhosphorImager (Molecular Dynamics).

Co-immobilization

One milligram of $His_6$-tagged, truncated $\beta'$ was solubilized in 1 ml of buffer C (20 mM Tris-HCl, pH 7.9, 200 mM NaCl, 5 mM imidazole, 0.1% (v/v) Tween 20, and 10% (v/v) glycerol)+8 M urea. Twenty micrograms of the protein solution were loaded onto 150 $\mu$l of $Ni^{2+}$-NTA resin. The column was washed with 15 column volumes of buffer C+8 M urea, followed by a 15-column volume wash with buffer C to allow refolding. Then 30 $\mu$g of native $\sigma^{70}$ were loaded onto the column. The column was washed with 20 volumes of buffer C. The bound proteins were eluted with 300 $\mu$l of buffer C+250 mM imidazole. Samples from the $\sigma^{70}$ flow-through, wash, and elution fractions were analyzed by SDS-PAGE.

Results $\sigma^{70}$ Interacts Strongly with $\beta'$ Subunit and Weakly with $\beta$ Subunit in Far-Western Blot Analysis Far-Western assays of dot blots were used to assess the binding of $\sigma^{70}$ to individual $\beta$ and $\beta'$ subunits outside of the core complex. Inclusion body proteins of $\beta$ and $\beta'$ were separately solubilized in urea and spotted onto nitrocellulose. Bovine serum albumin (BSA) was spotted as a control for nonspecific binding. The nitrocellulose was blocked and the denaturant washed away. The blot was then probed with $^{32}$P-labeled $\sigma^{70}$. Both $\beta$ and $\beta'$ subunits bound $\sigma^{70}$, the BSA control did not. Identical dot blots were probed with control solutions lacking either the kinase or $\sigma^{70}$ to ensure that the signal was not due to nucleotide binding or phosphorylation of the $\beta$ or $\beta'$ subunits. Neither control blot produced a detectable signal. Thus, both $\beta$ and $\beta'$ subunits can individually bind $\sigma^{70}$.

$\sigma^{70}$ Interaction Specific for $\beta/\beta'$ in Far-Western Analysis

An additional test was performed to assess the specificity of the far-Western analysis using $\sigma^{70}$ as a probe. A cell lysate from a log phase culture was separated by SDS-PAGE, blotted onto nitrocellulose, and probed with $\sigma^{70}$. The only strong signal produced had the same mobility as $\beta$ and $\beta'$. The absence of other strong signals indicates that $\sigma^{70}$ is not binding nonspecifically to $\beta$ and/or $\beta'$. Minor bands were observed as expected, since there are other proteins that have been shown to interact with $\sigma^{70}$ (activators, anti-$\sigma$, etc.) (Ishihama, 1993; Jishage et al., 1998).

A Strong, Specific Binding Site for $\sigma^{70}$ Is Located in the N Terminus of the $\beta'$ Subunit To map the $\sigma^{70}$ interaction sites on $\beta$ and $\beta'$, far-Western analysis of chemical cleavage products of the two large subunits was performed. The amino acid sequences of both were analyzed using MacVector software (Oxford Molecular Group) to identify specific chemical cleavage sites. Based on this analysis, cleavage reagents were chosen that produced an array of products following partial digestion that provide the highest resolution for mapping. Both N- and C-terminal $His_6$-tagged constructs of $\beta$ and $\beta'$ were subjected to cleavage under denaturing conditions. The products of the cleavage reaction were purified under denaturing conditions using $Ni^{2+}$-NTA resin to isolate cleavage fragments containing a $His_6$ tag. These purified fragments were then identified based on their mobility in SDS-PAGE, and their exact size was determined based on the cleavage site which produced them. When the cleavage fragments were fractionated by SDS-PAGE, they produced a ladder of descending sized fragments with a common end (either N or C terminus depending on the placement of the $His_6$ tag). The use of both N- and C-terminally $His_6$-tagged fragments allows the positive identification of both the N and C termini of the interaction domain. The $\sigma^{70}$ probe will only bind the fragments that have an intact interaction domain. The N-terminally $His_6$-tagged $\beta'$ ladders produced by hydroxylamine and NTCB cleavage both contained several fragments that retained the ability to bind $\sigma^{70}$. Thus, a large portion of the C terminus of $\beta'$ can be removed without affecting $\sigma^{70}$ binding. The smallest fragment to bind $\sigma^{70}$ was the 1–309 amino acid fragment of $\beta'$ in the hydroxylamine ladder. In the C-terminally $His_6$-tagged ladders, only full-length $\beta'$ bound $\sigma^{70}$. These results indicated that a strong specific binding site is located within amino acids 1–309 of $\beta'$ ($\beta'_{1-309}$). The $\beta$ fragment ladders failed to produce signals strong enough to effectively map the interaction domain.

The resolution of chemical cleavage mapping was relatively low due to the limited number of cleavage sites on $\beta'$ for the reagents available. To increase the number of proteolytic fragments that could be used in mapping, we used enzymatic cleavage. Specificity of cleavage by many proteases is not as limited as with chemical cleavage reagents. Therefore, there are many more sites of cleavage and more fragments are produced. Partial digests of N- and C-terminally $His_6$-tagged $\beta'$ were conducted using trypsin and thermolysin. The fragments were again purified, blotted, and probed with $\sigma^{70}$. However, even with the increased number of fragments, the interaction domain could not be narrowed from its previous length of 1–309 amino acids.

Interaction Domain Narrowed to 60–309 aa by Far-Western Blotting with Truncated Fragments In trying to define this binding site more precisely, various truncated fragments were made using PCR. Using the $\beta'_{1-309}$ fragment as a starting point, constructs were made that were truncated at either the N or C terminus. DNA coding for the truncated fragments was cloned into overexpression plasmids. When cells containing these plasmids had been grown to an $A_{600}$ of 0.6, expression was induced. The cells were only allowed to grow for 30 minutes after induction. A whole cell lysate from each culture was made and used for far-Western blotting assays. Short expression times kept the expression level of the induced protein comparable with the other proteins in the lysate. The use of the whole cell lysate in far-Western blotting assays was an internal control to ensure binding was specific for the protein of interest. This also meant that the various proteins would not have to be purified and could be expressed without purification tags. When constructs were made where the C terminus of $\beta'_{1-309}$ was truncated beyond amino acid 300, the binding of $\sigma^{70}$ was lost. However, the N terminus of the same fragment could be truncated up to 60 aa without diminishing the signal. $\beta'_{100-309}$ still showed binding, but at a lower level, and $\beta'_{150-309}$ did not bind $\sigma^{70}$. These results narrowed the $\sigma^{70}$ binding site to $\beta'_{60-309}$. Western blot experiments using anti-$\beta'$ monoclonal antibodies were done to ensure that the protein fragments were being transferred to the nitrocellulose and that they were fragments of $\beta'$.

Co-immobilization Assays Further Narrow Interaction Site to Residues 260–309 of $\beta'$ $Ni^{2+}$-NTA co-immobilization assays were used to confirm and extend the results that had been produced using far-Western blotting. The proteins to be assayed for binding $\sigma^{70}$ were fused to $His_6$ purification tags and overexpressed in the form of inclusion bodies. The inclusion body protein was solubilized with 8 M urea and loaded onto $Ni^{2+}$-NTA resin. The denaturant was washed away allowing the proteins to refold while still remaining bound to the resin. Native $\sigma^{70}$ was then loaded onto the column. The column was washed, and the bound proteins were then eluted with imidazole. Any truncated protein that contained the interaction domain for $\sigma^{70}$ would cause $\sigma^{70}$ to be bound and to be in the eluted fraction. The results of these binding experiments are consistent with the far-Western blotting experiments in respect to defining the C-terminal boundary of the domain. $\beta'_{1-309}$ bound $\sigma^{70}$, while $\beta'_{1-300}$ and $\beta'_{1-280}$ did not bind (70 Refolded $\beta'_{1-309}$ without a His$_6$ tag was mixed with $\sigma^{70}$ and passed over the Ni$^{2+}$-NTA to ensure the complex was not nonspecifically binding to the column. The complex passed through the column and was not seen in the eluted fraction. As a control, BSA was loaded onto a column containing $\beta'_{1-309}$. BSA was seen only in the flow-through and not in the eluted fraction, suggesting $\beta'_{1-309}$ binds $\sigma^{70}$ specifically.

For the N-terminal boundary, the results showed that more of the N terminus could be removed without affecting $\sigma^{70}$ binding than was seen by the far-Western assay. Several N-terminally truncated fragments, all having aa 309 as the C-terminal boundary followed by a His$_6$ tag, were constructed and used in co-immobilization assays. Truncations to residues 33, 60, 100, 178, and 200 still produced fragments capable of binding $\sigma^{70}$. $\beta'_{260-309}$, that was prepared and could be manipulated efficiently, retained the ability to bind $\sigma^{70}$. To find the N terminus of the interaction domain, truncations greater than residue 240 were made from full-length $\beta'$. A truncation of the first 260 residues of $\beta'$ ($\beta'_{260-C}$) bound $\sigma^{70}$, while $\beta'_{270-C}$ showed diminished binding, and $\beta'_{280-C}$ showed no detectable binding of $\sigma^{70}$. Taken together these results indicate that a strong $\sigma^{70}$ binding site on the core polymerase is located within the residues 260–309 of $\beta'$.

Discussion

To date, several biochemical and genetic studies have contributed to what is known about the putative core binding domains on $\sigma$, however, much less is known about the sites on core that bind $\sigma$ (Gross et al., 1996). In the holoenzyme assembly pathway, $\beta'$ is added to the $\alpha_2\beta$ complex and then $\sigma$ is added to form the holoenzyme (Ishihama, 1981). This would suggest that either the major $\sigma$ binding site is located on $\beta'$ or is formed in cooperation with $\alpha$ and/or $\beta$ upon $\beta'$ assembly into the core enzyme. The isolation of $\sigma^{70}.\beta'$ complexes provides evidence for the former (Luo et al., 1996). The results described hereinabove have localized a strong binding site for $\sigma^{70}$ on $\beta'$, as well as identified low level binding affinity for $\sigma^{70}$ to $\beta$. Thus, $\beta'$ provides the major binding interaction for $\sigma^{70}$ in the holoenzyme while $\beta$ adds a secondary binding interaction. Multiple core binding sites on $\sigma$ have been suggested in light of $\sigma$ mutations apparently affecting core binding that map outside of conserved region 2.1 (Joo et al., 1997; Zhou et al., 1992; Joo et al., 1998; Sharp et al., 1999).

A strong binding site for $\sigma^{70}$ is located within residues 260–309 of $\beta'$. A deletion of residues 201–477 of $\beta'$ has been reported previously to produce a mutant protein that could still form core but not holoenzyme (Luo et al., 1996). The problem with such deletion studies is that one cannot conclude that the binding site is located in the region deleted, but merely that the region, when deleted, prevents correct formation of the interaction domain. Results obtained from protein-protein footprinting experiments indicated that a similar region of $\beta'$ (residues 228–461) was physically close to $\sigma^{70}$ (Owens et al., 1998). There is difficulty in interpreting these results, since the assay gives indications of physical proximity of the proteins that do not necessarily correspond to protein-protein binding. From the findings described herein it can be concluded that a major $\sigma^{70}$ binding site is located within these regions.

The $\sigma^{70}$ interaction domain on $\beta'$ contains several residues located in conserved region B (Jokerst et al., 1989). This region does not have any known function. Secondary structural predictions derived from the PHD program (Rost et al., 1994) for residues 260–309 indicates one helix from residue 264 to residue 283 connected by a loop to a second helix from residue 292 to residue 309. These predicted helices are also predicted to form coiled coils (Lupas et al., 1991). This is of particular interest, since similar predictions were made for residues 355–391 of $\sigma^{70}$. These residues overlap conserved region 2.1. The crystal structure of the protease-resistant fragment of $\sigma^{70}$ confirmed the prediction that the helix containing region 2.1 is forming a coiled coil with conserved region 1.2 (Malhotra et al., 1996). Since coiled coils have been shown to be involved in many protein-protein interactions (Landschulz et al., 1988; Gentz et al., 1989; O'Shea et al., 1989), this would suggest that $\alpha'_{260-309}$ may be interacting with region 2.1 of $\sigma^{70}$.

Ordered fragment ladder far-Western blotting was used to map the $\sigma^{70}$. binding site on $\beta'$ to within $\beta'_{60-309}$. This method relies on the fact that after the removal of the denaturant some fraction of the blotted protein will be able to refold and produce the proper conformation for binding of the probe. The specificity of the assay was demonstrated by probing whole cell lysates and identifying $\beta'$ as the major binding interaction. The combination of specific chemical cleavage of proteins and far-Western blotting provided a very rapid and effective way to localize this protein-protein interaction. Cloning and screening individual, truncated fragments was necessary only after the interaction domain had been targeted. Having to make truncations of $\beta'$ all along its length would have been a long and tedious process. The protein cleavage and Ni$^{2+}$ column purification procedures can be done in one day, thus making the assay more expedient and less tedious.

To confirm and extend the results obtained with far-Western blotting, Ni$^{2+}$ co-immobilization assays were performed. These experiments also demonstrated that fragments from the N terminus to residue 309 could still bind $\sigma^{70}$, while removal of just 9 C-terminal residues to aa 300 would abolish binding. The results obtained from the N-terminally truncated fragments in these assays gave much better resolution of the binding site location than was obtained from far-Western assays. Up to 260 residues could be removed from the N terminus without affecting $\sigma^{70}$ binding. When 270 residues were removed, binding of $\sigma^{70}$ was diminished but not abolished, suggesting that either part of the binding site had been removed or the binding site was intact but hindered from refolding due to the loss of upstream residues. To ensure that the binding site was what was actually mapped and not just a region required for proper folding of the actual binding site, protein fragments were made from 260–309 of $\beta'$ and shown to be sufficient for binding. The difference in the identified interaction domain size between the far-Western assay ($\beta'_{60-309}$) and the co-immobilization assay ($\beta'_{260-309}$) is consistent with the properties of each assay. The far-Western assay requires the interaction domain to refold and properly present the binding site while some portion of the protein is attached to the nitrocellulose membrane. As such the proteins are more conformationally restricted than proteins bound only at one terminus as in the Ni$^{2+}$-NTA co-immobilization assay. Therefore, more of the protein length is required to form a scaffold-like structure to keep the interaction domain away from the membrane surface. The combination of mapping methods provides a rapid, high resolution procedure for identification of protein interaction domains.

EXAMPLE 3

Mutational Analysis of $\beta'_{260-309}$

Materials and Methods

Construction of Plasmids

Plasmid characteristics are described in FIG. 7 and Tables 3–4. Plasmids pTA577 and 600–620 were made from the base plasmid pRL663 (Wang et al., 1995). Single HindIII and BamHI restriction sites were inserted into the rpoC gene of pRL663 via silent mutagenesis to create pTA577. pTA561 was created in the same manner as pTA577 except pRL308 (Weilbaecher et al., 1994) was the starting plasmid. The HindIII and BamHI restriction sites were used to insert PCR generated DNA fragments containing the various mutations to generate pTA600–609. For pTA620, containing a truncated rpoC fragment coding for $\beta'$ residues 1–319, pRL663 was cut with XbaI HindIII for insertion of the PCR generated rpoC truncation. The $\sigma^{70}$ binding site was mapped to 260–309 of $\beta'$, however, some of the constructs were engineered to extend to residue 319. This was done to incorporate the BamHI site mentioned above. Thus, the various mutations were moved into the new plasmid to create pTA610–619. There was no observed difference in the properties of the fragments ending to residue 309 as opposed to those ending to residue 319.

Plasmids pTA145, 655, 658, 660 and 661 were constructed by inserting PCR generated rpoC fragments, coding for $\beta'_{240-309}$ wild type or the various mutants, into the NdeI-XhoI restriction sites of pET24a. C-terminal His$_6$ tags were incorporated in the reverse primers for these inserts to fuse the purification tags to the expressed proteins.

TABLE 3

| Plasmid | $\beta'$ residues | Mutation | Modifications | Reference |
| --- | --- | --- | --- | --- |
| pRL308 | 1-1407 | none | none | Weilbaecher et al., 1994 |
| pRL663 | 1-1407 | none | C-terminal His$_6$ | Wang et al., 1995 |
| pTA561 | 1-1407 | silent | none | This work |
| pTA577 | 1-1407 | silent | C-terminal His$_6$ | This work |
| pTA600 | 1-1407 | N266D | C-terminal His$_6$ | This work |
| pTA601 | 1-1407 | Y269A | C-terminal His$_6$ | This work |
| pTA602 | 1-1407 | R275Q | C-terminal His$_6$ | This work |
| pTA603 | 1-1407 | K280E | C-terminal His$_6$ | This work |
| pTA604 | 1-1407 | R293Q | C-terminal His$_6$ | This work |
| pTA605 | 1-1407 | E295K | C-terminal His$_6$ | This work |
| pTA606 | 1-1407 | R297S | C-terminal His$_6$ | This work |
| pTA607 | 1-1407 | Q300E | C-terminal His$_6$ | This work |
| pTA608 | 1-1407 | A302D | C-terminal His$_6$ | This work |
| pTA609 | 1-1407 | N309D | C-terminal His$_6$ | This work |
| pTA610 | 1-319 | N266D | none | This work |
| pTA611 | 1-319 | Y269A | none | This work |
| pTA612 | 1-319 | R275Q | none | This work |
| pTA613 | 1-319 | K280E | none | This work |
| pTA614 | 1-319 | R293Q | none | This work |
| pTA615 | 1-319 | E295K | none | This work |
| pTA616 | 1-319 | R297S | none | This work |
| pTA617 | 1-319 | Q300E | none | This work |
| pTA618 | 1-319 | A302D | none | This work |
| pTA619 | 1-319 | N309D | none | This work |
| pTA620 | 1-319 | silent | none | This work |

TABLE 4

| Plasmid # | | Far-Western binding | Growth at 42° C. | Assembly E$\sigma$70 holo | Assembly E$\sigma$32 holo | Toxic |
| --- | --- | --- | --- | --- | --- | --- |
| | wt | + | + | + | + | + |
| | R297L | +/− | − | | | + |
| | L299D | − | − | | | − |
| | E301K | + | + | | | + |
| | E301P | − | − | | | − |
| | R270L | + | + | | | |
| | V272D | − | − | | | |
| | N274D | + | + | | | |
| | N274P | − | − | | | |
| 600 | N266D | + | − | +/− | − | + |
| 601 | Y269A | + | + | + | +/− | − |
| 602 | R275Q | − | − | − | − | − |
| 603 | K280E | + | + | + | + | + |
| 604 | R293Q | +/− | +/− | +/− | + | + |
| 605 | E295K | − | − | − | − | − |
| 606 | R297S | − | +/− | − | + | + |
| 607 | Q300E | + | + | + | +/− | + |
| 608 | A302D | − | − | − | − | − |
| 609 | N309D | + | + | + | + | + |

Expression and Purification of $\sigma^{70}$

The cells were grown to an A$_{600}$ between 0.6–08 in 1 L cultures at 37° C. in LB medium with 100 µg/ml ampicillin. Isopropyl β-D-thiogalactoside (IPTG) was then added to a concentration of 1 mM. Three hours after induction, the cells were harvested by centrifugation at 8,000×g for 15 minutes and frozen at −20° C.

The cell pellet from a 1 L culture was thawed and resuspended in 10 ml of lysis buffer (40 mM Tris-HCl, pH 7.9, 0.3 M KCl, 10 mM EDTA and 0.1 mM phenylmethylsulfonyl fluoride) and lysozyme was added 0.1 mg/ml. The cells were incubated on ice for 15 minutes then sonicated 3×60 second bursts. The recombinant protein in the form of inclusion bodies was separated from the soluble lysate by centrifugation at 27,000×g for 15 minutes. The inclusion body pellet was resuspended by sonication in 10 ml of lysis buffer +2% (w/v) sodium deoxycholate (DOC). The mixture was centrifuged at 27,000×g for 15 minutes and the supernatant was discarded. The DOC-washed inclusion bodies were resuspended in 10 ml deionized water and centrifuged at 27,000×g for 15 minutes. The water wash was repeated and the inclusion bodies were aliquoted into 1 mg pellets and frozen at −20° C. until use.

$\sigma^{70}$ inclusion bodies (10 mg) were solubilized, refolded and purified according to a variation of the procedure of Gribskov and Burgess (1986). The inclusion bodies were solubilized by resuspension in 10 ml of 6 M guanidine-HCl. The proteins were allowed to refold by diluting the denaturant 64-fold with buffer A (50 mM Tris-HCl, pH 7.9, 0.5 mM EDTA, and 5% (v/v) glycerol) in 2-fold steps over 2 hours. One gram of resin (DEAE-cellulose, Whatman) was added and mixed with slow stirring for 24 hours at 4° C. The resin was then collected in a 10 ml column, washed, and the protein eluted with a gradient from 0.1 to 1.0 M NaCl in buffer A. The $\sigma^{70}$ fractions were pooled and dialyzed overnight against 1 L of storage buffer (50 mM Tris-HCl, pH 7.9, 0.5 mM EDTA, 0.1 M NaCl, 0.1 mM DTT and 50% (v/v) glycerol) and stored at −20° C.

Quantitative Western Blotting

Protein samples to be quantitated were subjected to SDS-polyacrylamide gel electrophoresis (PAGE). The proteins were electrophoretically transferred out of the gel onto 0.05 µm nitrocellulose. The blot was blocked in Blotto and probed with monoclonal antibodies (MAbs). The signal was generated using the ECL+ system (Amersham) and detected on a Storm FluoroImager (Molecular Dynamics). The signal was quantitated using ImageQuant software (Molecular Dynamics).

Far-Western Blotting

Cells containing truncated β' expression plasmids pTA610–620 were grown to an $A_{600}$ of 0.6–0.8 and induced with 1 mM IPTG. The cells were grown for an additional 30 minutes. A 200 μl sample was removed and sonicated 3×30 seconds. Twenty μl of glycerol and 20 μl of SDS-sample buffer were added and heated for 2 minutes at 95° C. then stored at −20° C. until use. The lysates were separated by SDS-PAGE. The proteins were electrophoretically transferred onto 0.05 μm nitrocellulose. The nitrocellulose was blocked by incubating in HYB buffer (20 mM Hepes, pH 7.2, 200 mM KCl, 2 mM $MgCl_2$, 0.1 μM $ZnCl_2$, 1 mM DTT, 0.5% (v/v) Tween 20, 1% (w/v) non-fat dry milk) for 16 hours at 4° C.

Labeling of $\sigma^{70}$ was done in a 100 μl of 2×kinase buffer (40 mM Tris-HCl, pH 7.4, 200 mM NaCl, 24 mM $MgCl_2$, 2 mM DTT) was added to 50 μg of HMK-$\sigma_{70}$ protein. Two hundred and forty (240) U of cAMP-dependent kinase catalytic subunit (Promega) was added and the total volume was brought to 99 μl with deionized water. One microliter of $\gamma$-$^{32}$P-ATP (0.15 mCi/ml) was added. The mixture was incubated at room temperature for 30 minutes. The reaction mixture was then loaded onto a Biospin-P6 column (BioRad) pre-equilibrated with 1×kinase buffer and spun at 1100×g for 4 minutes. The flow-through was collected and stored at −20° C.

The blocked nitrocellulose was incubated in 10 ml of HYB buffer with 4×10$^5$ cpm/ml $^{32}$P-labeled $\sigma^{70}$ for 3 hours at room temperature. The blot was washed three times with 10 ml of HYB buffer for 3 minutes each. The blot was dried and the signal was visualized with a PhosphorImager and quantitated with IMAGEQUANT software (Molecular Dynamics).

Growth Assessment

Plasmids pTA577, 600–609 (0.1 μg) were transformed into strain RL602 (Weilbaecher et al., 1994; Ridley et al., 1982). After heat shock and incubation on ice, 300 μl of LB was added to the 50 μl cell mixture. Ten μl of the transformation reaction was spotted onto LB plates plus ampicillin (100 μg/ml) and incubated at 30° C. Another 10 μl was spotted onto plates and incubated at 42° C. The plates were incubated between 24–48 hours and assessed for growth.

Purification of Core/holoenzyme Complexes

One L flasks containing 200 ml of LB with ampicillin (100 μg/ml) and IPTG (0.15 mM) were inoculated with 200 μl from an overnight culture of cells containing plasmids pTA561, 577, 600–609. The cultures were grown at 37° C. with shaking until the $A_{600}$=0.4 for log phase assays and 2 hours longer ($A_{600}$ about 2.0) for the early stationary phase assays. The cells were harvested by centrifugation at 6,000 rpm for 10 minutes and stored at −20° C. until use. The cell pellets were resuspended in 5 ml TE (10 mM Tris-HCl, pH 7.9 and 0.1 mM EDTA) plus 0.15 M NaCl and lysozyme (0.1 mg/ml) then incubated on ice for 15 minutes. The cells were sonicated 2×30 seconds and centrifuged for 25 minutes at 27,000×g to pellet the insoluble material. The supernatant was loaded onto a 1.5 ml immunoaffinity column containing the polyol-responsive, anti-β' monoclonal antibody (MAb), NT73 (Thompson et al., 1992). The column was washed with 15 ml TE plus 0.15 M NaCl followed by a second wash with 10 ml TE plus 0.5 M NaCl. The protein was eluted from the column with 4 ml TE plus 0.7 M NaCl and 30% propylene glycol. The eluted sample (4 ml) was diluted with 6 ml buffer B (20 mM Tris-HCl, pH 7.9, 500 mM NaCl, 5 mM imidazole, 0.1% (v/v) Tween 20, and 10% (v/v) glycerol) and loaded (2×) onto 500 μl of $Ni^{2+}$-NTA resin. The resin was washed (2×) with 5 ml of buffer B and eluted with 0.5 ml buffer B plus 0.25 M imidazole. Samples from the elution fractions were assayed by Western blot as described above using Mabs to each subunit or σ factor. The secondary antibodies were horseradish peroxidase-labeled goat antimouse IgG antibodies and the signal was generated using the ECL+ substrate system (Amersham) and detected using the STORM FluoroImager and quantitated with IMAGEQUANT software (Molecular Dynamics).

Results

Mutational Design

Figure 3A:
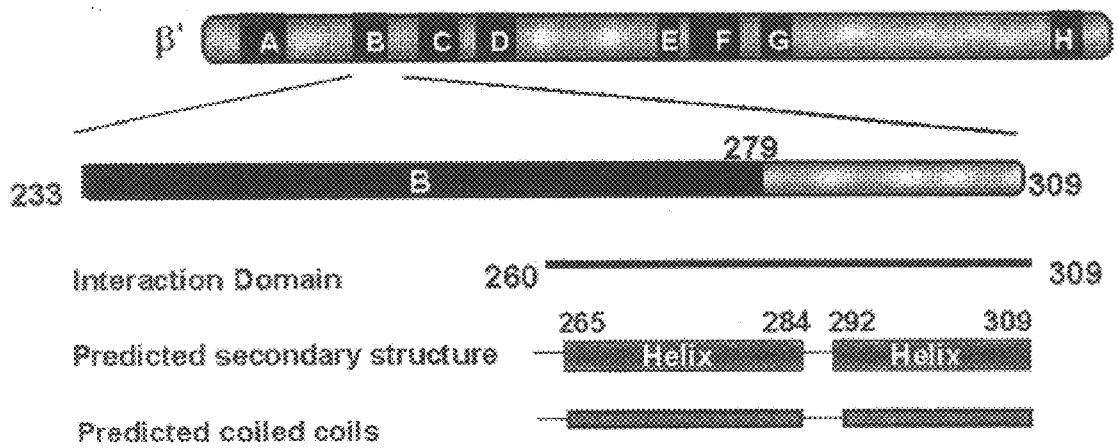
FIG. 3A. Schematic diagram of β'$_{260-309}$ interaction domain. The lettered boxes represent the conserved regions of eukaryal and prokaryal RNA polymerase largest subunits (Jokerst et al., 1989). β'$_{260-309}$ interaction domain overlaps part of the β' subunit conserved region B. Below the interaction domain are diagrams of the predicted α helices and coiled coils.
Figure 3B:
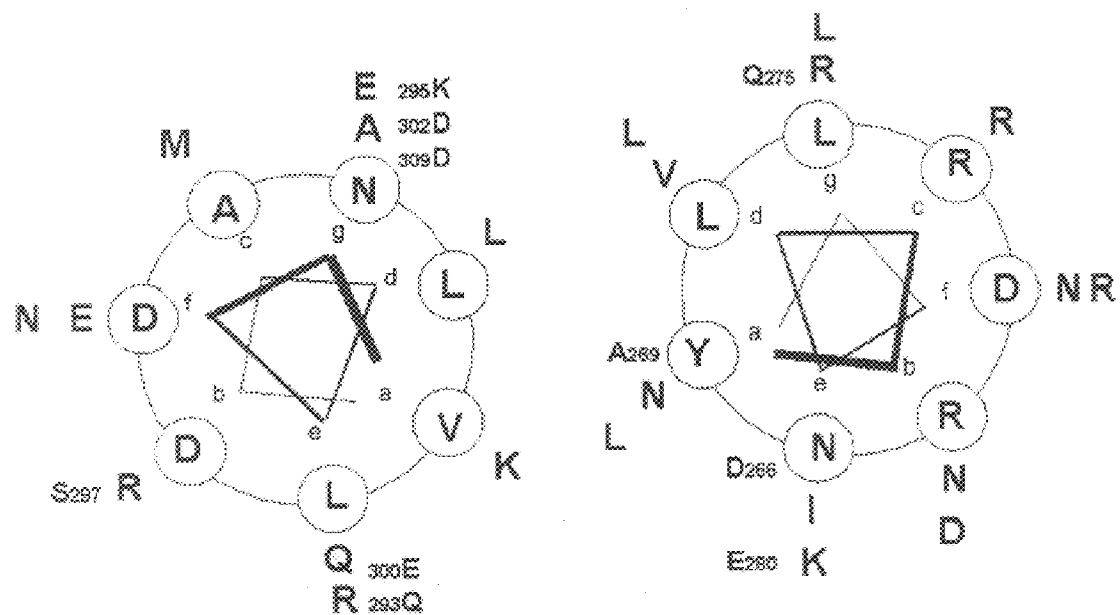
FIG. 3B. Helical wheel drawing of predicted β'$_{260-309}$ coiled coil. The two predicted helices are shown as interacting with one another to form an antiparallel coiled coil. Mutations are sown next to original residues along with the residue number. The N-terminus is at amino acid N266 on the right helix. This helix is depicted as coming out of the page, while the left helix is going into the page and terminates at N309.

The Coils prediction program (Lupas et al., 1991) scored both of the predicted α-helices of β'$_{260-309}$ as having a high probability of forming coiled coils (FIG. 3a). To test this prediction two β' mutants were constructed with proline residues inserted into either helix. These β' mutants were no longer predicted to form helices or coiled coils. When assayed for function in both the far-Western and in vivo growth assays, both mutants were found to be nonfunctional. This indicated that the helical/coiled coil structure in this region was important for function. However, the solubility of these mutant proteins was not 100%, so their loss of function could simply be due to gross folding defects. Further analyses were directed for the most part on the "e" and "g" positions of the helices. The e and g residues of coiled coils often engage in interhelical interactions such as the formation of ionic interactions or salt bridges (Cohen et al., 1986; Chao et al., 1998). Such interactions in this case could be intramolecular (between the two helices of $\sigma'_{260-309}$) forming a coiled coil structure necessary for binding by the σ subunit (FIG. 3b). Alternatively, the e and g residues of β'$_{260-309}$ could be making intermolecular contacts with helices of σ upon binding. Change-of-charge mutations were prepared at these residues of β' and the effect of the mutation on binding determined (FIG. 3b). Two of the mutations described do not involve e or g residues. Based on the findings that tyrosine and arginine residues are often located in "hot spots" of protein-protein interactions (Bogan et al., 1998), the tyrosine residue at position 269 was changed to an alanine and the arginine residue at position 297 to a serine. It had been determined that insertion of a leucine at position 297 generated a β' subunit that was nonfunctional for binding $\sigma^{70}$ (data not shown). Therefore, it was of interest to determine if a less drastic mutation at this position would also affect σ binding. Several of the mutations in the β'$_{260-319}$ region disrupt interaction with $\sigma^{70}$ in a far-Western assay.

Far-Western blotting had been used to map a $\sigma_{70}$ binding site to the N-terminal region of the β' subunit (Example 2). This method was initially employed to detect the functionality of the β' mutants. The mutations were cloned into a gene fragment coding for amino acid residues 1–319 of the β' subunit. Cells containing these genes were induced for a short period to give moderate levels of the β' fragment, comparable to other proteins in the extract. Samples were analyzed for binding $\sigma^{70}$ by far Western analysis The amount of $\sigma^{70}$ probe bound by each β'$_{1-319}$ mutant fragment was compared to the amount bound by wt β'$_{1-319}$ fragment. Each signal was normalized to the amount of β'$_{1-319}$ contained in the supernatant as determined by Western blotting.

Five of the mutations (R275Q, R293Q, E295K, R297S, and A302D) were greatly reduced in their ability to bind $\sigma^{70}$ (FIG. 4). The Q300E and N309D mutations had the opposite effect, binding more $\sigma^{70}$ than wild type β'$_{1-319}$. Q300E exhibited an increase in relative binding of greater than 7-fold. There were no effects on binding seen with the N266D, Y269A, or K280E mutations.

Growth with Mutant β'

To assess the importance of the $\sigma^{70}$ binding site in vivo, the ability of mutant β' subunits to function as the cell's sole source of β' was assessed. Plasmids containing either mutant or wild type, full length β' were transformed into strain RL602 (Weilbaecher et al., 1994; Ridley et al., 1982). The chromosomal rpoC gene of RL602 has an amber mutation that prevents functional β' from being produced in the absence of a suppressor tRNA. RL602 also has a chromosomal, temperature-sensitive, amber suppressor. At the permissive temperature (30° C.) the amber suppressor is active and allows chromosomal β' to be produced and the cell can grow. The amber suppressor is not active at the non-permissive temperature (42° C.). Therefore, at 42° C., chromosomal β' is not made and the cell cannot grow without another source of β'. If the plasmid-derived β' can complement the loss of β', the cells will grow and form colonies on plates at the non-permissive temperature. If the mutant β' cannot complement, there will be no growth on the plates at this temperature.

Figure 5:
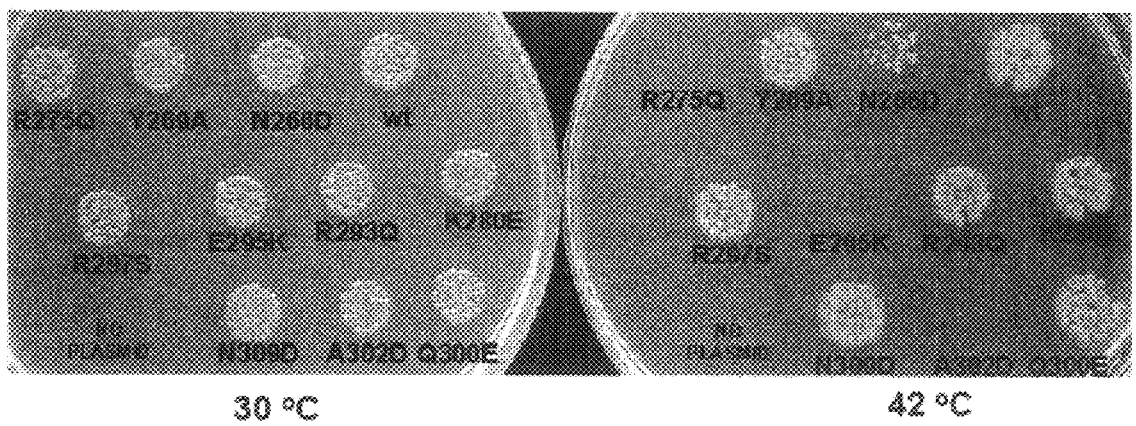
FIG. 5. Growth with plasmid-derived wild type or mutant β' as the sole source of β' subunit. Strain RL602 was transformed with a plasmid encoding either wild type or mutant, full length β'. Transformed cells (10 μl) were then spotted onto duplicate plates, incubated at either 30° C. (permissive) or 42° C. (nonpermissive) for 24–48 hours, and then assessed for growth.

Three of the mutations that were defective for σ binding in the far-Western assay (R275Q, E295K, and A302D) could not support growth at the non-permissive temperature, indicating that these mutations were also defective in binding σ in vivo (FIG. 5). N266D, a mutation that had no detectable effect in the far-Western assay, allowed some growth at the non-permissive temperature but not enough to be considered wild type. In contrast, the R293Q and R297S mutations that did not bind $\sigma^{70}$ in the far-Western assay could support growth in vivo. Other mutations (Y269A, K280E, Q300E, and N309D) had no detectable effects on growth. Expression levels for nonfunctional β' mutants were determined to be equivalent to that of plasmid-derived, wild type β' when grown at 37° C. (data not shown).

Core/Holo Assembly

To evaluate the potential assembly defects caused by the various mutations, His$_6$-tagged, mutant β' subunits were expressed in cells that were also expressing wild type, chromosomal β' proteins. A Ni$^{2+}$-NTA column was used to purify the mutant β' subunits together with associated cell proteins. An immunoaffinity column was used to clean-up the samples in order to reduce any non-specific binding to the Ni$^{2+}$-NTA column.

Figure 6A:
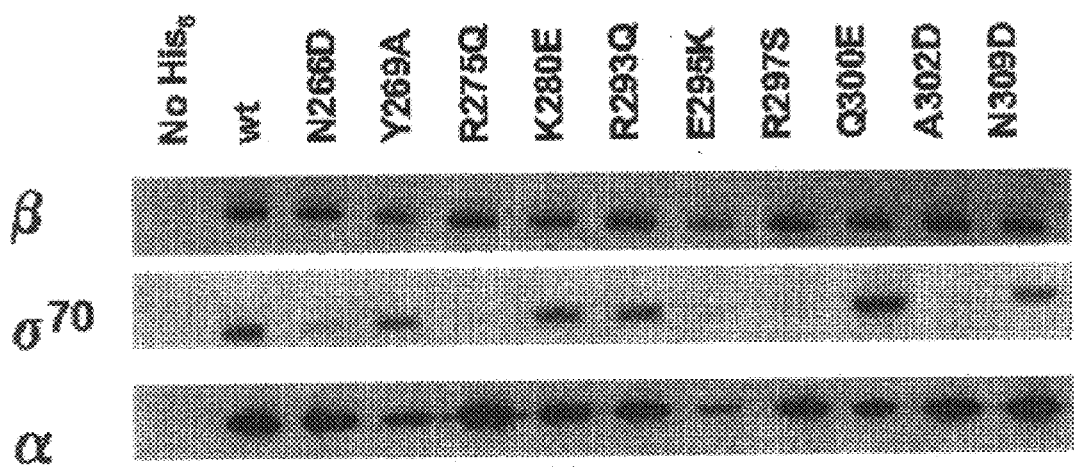
FIG. 6A. Assembly of core and/or holoenzyme in log phase samples. Cells grown with wild type or mutant β' expression plasmids were harvested and subjected to purification to isolate the plasmid-derived His$_6$-tagged β' and any of its assembled complexes. Proteins from Ni$^{2+}$-NTA purified samples were separated via SDS-PAGE and blotted to nitrocellulose. The blots were then probed with monoclonal antibodies (MAbs) against the indicated subunits. No His$_6$: strain expressing plasmid-derived, wild type β' without a hexahistidine tag. Results are the average of three different experiments. Error bars represent standard deviation.
Figure 6B:
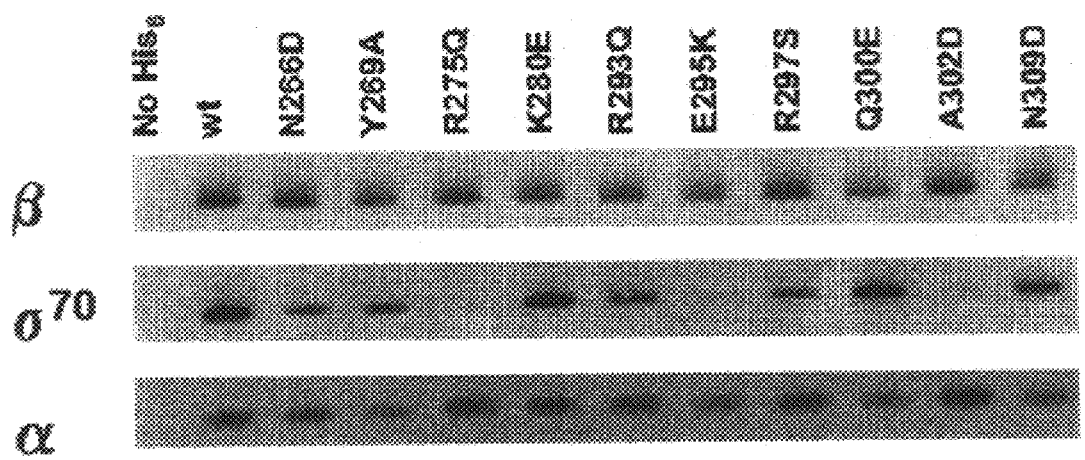
FIG. 6B. Assembly of core and/or holoenzyme in stationary phase samples Cells grown with wild type or mutant β' expression plasmids were harvested and subjected to purification to isolate the plasmid-derived His$_6$-tagged β' and any of its assembled complexes. Proteins from Ni$^{2+}$-NTA purified samples were separated via SDS-PAGE and blotted to nitrocellulose. The blots were then probed with monoclonal antibodies (MAbs) against the indicated subunits. No His$_6$: strain expressing plasmid-derived, wild type β' without a hexahistidine tag. Results are the average of three different experiments. Error bars represent standard deviation.

All of the mutant β'subunits tested retained the ability to assemble into the core enzyme demonstrated by the association of the α and β subunits throughout the purification (FIGS. 6a and 6b). Again, mutations R275Q, E295K, and A302D caused defects in binding $\sigma^{70}$ in both log and stationary phase samples. Also reduced in E$\sigma^{70}$ formation were N266D in both log and stationary phase samples and R297S in log phase samples. Q300E again showed properties of binding $\sigma^{70}$ better than wild type. Y269A, K280E, R293Q, and N309D had no detectable affect on E$\sigma^{70}$ assembly. When a non-His$_6$ tagged β' was expressed from the plasmid, there was no detectable nonspecific binding to the Ni$^{2+}$-NTA column.

All of the sample eluates were also assayed for the presence of any minor σ species. The only minor σ's whose concentrations were sufficient for detection were $\sigma^{32}$ in log phase and $\sigma^{32}$ and $\sigma^F$ in stationary phase samples. The results for these σ's were essentially the same as for $\sigma^{70}$ with the exception of mutants R297S and Q300E. In stationary phase samples from the Q300E mutant the $\sigma^{32}$ and $\sigma^F$ levels are greatly reduced while the $\sigma^{70}$ levels are above wild type. The log phase samples for this mutant also contained a decreased amount of $\sigma^{32}$, indicating a defect in E$\sigma^{32}$ formation but not as severe as in stationary phase.

Molecular Modeling

Figure 8B:
FIG. 8B. View of mutations modeled onto the crystal structure of T. aquaticus RNA polymerase (Zhang et al., 1999) using Rasmol software program (Sayle et al., 1995). View is down the center of coiled coil toward polymerase. The mutations that were defective in all assays tested are colored green. Mutations that were defective in some assays, but not all, are colored cyan. Mutations that were always functional are colored purple. "Rudder", colored maroon, is added to orient the structure.
Figure 8C:
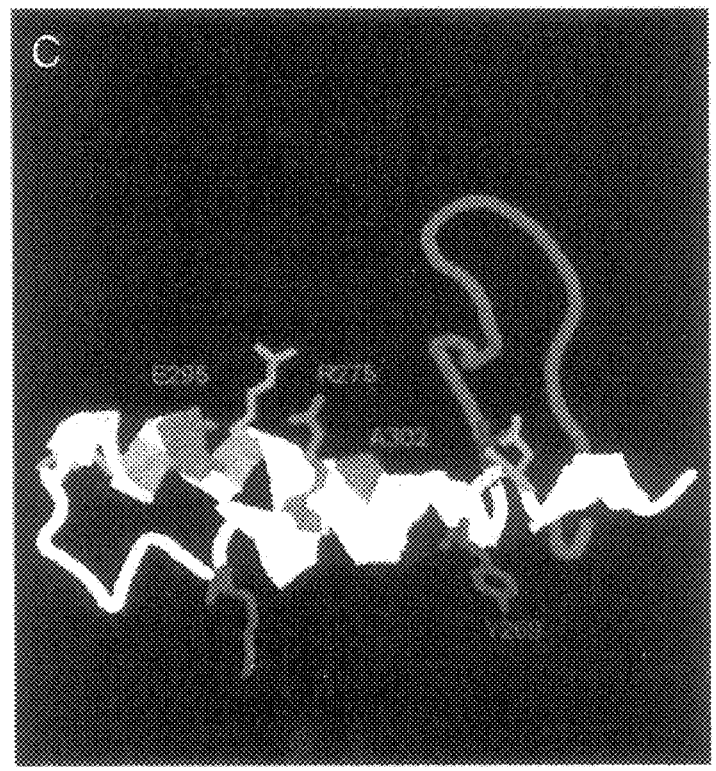
FIG. 8C. View of mutations modeled onto the crystal structure of T. aquaticus RNA polymerase (Zhang et al., 1999) using Rasmol software program (Sayle et al., 1995). View is side view of coiled coil. The mutations that were defective in all assays tested are colored green. Mutations that were defective in some assays, but not all, are colored cyan. Mutations that were always functional are colored purple. "Rudder", colored maroon, is added to orient the structure.
Figure 9:
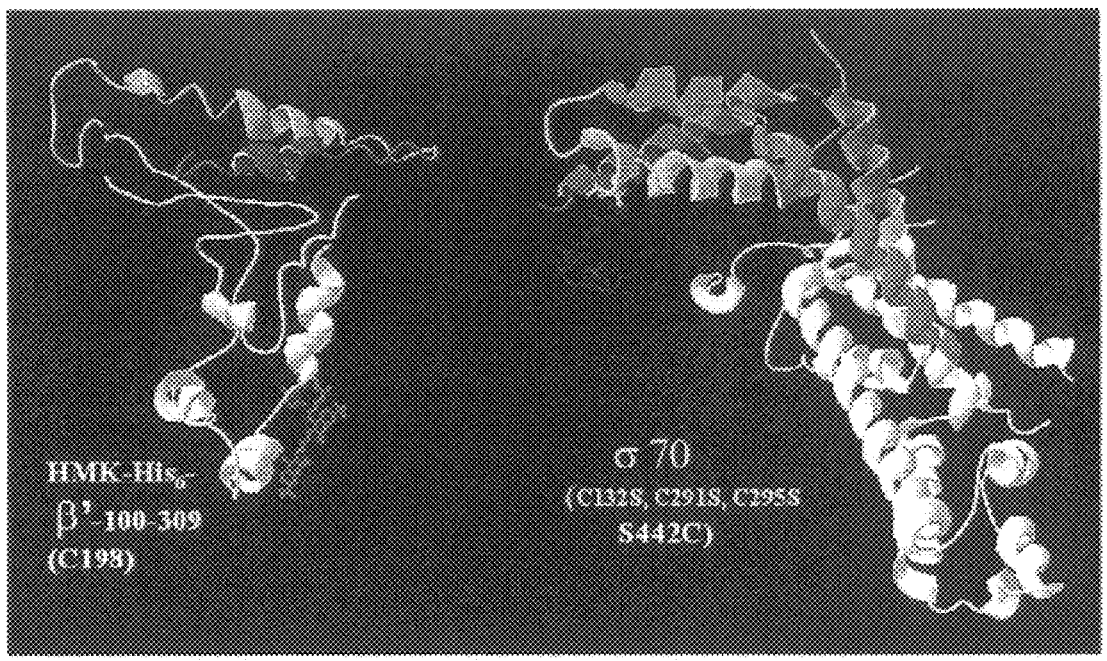
FIG. 9. The structures of σ$^{70}$ and the β'-fragment used in the protein binding assay described in Example 4 are shown. Next to the names are the mutations and in bold letters the derivatization sites, respectively. HMK-His$_6$-β'-100–309 is a fragment of β' which contains residues 100–309 and is a N-terminal fusion to a heart-muscle kinase (HMK) recognition site and a His$_6$-tag. The coiled coil α-helical structure colored magenta in the β'-fragment is likely the main G binding element in the RNAP. IC5 is colored in pink. The regions in σ$^{70}$ responsible for binding to core RNAP are regions 2.1 (green) and 2.2 (yellow). Also indicated by color are regions 2.3 (blue), 2.4 (brown), the non-conserved region (white) and the N-terminus (red) of the σ$^{70}$-structure. The Eu-DTPA-AMCA complex is colored in dark blue.

Recently, Zhang et al. (1999) published the crystal structure of *T. aquaticus* RNA polymerase. The β'$_{260-309}$ region of *E. coli* RNA polymerase has a high degree of sequence conservation with its *T. aquaticus* homolog (FIG. 8a). This region of the *T. aquaticus* β' subunit forms a "coiled coil-like" structure. When the mutations studied herein are modeled onto the *T. aquaticus* structure using the Rasmol software program (Sayle et al., 1998), those that are most defective in σ binding are grouped on one face of the coiled coil. Those that had defective phenotypes in some assays but not others are on the outer edges of this face. Mutations that had no detectable effects are clustered on the opposite face of the coiled coil with the exception of N309D which is located at the very C terminus of the coiled coil immediately next to the "rudder" (FIGS. 8b and 8c).

Discussion

Binding of various σ factors to the core polymerase is a major step in the process of global gene expression and regulation. It is not known if this step is part of the regulation, via a competition for binding to a limited core population, or merely a straight-forward binding of free σ's to an excess of core. If there is competition among populations of σ species for core binding, that competition may be influenced by binding specificity of the σ's. In light of the high sequence conservation of most σ species, it has been hypothesized that all σ factors bind to the same locations on the core enzyme (Helmann et al., 1988). As described herein, the in vivo binding site on β' of RNA polymerase for $\sigma^{70}$ was identified. Moreover, this binding site is also involved in binding at least some of the minor σ factors. Further, the methods, compositions and compounds described herein are useful to identify important residues in core RNA polymerase for σ binding, and to define a potential binding interface for the σ-core interaction.

The mutational analysis approach, which was designed to look for loss of $\sigma^{70}$ binding by targeting residues of the 260–309 region of the β' subunit that were identified as occupying e or g positions in the predicted coiled coil structure, resulted in three classes of mutations: nonfunctional for σ binding in all assays tested; nonfunctional in some assays but not others; and those that were functional in all assays tested. The first group contains mutations R275Q, E295K, A302D. These three mutations were nonfunctional for $\sigma^{70}$ binding in vitro and in vivo, indicating that they play a very important role in binding $\sigma^{70}$. Arginine 275 is located near the C terminus of the first of the two putative helices while glutamate 295 and alanine 302 are in the middle and near the C terminus of the second helix, respectively. This confirms that both predicted helices of β'$_{260-309}$ were involved in binding $\sigma^{70}$. The mutations made at these residues were the only ones tested that could not support any detectable growth when the expression of the chromosomal β' subunit was turned off. This is significant in light of the fact that these mutant β' subunits, along with all those tested in this study, had no detectable defect in interactions with the α and β subunits necessary to form the core enzyme. Thus, there are no gross folding defects that are responsible for the lack of $\sigma^{70}$ binding.

It is possible that the local structure of these mutant proteins is disturbed. Sequence analysis of all 10 mutant subunits predicted no change in secondary structures as compared to the wild type protein (Rost et al., 1994; Munoz et al., 1994). The A302D change would be the most likely, though, of the three group 1 mutations to be disturbing the local structure. This introduces a bulky charged side chain in place of a single methyl group. Also, based on the crystal structure of the *T. aquaticus* core RNA polymerase (Zhang et al., 1999), the A302 α carbon is directed more toward the opposite helix of the coiled coil than are the side chains of R275 or E295 which are solvent exposed. If R275Q and E295K are not affecting the local β' structure then most likely the negative $\sigma^{70}$ binding properties are coming from stearic hindrance, charge repulsion, or loss of a specific interaction with the σ subunit.

The group 2 mutants, N266D, R293Q, and R297S, are of particular interest since they seem to have some function depending on the assay in which they are analyzed. R293Q and R297S were not functional for in vitro $\sigma^{70}$ binding in far Western assays but could support growth and were able to form core enzymes that were capable of binding $\sigma^{70}$, although R297S does cause a decrease in the binding efficiency of the mutant core enzyme in log phase. The differences in the in vivo and in vitro assay results for these mutants can be explained in multiple ways. First, a positive result from the far Western assay requires that a β' fragment (1–319) refold the secondary structure needed to bind $\sigma^{70}$ while part of the protein is immobilized on a membrane. Therefore, mutations found to cause defects may be introducing in vitro folding deficiencies. Secondly, the in vivo assays are analyzing σ binding to the multisubunit core enzyme and not just an individual subunit or fragment. A great deal of evidence has been reported suggesting multiple binding sites on core RNA polymerase for the σ factor (Sharp et al., 1999: Joo et al., 1998; Nagai et al., 1997; Owens et al., 1998). Thus, loss of one of those sites may be compensated for by the remaining binding interactions. While R293Q and R297S mutations are disrupting σ binding to $\beta'_{260-309}$, they are not obstructing $\sigma^{70}$ from making its other contacts on core polymerase.

In contrast to the previous group 2 mutations, N266D had no effect on $\sigma^{70}$ binding to β', but caused reductions in E$\sigma^{70}$ formation comparable to group 1 mutations and had a weak growth deficiency. N266 is located at the base of the coiled coil and when mutated could change the local structure. This change may be causing a shift in the orientation of the coiled coil with respect to the rest of the core enzyme. This would not affect the binding of $\sigma^{70}$ to the coiled coil but may disrupt other contacts normally made by $\sigma^{70}$ with core.

The group 3 mutants, Y269A, K280E, Q300E, and N309D, were all fully functional indicating that these residues are not making critical contacts with $\sigma^{70}$. The Q300E change was rather interesting. This mutation seems to cause an increase in binding of $\sigma^{70}$ to β'. The large increase in relative binding seen in the far Western was not as dramatic in vivo possibly due to the $\sigma^{70}$-core interaction having a larger Keq than the $\sigma^{70}$-β' interaction. Although, the assembly of E$\sigma^{70}$ for this mutant still was almost twice that of wild type. Inhibitors based on coiled coil interactions have proven to be useful in disrupting such processes as viral entry into cells and topoisomerase activity (Eckert et al., 1999; Wild et al., 1994; Frere-Gallois et al., 1997). Inhibitors of the σ-core interaction may be useful as antibacterial therapeutics. In particular, the Q300E mutation may provide useful information on increasing the binding constant of such an inhibitor.

The alternative σ factors have been thought to bind to the same sites on core RNA polymerase as $\sigma^{70}$. Mutating conserved residues of different σ species will disrupt core binding (Sharp et al., 1999). Traviglia et al. (1999) used tethered Fe-EDTA cleavage to determine that several of the minor σ species of *E. coli* are in close proximity to the same regions of core RNA polymerase as $\sigma^{70}$ within the Eσ complex. At least for $\sigma^{32}$ and $\sigma^{F}$, minor σ factors do bind one of the same sites on core as $\sigma^{70}$. Though they are binding to the same site, there is some difference in the manner of binding. The Q300E mutation that increased binding of $\sigma^{70}$ had the opposite effect, especially in stationary phase, on $\sigma^{32}$ and $\sigma^{F}$. R297S also had different binding properties for the σ factors. This mutation caused an increased binding of the minor sigmas and reduced binding of $\sigma^{70}$. It is interesting that these mutations both had opposing effects on $\sigma^{70}$ and the minor σ's, although only two minor σ's were at detectable levels. This suggests that changes in the local environment could favor or hinder minor σ binding as a whole as compared to $\sigma^{70}$.

Finally, the crystal structure of *T. aquaticus* core RNA polymerase has been of great utility in trying to understand the results of the mutations. Based on the computer predictions and the mutational results described herein, it could not have been concluded that $\beta'_{260-309}$ formed a coiled coil structure. However, combining this information with the *T. aquaticus* versus *E. coli* β' sequence alignment and the *T. aquaticus* crystal structure, it is clear that $\beta'_{260-309}$ adopts a coiled coil conformation. Upon σ binding though, it is not clear what structure this region takes on. Conserved region 2.1 of $\sigma^{70}$, implicated in core binding (Lesley et al., 1989), forms a coiled coil with region 1.2 in the crystal structure of the $\sigma^{70}$ protease-resistant domain (Malhotra et al., 1996). Also, a predicted coiled coil in $\sigma^{54}$ of *E. coli* has been found to be important in the σ-core interaction (Hsieh et al., 1999). These σ factor structures may be interacting with $\beta'_{260-309}$ to form a four helix coiled coil. It is also known that the σ factor undergoes a conformational change upon binding core (Nagai et al., 1997; Callaci et al., 1998; McMahan et al., 1999). This may be caused by a rearrangement of the coiled coils to form new contacts (Grum et al., 1999; El-Kettani et al., 1996).

From the clustering of the group 1 mutations on the same face of the coiled coil structure while having the group 2 mutations on the edges of the cluster and the group 3 members on the opposite side of the coiled coil, the binding interface for $\sigma^{70}$ on β' has been defined. Recent work has localized the region of $\sigma^{70}$ that is interacting with $\beta'_{260-309}$ to a peptide containing a portion of the nonconserved region and region 2.1–2.2 of the $\sigma^{70}$ subunit (Burgess et al., 1998). β' region 198–237 was identified by Brodolin et al. (2000) as interacting with the nontemplate strand of the lacUV5 promoter which also is known to be contacted by region 2.4 of $\sigma^{70}$ (Siegele et al., 1989; Waldburger et al., 1990).

EXAMPLE 4

Luminescence Resonance Energy Transfer (LRET) to Monitor $\sigma^{70}$ to Core RNA Polymerase Interactions The bacterial transcription machinery appears to offer an attractive target for drug discovery and drug design as it is highly conserved among the bacterial kingdom, but significantly different from eucaryotes. Any inhibitor of the assembly of a sigma factor with core RNAP to form the holoenzyme would inhibit the initiation of transcription in general and therefore prevent growth and eventually survival of a cell. The postulated region mainly responsible for core binding (region 2.1–2.2, FIG. 20) of bacterial transcription factors ($\sigma^{70}$ in *E. coli*) shows a remarkably high identity (>80%) and is also highly similar among the minor sigma factors of bacteria (Lesley and Burgess, 1989; Lonetto et al., 1998). Additionally, β' (FIG. 20) in core RNAP exhibits a very high sequence conservation in the sigma-binding region (between residues 260–309 in β' of *E. coli*) (Arthur et al., 2000; Arthur and Burgess, 1998). These homologies suggest a highly conserved structure within the holo form of RNAP, whose formation is crucial for correct initiation of transcription. Any inhibitor of this interaction can thus be expected to be a broad spectrum antibiotic. No $\sigma^{70}$ homolog has been found in mammalian cells except for sigma factors in mitochondria (Tracy and Stern, 1995) and chloroplasts (Allison, 2000), however, they do not show a significant homology to their prokaryotic counterparts. This fact implies that there is very little chance of a potential new antibiotic interfering with eukaryotic RNA polymerase assembly, which could otherwise lead to serious side effects, if it were used as a drug.

In order to screen for inhibitors of RNAP assembly with σ, a simple, fast and reliable assay is needed for the formation of the $\sigma^{70}$-β'-complex. Electrophoretic mobility shift (EMS) assays and far-Western blots were shown to be very helpful in identifying the binding regions within *E. coli* RNAP (Burgess et al., 2000), but for a potential high-throughput screen a more rapid and preferably homogenous assay with a very sensitive signal-to-noise ratio would be desirable. A fluorescence-based probe assay was chosen to monitor complex formation. In this respect FRET (Fluorescence Resonance Energy Transfer) offers a system that can create the desired signal upon complex formation (Selvin, 1995; Selvin, 2000; Stryer, 1978). FRET occurs when two appropriate dyes get into proximity of less than about 75 A depending on their spectral properties. The energy transfer between these dyes is transmitted via dipole-dipole interactions. The acceptor is thereby sensitized and can now fluoresce with its peculiar wavelength. Both emissions have different wavelengths and can be monitored separately. This can give information about amount of and distance between the two dyes. A quantitative description of the effect is based on the Förster theory that describes the decrease of energy transfer as inversely proportional to sixth-power of the distance between the two dyes. Hence, the energy transfer and thereby the distance between the dyes can be determined by measuring the intensity of the emissions and their decay.

LRET (Luminescence Resonance Energy Transfer) is a modified version of this effect (Selvin, 1999). Different from FRET, the donor is an organic dye coupled to a lanthanide complex. This difference offers advantageous spectroscopic features. A large stokes shift (distance between excitation and emission wavelength) avoids a strong cross talk between the instrumental excitation source and the emission. Narrow emission lines allow an accurate separation of donor and acceptor signal. The lifetime of most lanthanides like Eu and Tb are significantly longer (milliseconds) than the vast majority of the commonly used organic dyes like Cy5 (nanoseconds). Measuring in time-resolved fluorescence mode allows one to start signal acquisition after the background fluorescence and the intrinsic acceptor fluorescence have decayed. Thus, only the donor-sensitized emission of the acceptor can be measured which leads to a very good signal-to-noise ratio. The two dyes used in the assay are shown in FIG. 10.

Figure 11:
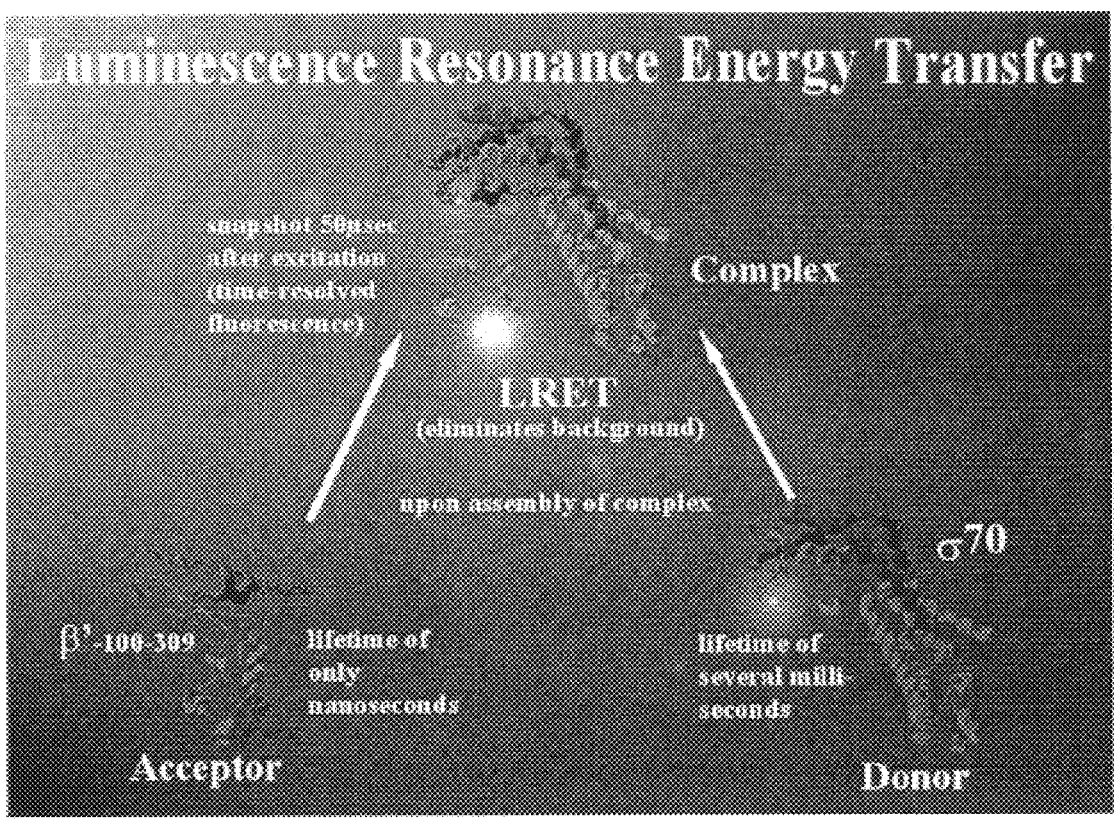
FIG. 11. A schematic showing how the LRET signal is created upon binding of the labeled proteins β'-100–309 and σ$^{70}$. The fluorescence of the IC5-labeled β'-fragment decays during the delay of the data acquisition 50 microseconds after excitation at 320 nm. Only the Eu-emission of labeled σ$^{70}$ and the sensitized IC5 emission in the complex can be observed after the delay due to the long Eu-luminescence of over 1 milliseconds. This minimizes the background signal and yields in a favorable signal-to-noise ratio that is desired in an efficient high-throughput screening assay.

Heyduk and co-workers have used LRET to measure DNA binding to $\sigma^{70}$ in holoenzyme using the same pair of dyes (Heyduk and Heyduk, 1999). For the assay described hereinbelow, an IC5-labeled β'-fragment (residues 100–309 N-terminally fused to a heart-muscle kinase (HMK) recognition site and a His$_6$-Tag) was substituted for the Cy5-labeled polynucleotide. For the resulting homogenous assay, $\sigma^{70}$ was labeled with a Europium-DTPA-AMCA complex as a donor and the HMK-His$_6$-β'(100–309)-fragment with the Cy5-analogue IC5-maleimide (Dojindo, Japan). FIG. 11 illustrates the assay. Upon complex formation, LRET occurs. Complex formation between $\sigma^{70}$ and β' is monitored simply by looking at the delayed emission of the acceptor as an optically measurable signal of complex formation. The assay can be performed in a multi-well plate and measured by a multi-plate reader to accomplish a high-throughput of a large number of samples from any chemical library in an automated way. Typical reaction volumes are 10–200 μL where the components including the test substances are mixed directly in the multi-well plate before the plate is measured in the reading device. The very sensitive nature of such a fluorescence-based assay (typically in the low nanomolar range) provides good accuracy and signal-to-noise ratio, avoiding false positive hits in the measurement. It also permits a low usage of labeled protein and substrates, which cuts down on overall costs.

Methods

Buffers

The following buffers were used: NTGED-Buffer (50 mM NaCl, 50 mM Tris-HCl, pH 7.9, 5% glycerol, 0.1 mM EDTA, 0.1 mM DDT); TGE-Buffer (50 mM Tris-HCl, pH 7.9, 5% glycerol, 0.1 mM EDTA); NTG-buffer=FRET-Buffer (50 mM NaCl, 50 mM Tris-HCl, pH 7.9, 5% glycerol); TNTwGu-buffer (50 mM Tris-HCl, pH 7.9, 500 mM NaCl, 0.1 v/v % Tween 20, 6 M Gu-HCl); Native Sample-buffer (200 mM Tris-HCl, pH 8.8, 20 v/v % glycerol, 0.005% bromphenol blue); and Storage-Buffer (50 mM NaCl, 50 mM Tris-HCl, pH 7.9, 50% glycerol, 0.5 mM EDTA, 0.1 mM DDT).

Overproduction of HMK-His$_6$-β'(100–309) and $\sigma^{70}$ (C132S, C291S, C295S S442C)

Figure 12:
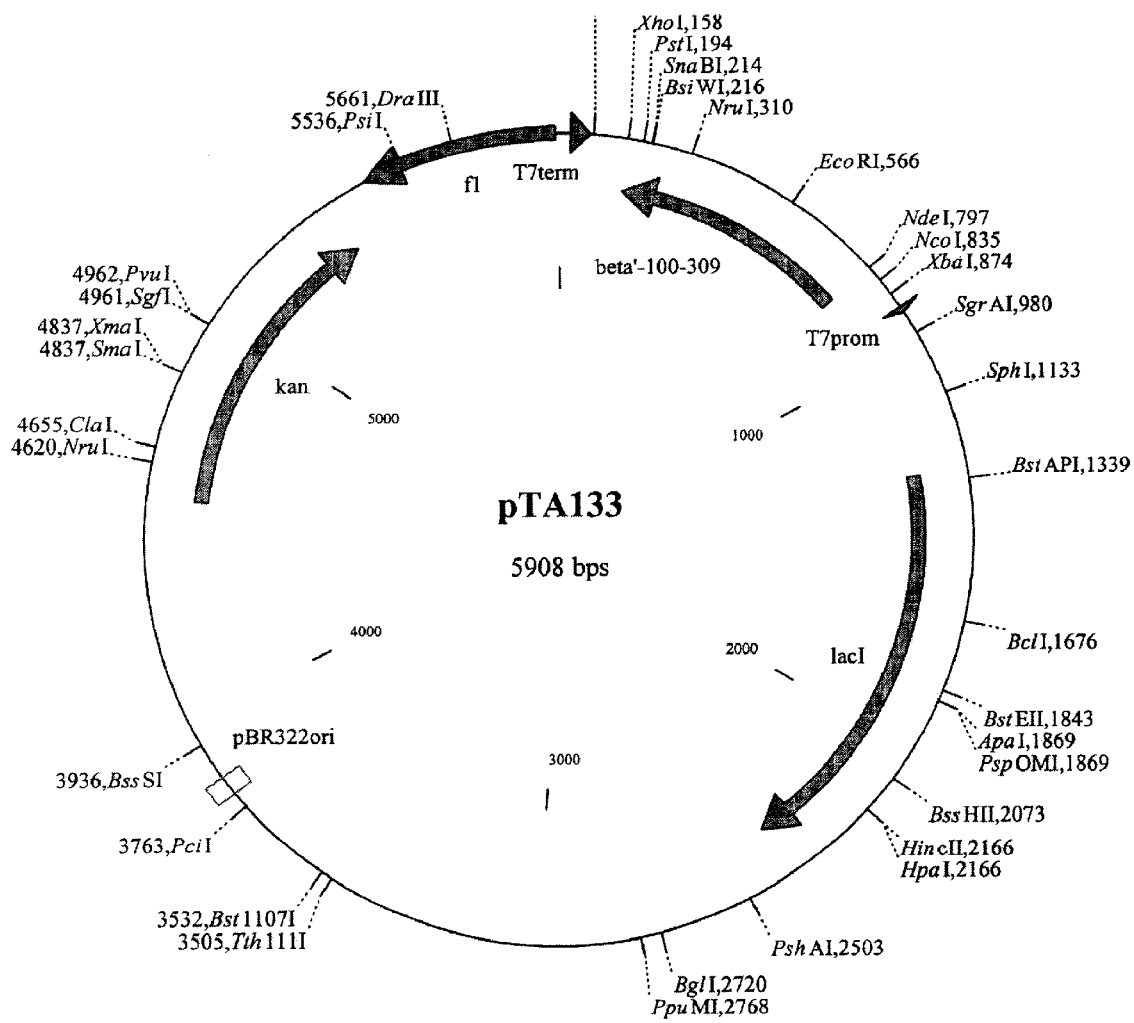
FIG. 12. Map of the plasmid pTA133. The plasmid pTA133 is derived from the expression vector pET28b(+) (Novagen). An N-terminal HMK-site and the His$_6$-tag encoding sequence were inserted together with the β'-region 100–309. The plasmid carries a pBR322 origin of replication for cloning in E. coli and a kanamycin resistance gene for selection. The lacI repressor gene is included for tight control of induction via IPTG.

The plasmid pTA133 (Arthur and Burgess, 1998; FIG. 12) is a derivative of the expression vector pET28b(+). First a HMK-site was inserted into the 5'-start of the MCS, then the partial β' sequence was cloned into the resulting vector to yield a chimera (25 kDa) with the amino acid sequence MA <u>RRASV</u>HHHHHHM-terminally fused to β'(100–309). The HMK recognition site is underlined.

Figure 13:
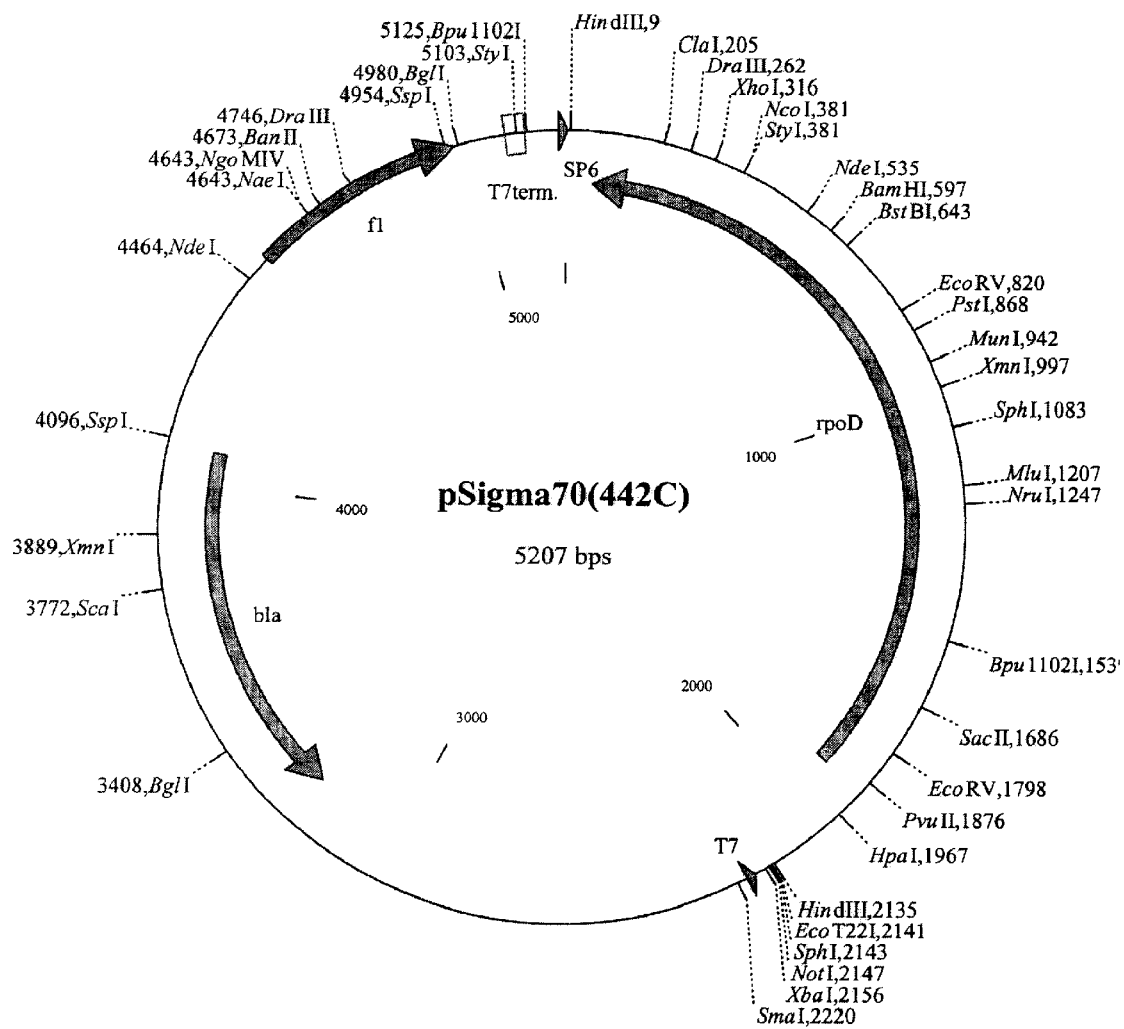
FIG. 13. Plasmid map of the expression plasmid pSigma70(442C). The plasmid is derived from pGEMX-1 (Promega) and allows expression under a T7 expression system with ampicillin selection.

Plasmid pSigma70(442C) (Heyduk and Heyduk, 1999; FIG. 13) is derived from the $\sigma^{70}$-expression system pGEMD (Igarashi and Ishihama, 1991; Nakamura, 1980) that had a HindIII fragment containing the rpoD gene from *E. coli* cloned into a pGEMX-1 (Promega) vector. It is a T7 expression system allowing controlled induction by IPTG and selection with ampicillin. The plasmids were transformed into BL21(DE3) (Novagen) for expression. The cells were grown in 1 L cultures at 37° C. in LB medium with 100 μg/ml ampicillin. The cultures were grown to an OD$_{600}$ between 0.5–0.7 and then induced with 0.5 mM isopropyl β-D-thiogalactoside (IPTG). Two hours after induction, the cells were harvested by centrifugation at 8,000×g for 15 minutes and frozen at −20° C. until use.

Purification of Inclusion Bodies

Figure 14:
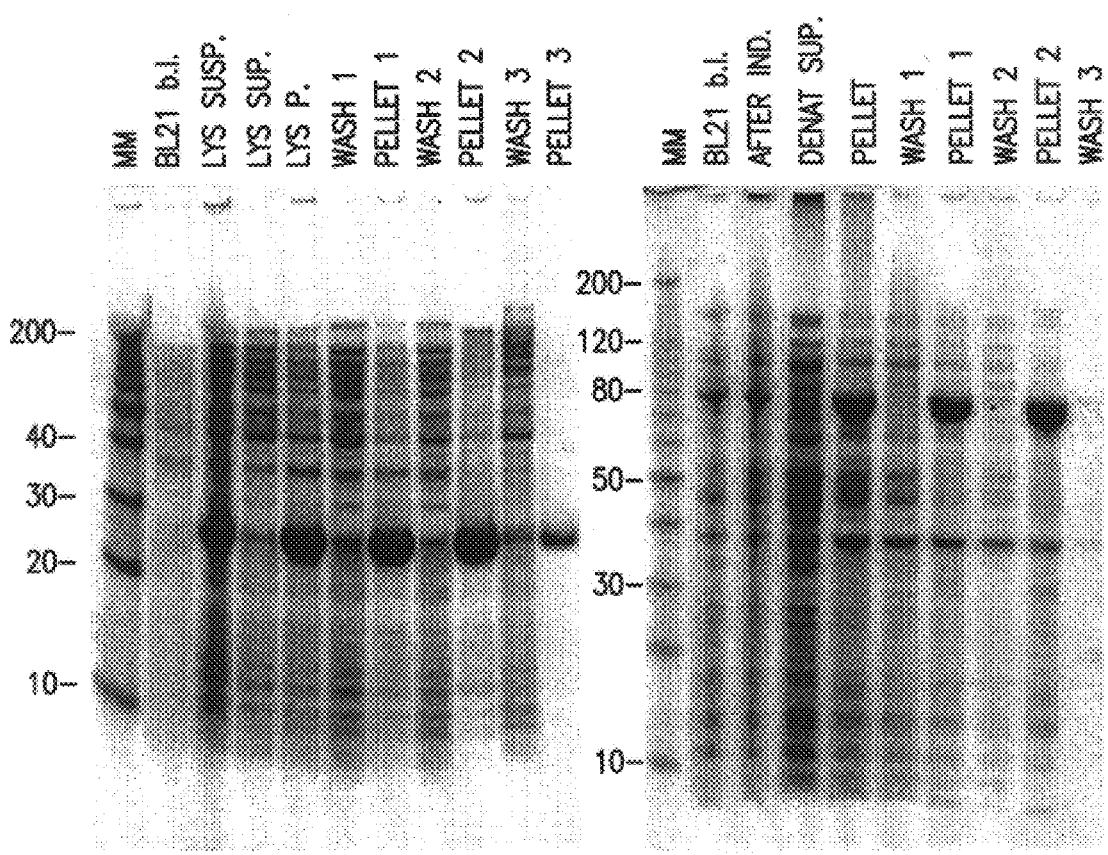
FIG. 14. SDS-PAGE gels of inclusion-body purification for β'-fragment (left) and σ$^{70}$ (right). Gels were stained with GELCODE (Pierce) Coomassie Blue. Both gels were NuPAGE (NOVEX), with 12% polyacrylamide (left gel) and a gradient of 4–12% polyacrylamide (right gel).

A cell pellet (1–2 g wet weight) was resuspended in 10 mL NTGED-buffer+10 mM EDTA and 100 μg/ml lysozyme. The cells were incubated on ice for 30 minutes then sonicated three times in 60 second bursts at 4° C. Triton X-100 (1% v/v) was added and vortexed. The recombinant protein in the form of inclusion bodies was separated from the soluble lysate by centrifugation at 25,000×g for 15 minutes. At each step, a 100 μL sample was taken for SDS-PAGE, which is shown in FIG. 14. The inclusion body pellet was resuspended, by sonication, in 10 ml NTGED-buffer+1% (v/v) Triton X-100. The mixture was centrifuged at 25,000×g for 15 minutes and the supernatant discarded. The washed inclusion bodies were resuspended in 10 ml NTGED-buffer+0.1% (v/v) Triton X-100 and centrifuged at 25,000×g for 15 minutes. The wash was repeated with 10 ml NTGED-buffer+0.01% (v/v) Triton X-100 and the suspension of inclusion bodies was aliquoted into 5 equal portions in 2 mL vials prior to centrifugation in a Beckman Microfuge® 18 centrifuge at maximum speed. Supernatants were removed by pipetting and inclusion bodies were frozen at −20° C. until use.

Ni-NTA Purification and IC5-derivatization of the β'-fragment

Figure 15:
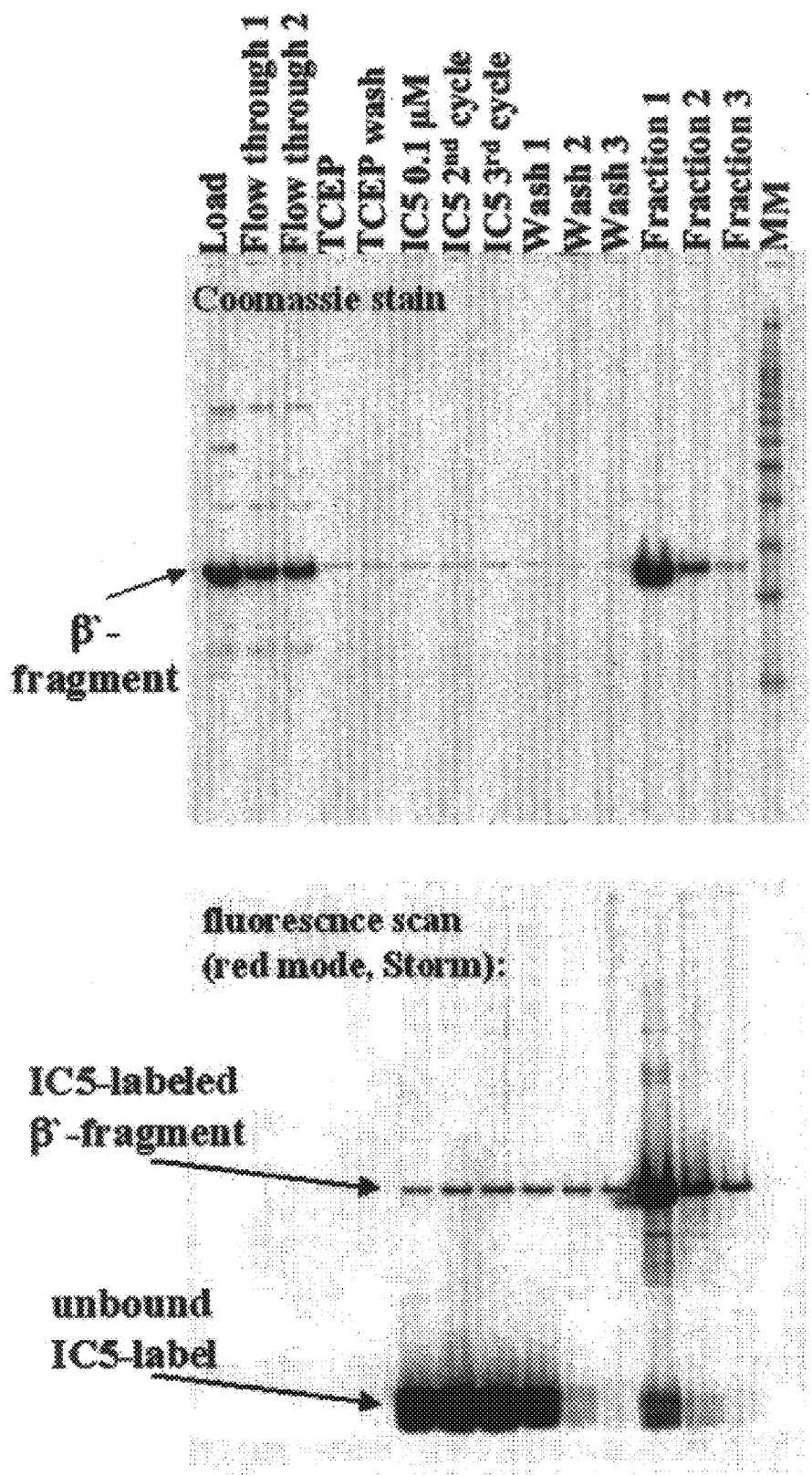
FIG. 15. SDS-PAGE gel of the β'-purification and derivatization steps (Coomassie stain and IC5 scan). The IC5-scan was performed with a Molecular Dynamics Storm system in the red fluorescence mode.
Figure 16:
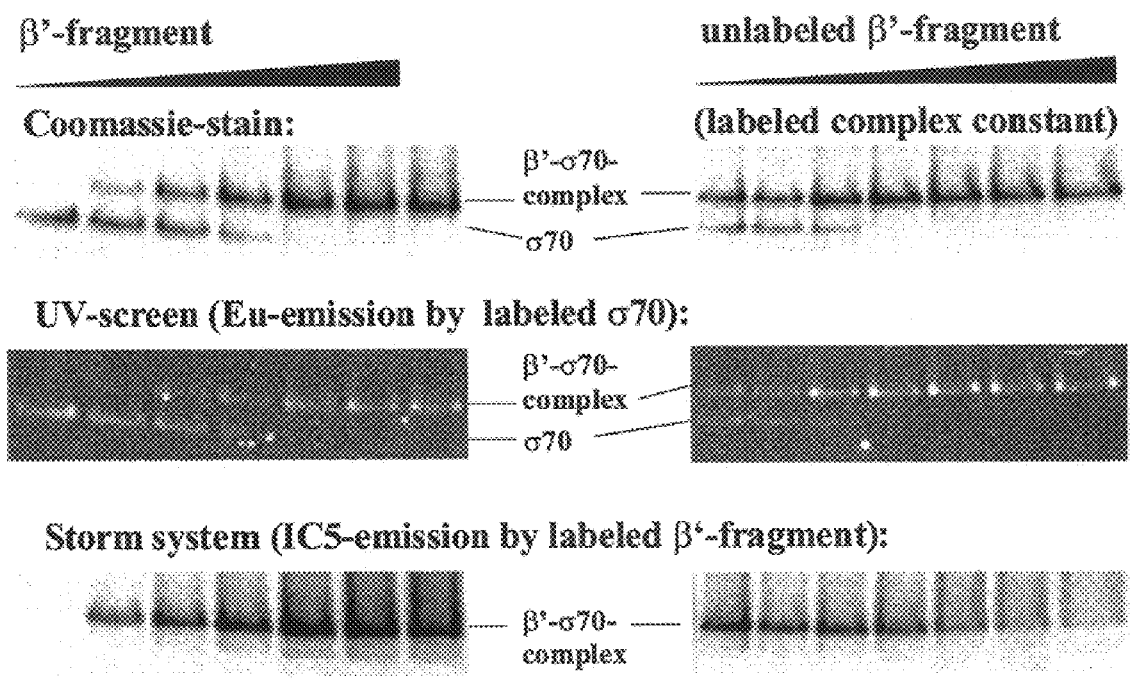
FIG. 16. The result of two EMS assays and three different acquisition methods. On the right side, the Coomassie-stained gel shows that increasing amounts of labeled β'-fragment can shift all the σ into the upper band representing the complex. The picture on the same gel below was acquired with a UV-box, which can only visualize the Eu-emission due to the excitation wavelength (312 nm) and an orange filter on the camera. It confirms that both bands contain Eu-labeled σ. At the bottom of each side is another picture of the same gel as above, this time taken with a Storm imager (Molecular Dynamics) that can only visualize the IC5-label. It confirms that only the upper band contains labeled β'-fragment. The free β'-fragment runs as a diffuse band barely migrating into the gel (data not shown).

The SDS-PAGE gel of the samples taken at different stages during the purification procedure can be seen in FIG. 15 (Coomassie-stain and IC5-sensitive scan). β' inclusion bodies were resuspended in 3 mL TNTwGu-buffer+5 mM imidazole, incubated at RT for 15 minutes. The precipitate was spun down in a microfuge at 18,000 g (14,000 rpm) for 5 minutes and the supernatant was loaded on a BioRad column (PolyPrep 10 mL, 0.8×4 cm) with approximately 0.8 mL Ni-NTA matrix (Qiagen) previously equilibrated with 5 mL TNTwGu-buffer+5 mM imidazole. To remove unbound protein, the column was washed with at least 3 mL TNTwGu-buffer+5 mM imidazole. To reduce any disulfide bonds, the column was washed with 5 mL freshly prepared TNTwGu-buffer+20 mM imidazole and 2 mM Tris(2-carboxyethyl)phosphine (TCEP). Excess TCEP and non-specifically bound protein were removed by washing with 3 mL TNTwGu-buffer+20 mM imidazole which was saturated with $N_2$. The bound protein was derivatized with IC5-maleimide by loading 2 mL freshly prepared TNTwGu-buffer+20 mM imidazole and 0.2 mM IC5. The flow-through was reloaded onto the column twice before excess dye was removed by washing with 3 mL TNTwGu-buffer+20 mM imidazole. Derivatized protein was eluted with TNTwGu-buffer+200 mM imidazole and stored denatured at −20° C.

Purification and Derivatization of $\sigma^{70}$

One aliquot of inclusion bodies (10 nmol protein, 0.7 mg) was solubilized by resuspending in 5 mL TGE-buffer+6 M GuHCl. To refold proteins, the denaturant was diluted 100-fold by dripping into chilled 500 mL TGE-buffer+0.01% Triton X-100 slowly stirring on ice. If precipitation occurs, the precipitate is spun down in a centrifuge at 25,000 g (15,000 rpm SS-34 rotor) for 15 minutes at 4° C. The refolded protein is then bound to an anion exchange resin by adding 1 g POROS HQ50 (PerSeptive Biosystems) dry resin as a suspension in 5 mL TGE-buffer+0.01% Triton X-100 directly into the mixture. After stirring for 30 minutes the suspension is poured over a 25 mL Econo Pack column (BioRad) and washed with 5 mL NTG-buffer. The column was plugged, and the resin was resuspended in 5 mL Storage-buffer, divided into 10 equal aliquots, transferred into empty rinsed Pharmacia spin-columns, and stored at −20° C. Prior to use, the buffer in the spin-columns was removed by centrifugation at 5000 g (4500 rpm) in a tabletop centrifuge. To label $\sigma^{70}$, 500 μL NTGE-buffer+0.01% Triton X-100 and 0.1 μmol DTPA-AMCA (a gift from the Heyduk lab) were used to resuspend the resin and incubated at RT for 30 minutes. The Eu-complex is formed by loading 5 μM $EuCl_3$ onto the resin with the derivatized protein. After centrifugation at 4500 rpm, the column was washed with 500 μL NTGE-buffer+0.01% Triton X-100. Then the labeled protein was eluted with 100 μL NTGE-buffer+500 mM NaCl. The flow through (labeled $\sigma^{70}$) was used directly in the assays.

The anion exchange resin POROS HQ50 (PerSeptive Biosystems) can be exchanged for DE52 (Whatman). Furthermore, labeling can also be done after purification and elution from the ion-exchange column simply by adding the protein solution to an aliquot of the dye (same buffers and conditions). Excess label and Eu-ions were then removed by using Pharmacia G50 spin-columns.

Electrophoretic Mobility Shift (EMS) Assay to Test Complex Formation of Labeled $\sigma^{70}$ and β'

The assays were performed in a buffer resulting of the use of 2×Native Sample-buffer and NTG-buffer (200 μL total volume, 5% glycerol, 50 mM Tris-HCl, pH 8.8, 50 mM NaCl, bromphenol blue 0.005% (w/v) and 2.5% DMSO is used when insoluble additives are applied). The standard protein concentrations were 2 μM $\sigma^{70}$ (labeled protein) and 2 μM β' (labeled protein) but can be lowered to 200 nM and 100 nM, respectively. Labeled $\sigma^{70}$ was added first to the assay, then the potential inhibitor and then denatured labeled β'. The solution was mixed well after the addition of each component. The mixture was incubated for 5 minutes at RT, and then 15 μL were loaded on a precast polyacrylamide gel (12-well, 12%, Tris/glycine, NOVEX). The electrophoresis was conducted with pre-chilled buffers, gels and apparatus in the cold room (4° C.) at constant voltage of 120 V (5–20 mA, variable) for 2.5 hours. The IC5-emission was scanned on a Storm system (Molecular Dynamics) in the red fluorescence mode. The Eu emission was measured using an UV box ($\lambda_{excit.}$=312 nm, Fotodyne) with 6 seconds acquisition time. Total protein was stained with Coomassie blue stain using the Gel Code staining solution (Pierce) according to the procedure of the manufacturer and scanned with a Hewlett Packard scanner using orange filter settings.

FRET Assay to Test for the Inhibition of Protein-protein Interaction of Labeled $\sigma^{70}$ and β'

The assay was performed in NTG-buffer (200 μL total volume) plus 2.5% DMSO (when insoluble additives were used) with 10 nM $\sigma^{70}$* (labeled protein) and 50 nM β'* (labeled protein). Labeled $\sigma^{70}$ was added first to the assay, then the potential inhibitor and denatured labeled β' was added last, mixing the solution well after the addition of each component. The mixture was incubated for 5 minutes at RT and measured in a 96-well plate (Costar 3650) with a multi-plate reader (Wallac, VictorV$^2$ 1420). For this time-resolved fluorescence measurement, the manufacturer's protocol (LANCE high count 615/665) was used (excitation with 1000 flashes, at 325 nm, measurement was delayed by 100 μs and acquired for 50 μs at 615 and 665 nm). In fluorimetric measurements it is common to use a second emission wavelength as an internal standard. This allows correction for instrument noise, but also to normalize the signal for the actual amount of donor in this particular case. This is possible since donor and acceptor emission wavelengths are well separated and can be acquired separately with the multi-plate reader. The IC5-emission is corrected for the very small amount of signal from the Eu-emission band (by cross talk measurement of a standard) and then divided by the intensity of the Eu signal. The normalization can be included into the overall measurement protocol and is described by the manufacturer of the multi-plate reader (Wallac). The nature of this method allows the differentiation of the loss of signal due to real inhibition from simple absorption caused by the inner filter effect from the substance. This assists in the identification of false positives in the actual high-throughput screen.

Results

Electrophoretic Mobility Shift (EMS) Assay to Test for the Complex Formation of Labeled $\sigma^{70}$ and β'

The EMS assays clearly showed that the labeled as well as the unlabeled proteins could form a complex that runs higher in the native gel than $\sigma^{70}$ alone. The different scanning techniques also confirmed the identity of the bands in the EMS assay (FIG. 11). Furthermore, the EMS assay showed that unlabeled β'-fragment can compete for the labeled $\sigma^{70}$. Thus, unlabeled β'-fragment itself represents a positive control for an agent able to interfere with the binding of labeled β'-fragment and $\sigma^{70}$ in the assay.

LRET Assay to Test for the Inhibition of Protein-protein Interaction of Labeled $\sigma^{70}$ and β'

Figure 17:
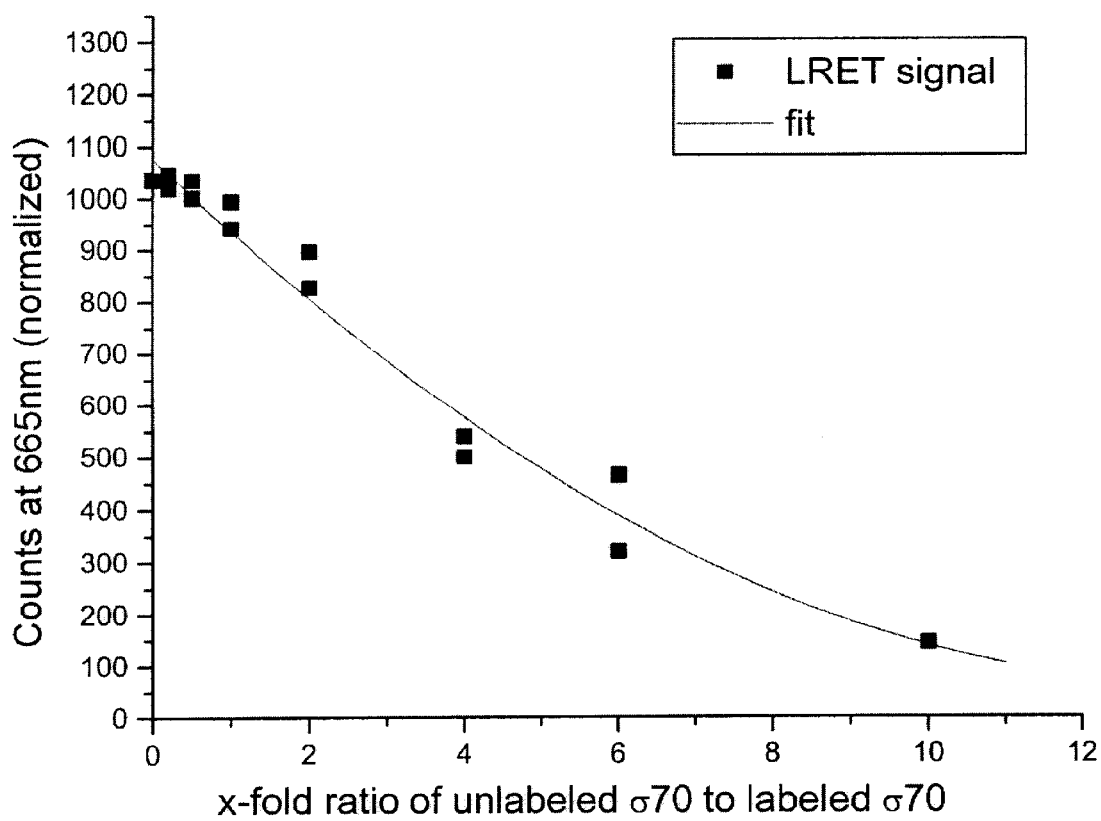
FIG. 17. Competition of labeled σ$^{70}$ binding to the β'-fragment by increasing amounts of unlabeled σ$^{70}$. The decreasing signal is due to the fact that labeled β'-fragment is competed away from the labeled σ$^{70}$ that it cannot be sensitized via LRET anymore.
Figure 18:
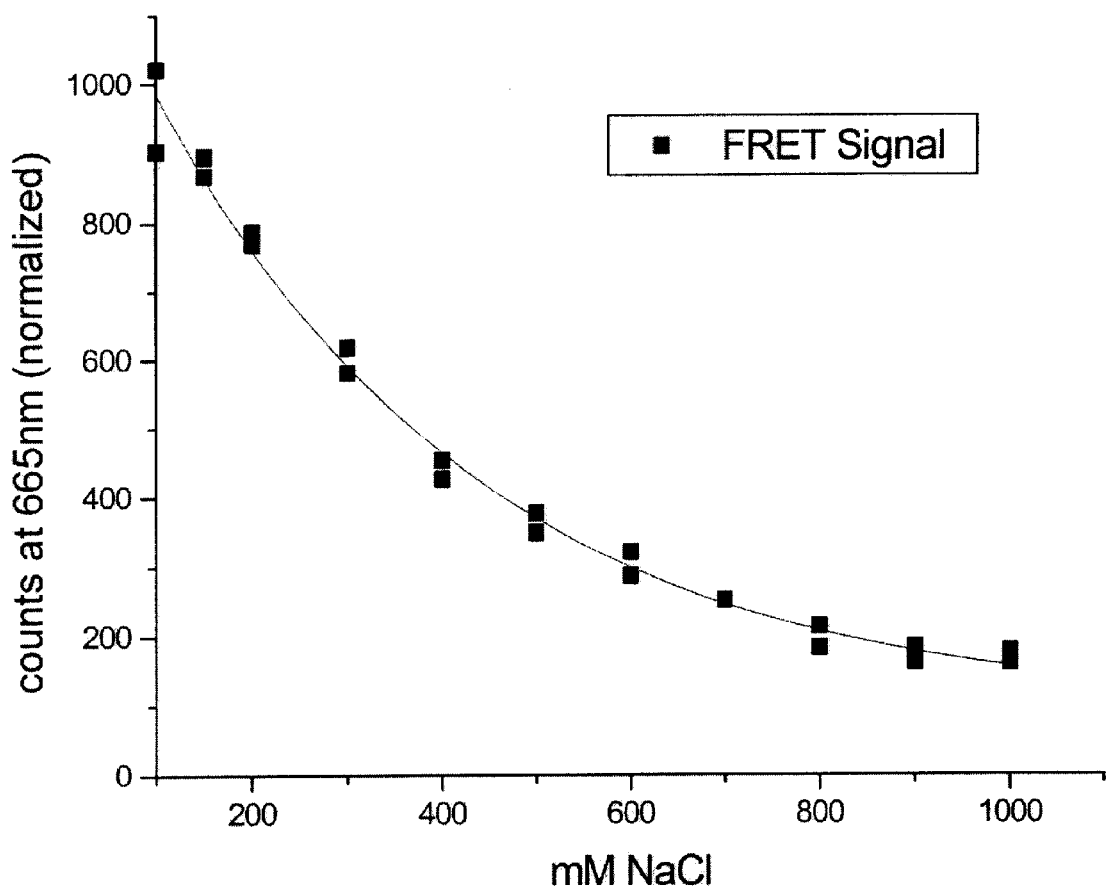
FIG. 18. Dependence of NaCl concentration on the LRET assay. With increasing amounts of salt, the LRET signal significantly decreases which should be due to the decreased amount of σ$^{70}$/β'-complex formed.
Figure 19:
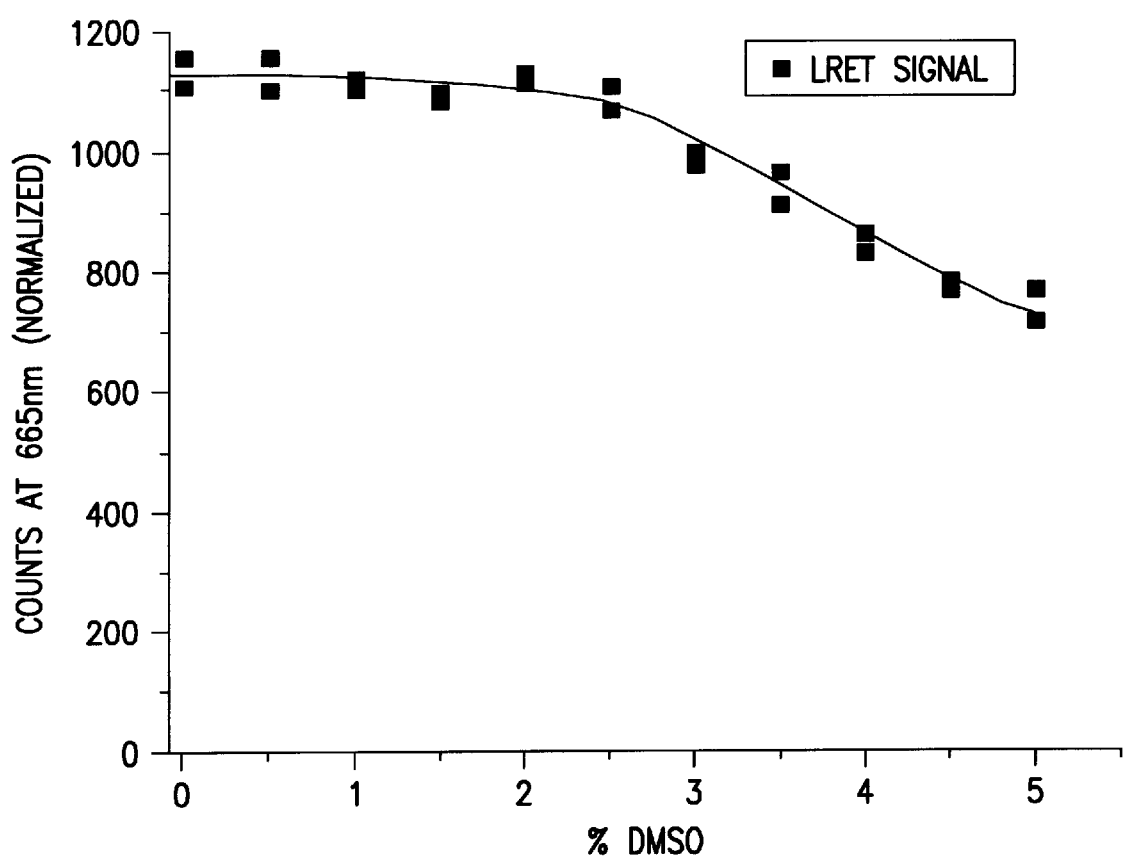
FIG. 19. Effect of DMSO concentration in the assay. Increasing amounts of DMSO (0–5%) mixed with the assay buffer previous to the addition of proteins, do not have a significant effect on the signal.

The LRET assay provides a fast and reproducible alternative to the EMS assay to monitor the formation of a protein-protein interaction between labeled $\sigma^{70}$ and β' as well as its inhibition. All results of the EMS assay were reproducible by the LRET assay, for example, competition of labeled $\sigma^{70}$ binding to the β'-fragment by increasing amounts of unlabeled $\sigma^{70}$ was observed (FIG. 17). In further experiments, the dependence of salt (NaCl) and solvents (DMSO) were characterized (FIGS. 18 and 19). As can be seen for the influence of NaCl on the assay, the salt concentration has a major effect on the signal, since it drops to 50% when the NaCl concentration was increased from 100 to 400 mM. It is known that this β'-fragment interaction with $\sigma^{70}$ is weaken by increased NaCl concentration. On the other hand, DMSO, a potential solvent for effectors to be tested, had no significant effect on the assay. As can be seen in FIG. 19, the signal in the LRET assay is not critically affected by the amount of DMSO present up to 5%. In the same experiment, ethanol showed a significant effect over the range of 1 to 5%. The signal-to-noise ratio for the assay was between 7 and 10. This is particularly desirable for a high-throughput screen since it cuts down on false positives by more accurate readings.

Discussion

There are several reasons to believe that the primary protein-protein interaction between bacterial core RNA polymerase (RNAP) and sigma factors represents a prime target for drug discovery. The key to the potential of this target is the absolute requirement of sigma binding to core RNAP for the initiation of transcription; any bacterial cell will die upon uptake of an inhibitor that effectively blocks this interaction. In addition to a very high bioactivity, a good specificity can also be expected since the binding region of both proteins is highly conserved among bacteria (FIG. 20) and is significantly different from any known eukaryotic analogue. This implies a very low probability for side effects to occur due to interference with human RNAP.

The site itself offers another advantage over many potential and specific targets. Since the binding site on the β'-subunit of RNAP interacts with all sigma factors of one bacterium, the development of resistance via point mutations against an inhibitor which binds to either one of them in the binding site is unlikely, since it would have to occur in both β' and all sigma factors at the same time. Due to the rising incidence of antibiotic resistance and the growing need for new antibiotics, this has recently become a major issue in drug discovery.

Luminescence resonance energy transfer (LRET) to measure sigma binding to core RNAP has been shown by Heyduk and coworkers to be an effective and very sensitive method. To prepare a LRET donor in the assay described above, a well-characterized $\sigma^{70}$(442C) mutant was used that had all natural cysteine residues mutated to serine residues, which was derivatized with a DTPA-AMCA-maleimide Eu-complex. A fragment (residues 100–309) of the β'-subunit of RNAP with a N-terminal HMK-site and $His_6$-tag fusion was derivatized with IC5-maleimide as LRET acceptor. The spectroscopic features of this pair of dyes and their behavior in LRET experiments are well characterized. Using EMS assays and spectrometric measurements using time-resolved fluorescence, it was shown that the labeled proteins can bind to each other in all combinations with and without the label. As controls, the unlabeled proteins were tested to determine if they could compete with their labeled counterpart. In both assays, EMS and LRET, unlabeled β'-fragment or $\sigma^{70}$ were able to compete with their labeled counterpart for binding in a complex. Therefore, the assay can be used to monitor $\sigma^{70}$ to β'-binding, and can be used to screen for inhibitors of this protein-protein interaction.

The assay represents a fast and sensitive probe for this particular complex-formation. Substrates and materials are either readily available or can be prepared in a simple and efficient procedures. All the labeled protein components showed excellent stability during storage, a great advantage when screening large libraries with 10,000 to 100,000 or more substances. Furthermore, the LRET assay has a very high sensitivity so that measurements can be performed at very low protein concentrations of 1 to 100 nM resulting in a very low cost per compound screened.

The LRET assay turned out to be not only very sensitive, but also very accurate. The very good signal-to-noise ratio of 7 to 10 and the internal standard method that helps to distinguish binding inhibition from fluorescence quenching by an inner filter effect of the test substance, contribute enormously to avoiding false positive readings. Also the very good compatibility of the assay with the use of DMSO, a potential solvent for test substances, adds to its applicability as a high-throughput screen. Since many natural products and most peptides or small molecules from combinatorial libraries have low solubility in water, it is necessary to use organic solvents. In this respect, DMSO represents the most versatile and potent solvent and since it is often used in libraries, its compatibility is desirable for any high-throughput assay.

Moreover, to improve the signal characteristics or just simply to use cheaper and more available compounds, probes other than DTPA-AMCA-EuIII and IC5 which exhibit FRET-based signals can be employed. A simple modification has been described above by exchanging IC5 (Dojindo, Japan) for Cy5 (Amersham) and has been shown to have no effect on the assay. Other europium chelates like DTPA-cs124-R and TTHA-AMCA-R (Selvin, 1999) have been described to be suitable. Companies like Packard ((Eu)K or XL665, TRACE reagents) as well as Wallac (DELFIA and LANCE reagents) are offering such dye pairs along with plate readers. For example, allophycocyanin APC (an analog of XL665) (Boisclair et al., 2000) can be used as an acceptor in combination with a Eu-donor. In all cases the dyes may be attached to specific antibodies that recognize the target proteins. Another rare earth metal, Terbium, can serve as an alternative LRET donor to Eu in similar complexes. Phalloidin-tetramethylrhodamine is also described as a LRET acceptor. Recently, different fusions of target proteins with variants of the green fluorescent protein have been used to monitor FRET in vivo (Harpur et al., 2001; Pollok and Heim, 1999) and could be employed to measure the inhibitory effect of potential compounds under in vivo conditions which also takes into account the delivery of the drug to the target organism. For example, pairs selected from the following could be employed: BFP, eGFP, CFP (cyan), YFP (yellow), and eYFP. Thus, proteins could be delivered to any bacterium via transfection or conjugation or employed in a yeast two hybrid system and used to screen potential inhibitory compounds in vivo.

In the case of screening natural product libraries with a high-throughput assay, a positive hit could represent a new class of antibiotic, since no substance is known with such a mode of action. On the other hand the screen will help to identify known antibiotics, for which the mode of activity has not yet been identified or that reveal more than one activity. Together with positive hits from combinatorial libraries, these substances can then serve as lead structures to design and tailor a new compound with desirable characteristics such as: high activity, specificity, stability and ability to enter the cell on the one hand and low side effects, costs, chance and likelihood of resistance development on the other hand. In addition this assay can serve as a powerful tool to investigate the relative binding of different sigma factors and sigma factor mutants to core.

References

Allison, L. A., *Biochimie,* 82, 537 (2000)

Allison, L. A., Moyle, M., Shales, M., and Ingles, C. J., *Cell,* 42, 599 (1985)

Arthur, T. M., Anthony, L. C., and Burgess, R. R., *J. Biol. Chem.,* 275, 23113 (2000)

Arthur, T. M. and Burgess, R. R., *J. Biol. Chem.,* 273, 31381 (1998)

Blanar, M. A. and Rutter, W. J., *Science.* 256, 1014 (1992)

Boisclair, M. D., McClure, C., Josiah, S., Glass, S., Bottomley, S., Kamerkar, S., and Hemmila, I., *J. Biomol. Screen,* 5, 319 (2000)

Bogan, A. A., and Thorn, K. S., *J. Mol. Biol.,* 280, 1 (1998)

Bornstein, P., and Bolian, G., *Methods Enzymol.,* 47, 132 (1970)

Brodolin, K., Mustaev, A., Severinov, K., and Nikiforov, V., *J. Biol. Chem.,* 275, 3661(2000)

Burgess, R. R., *Methods Enzymol.,* 273, 145 (1996)

Burgess, R. R., Arthur, T. M. and Pietz, B. C., in *Cold Spring Harbor Symposium,* Cold Spring Harbor Press, NY, 63, 277 (1998).

Burgess, R. R., Arthur, T. M., and Pietz, B. C., *Methods Enzymol.,* 328, 141 (2000)

Burgess, R. R., Travers, A. A., Dunn, J. J., and Bautz, E. K. F. *Nature,* 221, 43 (1969)

Callaci, S., Heyduk, E., and Heyduk, T., *J. Biol. Chem.,* 273, 32995 (1998)

Chao, H., Bautista, D. L., Litowski, J., Irvin, R. T., and Hodges, R. S., J. *Chromatogr. B Biomed. Sci. Appl.,* 715, 307 (1998)

Chen, Y., Ebright, Y. W. and Ebright, R. H., *Science,* 265, 90 (1994)

Cohen, C., and Parry, D. A. D., *Trends Biochem. Sci.,* 11, 245 (1986)

deArruda, M. and Burgess, R. R., *inNovations* (Novagen Newsletter), 4a, 7 (1996)

Destka, S., Liu, L., Wu, W and Izotora, L. *Prot. Exp. & Purif.,* 17, 203 (1999)

Dombrowski, A. J., Walter, W. A., and Gross, C. A., *Genes Dev.,* 7, 2446 (1993)

Eckert, D. M., Malashkevich, V. N., Hong, L. H., Carr, P. A., and Kim, P. S., *Cell,* 99,103 (1999)

El-Kettani, M. A., and Smith, J. C., *C. R. Acad. Sci. III,* 319, 161–9 (1996)

Ellgaard, L., Holtet, T., Moestrup, S., Etzerodt, M. and Thogersen, H., *J. Immunol. Methods,* 180, 53 (1995)

Farewell, A., Kvint, K., and Nystrom, T., *Mol. Microbiol.,* 29, 1039 (1998)

Fisher, R., and Blumenthal, T., *J. Biol. Chem.,* 255, 11056 (1980)

Fontana, A., Dalzoppo D., Grandi, C. and Zambonin, M., *Methods Enzymol.,* 91, 311 (1983)

Frere-Gallois, V., Krebs, D., Scala, D., Troalen, F., and Fermandjian, S., *Eur. J. Biochem.,*249, 142 (1997).

Fujita, M., *Genes Cells,* 5, 79(2000)

Gardella, T., Moyle, H., and Susskind, M. M., *J. Mol. Biol.,* 206, 579 (1989)

Gentz, R., Rauscher, F. J., III, Abate, C., and Curran, T., *Science,* 243, 1695 (1989)

Glass, R. E., Honda, A., and Ishihama, A., *Mol. Gen. Genet.,* 203, 492 (1986)

Gribskov, M., and Burgess, R. R. *Nucleic Acids Res.,* 14, 6745 (1986)

Gribskov, M., and Burgess, R. R., *Gene (Amst.),* 26, 109 (1983)

Gross, C. A., Chan, C. L., and Lonetto, M. A., *Phil. Trans. R. Soc. Lond. B Biol. Sci.,* 351, 475 (1996)

Gross, C. A., Lonetto, M., and Losick, R. in *Transcription Regulation* (McKnight, S., and Yamamoto, K., eds.) pp. 129–176, Cold Spring Harbor Press, Cold Spring Harbor, N.Y. (1992)

Grum, V. L., Li, D., MacDonald R. I., and Mondragon, A., *Cell,* 98, 523 (1999)

Harpur, A. G., Wouters, F. S., and Bastiaens, P. I., *Nat. Biotechnol.,* 19, 167 (2000)

Helmann, J. D., and Chamberlin, M. J., *Annu. Rev. Biochem.,* 57, 839 (1988)

Heyduk, E., and Heyduk, T., *J Biol. Chem.,* 274, 3315 (1999)

Hsieh, M., Hsu, H., Hwang, S., Wen, F., Yu, J., Wen, C., and Li, C., *Microbiol.,* 145, 3081(1999)

Igarashi, K., and Ishihama, A., *Cell,* 65, 1015 (1991)

Ishihama, A., *J. Bacteriol.,* 175, 2483 (1993)

Ishihama, A., *Adv. Biophys.,* 14, 1 (1981)

Jacobsen, G. R., Schaffer, M. H., Stark, G. R., and Vanaman, T. C., *J. Biol. Chem.,* 248, 6583 (1973)

Jishage, M., and Ishihama, A., *Proc. Natl. Acad. Sci. U.S.A.,* 95, 4953–4958 (1998)

Jokerst, R. S., Weeks, J. R., Zehring, W. A., and Greenleaf, A. L., *Mol. Gen. Genet.,* 215, 266(1989)

Joo, D. M., Nolte, A., Calendar, R., Zhou, Y. N., and Jin, D. J., *J. Bacteriol.,* 180, 1095 (1998)

Joo, D. M., Ng, N., and Calendar, R., *Proc. Natl. Acad. Sci. U.S.A.,* 94, 4907 (1997)

Ju, J., Mitchell, T., Peters III, H., and Haldenwang, W. G., *J. Bacteriol.,* 181, 4969 (1999).

Landschulz, W. H., Johnson, P. F., and McKnight, S. L., *Science,* 240, 1759 (1988)

Lesley, S. A., and Burgess, R. R., *Biochemistry,* 28, 7728 (1989)

Li, B.-L., Langer, J. A., Schwartz, B. and Pestka, S., *Proc. Natl. Acad. Sci. USA,* 86, 558 (1989)

Lieberman, P. M. and Berk, A. J., *Gene & Develop.,* 5, 2441 (1991)

Lonetto, M., Gribskov, M., and Gross, C. A., *J. Bacteriol.,* 174, 3843 (1992)

Lonetto, M. A., Rhodius, V., Lamberg, K., Kiley, P., Busby, S., and Gross, C., *J. Mol. Biol.,* 284, 1353 (1998)

Luo, J., Sharif, K. A., Jin, R., Fujita, N., Ishihama, A., and Krakow, J. S., *Genes Cells,* 1, 819 (1996)

Lupas, A., Van Dyke, M., and Stock, J., *Science,* 252, 1162 (1991)

Malhotra, A., Severinova, E., and Darst, S. A., *Cell,* 87, 127 (1996)

Marshak, D., Kadonaga, J., Burgess, R., Knuth, M., Lin, S.-H. and Brennan, W., "Strategies for Protein Purification and Characterization: A Laboratory Manual," pp. 205–274. Cold Spring Harbor Laboratory Press, Cold Spring Harbor, N.Y. (1996)

McMahan, S. A., and Burgess, R. R., *Biochemistry,* 38, 12424 (1999)

Muñoz, V. and Serrano, L., *Nature Struct. Biol.,* 1, 399 (1994)
Nagai, H., and Shimamoto, N., *Genes Cells,* 2, 725 (1995)
Nakamura, Y., *Mol Gen Genet,* 178, 487 (1980)
O'Shea, E. K., Rutkowski, R., and Kim, P. S., *Science,* 243, 538 (1989)
Owens, J. T., Miyake, R., Murakami, K., Chmura, A. J., Fujita, N., Ishihama, A., and Meares, C. F., *Proc. Natl. Acad. Sci. U.S.A.,* 95, 6021 (1998)
Pollok, B. A., and Heim, R., *Trends Cell Biol.,* 9, 57 (1999)
Rao, L., Jones, D. P., Nguyen, L. H., McMahan, S. A., and Burgess, R. R., *Anal. Biochem.,* 241, 173 (1996)
Ridley, S. P., and Oeshger, M. P., *J. Bacteriol.,* 152, 736 (1982)
Rost, B., Sander, C., and Schneider, R., *Comput. Appl. Bios.,* 10, 53 (1994)
Sayle, R. A., and Milner-White, E. J., *Trends Biochem. Sci.,* 20, 374 (1995)
Selvin, P. R., *Methods Enzymol.,* 246, 300 (1995)
Selvin, P. R., In "Applied Fluorescence in Chemistry, Biology and Medicine", W. Rettig, Strehmel, B., Schrader, S., 1st ed. (Springer Verlag), pp. 457–487 (1999)
Selvin, P. R., *Nat. Struct. Biol.,* 7, 730 (2000)
Severinov, K., Mooney, R., Darst, S. A., and Landick, R., *J. Biol. Chem.,* 272, 24137 (1997)
Severinov, K., Mustaev, A., Kukarin, A., Muzzin, O., Bass, I., Darst, S. A., and Goldfarb, A., *J. Biol. Chem.,* 271, 27969 (1996)
Severinov, K., Mustaev, A., Severinova, E., Bass, I., Kashlev, M., Landick, R., Nikiforov, V., Goldfarb, A., and Darst, S., *Proc. Natl. Acad. Sci. U.S.A.,* 92, 4591 (1995)
Severinov, K., Mustaev, A., Kashlev, M., Borukhov, S., Nikiforov, V., and Goldfarb, A., *J. Biol. Chem.,* 267, 12813 (1992)
Sharp, M. M., Chan, C. L., Lu, C. Z., Marr, M. T., Nechaev, S., Merritt, E. W., Severinov, K., Roberts, J. W., and Gross, C. A., *Genes & Devel.,* 13, 3015 (1999)
Shuler, M. F., Tatti, K. M., Wade, K. H., and Moran, C. P., Jr., *J. Bacteriol.,* 177, 3687 (1995)
Siegele, D. A., Hu, J. C., Walter, W. A., and Gross, C. A., *J. Mol. Biol.,* 206, 591 (1989)
Southern, E. M., *J. Mol. Biol.,* 98, 503 (1975)
Strickland, M. S., Thompson, N. E. and Burgess, R. R., *Biochemistry,* 27, 5755 (1988)
Stryer, L., *Annu. Rev. Biochem.,* 47, 819 (1975)
Studier, F. W., Rosenberg, A. H., Dunn, J. J., and Dubendorff, J. W., *Methods Enzymol.,* 185, 60 (1990)
Sweetser, D., Nonet, M., and Young, R. A., *Proc. Natl. Acad. Sci. U.S.A.,* 84, 1192 (1987)
Thompson, N. E., Hager, D. A., and Burgess, R. R., *Biochemistry,* 31, 7003(1992)
Towbin, H., Staehelin, T. and Gordon, J., *Proc. Natl. Acad. Sci. USA,* 76, 4350 (1979)
Tracy, R. L., and Stem, D. B., *Curr. Genet.,* 28, 205 (1995)
Traviglia, S. L., Datwyler, S. A., Yan, D., Ishihama, A., and Meares, C. F., *Biochemistry,* 38,15774 (1999)
Vinson, C. R., LaMarco, K. L., Johnson, P. F., Landschulz, W. H. and McKnight, S. L., *Genes & Develop.,* 2, 801 (1988)
Waldburger, C., and Susskind, M. M., *J. Mol. Biol.,* 235, 1489 (1994)
Waldburger, C., Gardella, T., Wong, R., and Susskind, M. M., *J. Mol. Biol.,* 215, 267 (1990)
Wang, D., Meier, T. I., Chan, C. L., Feng, G., Lee, D. N., and Landick, R. L., *Cell,* 81, 341(1995)
Weilbaecher, R., Hebron, C., Feng, G., and Landick, R., *Genes Dev.,* 8, 2913 (1994)
Wild, C. T., Shugars, D. C., Greenwell, T. K., McDanal, C. B., and Matthews, T. J., *Proc. Natl. Acad. Sci. USA,* 91, 9770 (1994)
Zhang, G., Campbell, E., Minakhin, L., Richter, C., Serenno, K., and Darst, S., *Cell,* 98, 811(1999)
Zhou, Y., and Gross, C. A., *J. Bacteriol.,* 174, 7128 (1992)
Zhou, Y. N., Walter, W. A., and Gross, C. A., *J. Bacteriol.,* 174, 5005 (1992)

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to identify an agent which inhibits the binding of σ to core RNA polymerase, a subunit thereof or a portion thereof, comprising:
   a) contacting the agent with core RNA polymerase, or an isolated β' subunit of RNA polymerase or a portion thereof, so as to form a complex;
   b) contacting the complex with σ or a portion thereof; and
   c) detecting or determining whether the agent inhibits or prevents the binding of σ to core RNA polymerase or to the isolated β' subunit of RNA polymerase or portion thereof, wherein the agent inhibits or prevents the interaction between σ and one or more of residues 266, 275, 295 or 302 of β'.

2. A method to identify an agent which inhibits the binding of σ to core RNA polymerase, a subunit thereof or a portion thereof, comprising:
   a) contacting the agent with σ or a portion thereof, so as to form a complex;
   b) contacting the complex with core RNA polymerase, or an isolated β' subunit of RNA polymerase or a portion thereof; and
   c) detecting or determining whether the agent inhibits or prevents the binding of σ to the β' subunit of core RNA polymerase or to the isolated β' subunit of RNA polymerase or portion thereof, wherein the agent inhibits or prevents the interaction between σ and one or more of residues 266, 275, 295 or 302 of β'.

3. A method to identify an agent which inhibits the binding of σ to core RNA polymerase, a subunit thereof or a portion thereof, comprising:
   a) contacting the agent with core RNA polymerase, or an isolated β' subunit of RNA polymerase or a portion thereof, so as to form a complex, wherein core RNA polymerase or the isolated β' subunit of RNA polymerase or portion thereof is labeled or binds to a detectable label; and wherein the agent inhibits or prevents the interaction between σ and one or more of residues 266, 275, 295, or 302 of β'.
   b) contacting the complex with σ or a portion thereof, wherein σ or a portion thereof is labeled or binds to a detectable label which is different than the label for core RNA polymerase, the isolated β' subunit of RNA polymerase or portion thereof; and
   c) detecting or determining the proximity of the two labels thereby detecting or determining whether the agent inhibits or prevents the binding of σ to core RNA polymerase or to the isolated β' subunit of RNA polymerase or portion thereof.

4. A method to identify an agent which inhibits the binding of σ to core RNA polymerase, a subunit thereof or a portion thereof, comprising:
   a) contacting the agent with σ or a portion thereof, so as to form a complex, wherein σ or a portion thereof is labeled or binds to a detectable label; and wherein the agent inhibits or prevents the interaction between σ and one or more of residues 266, 275, 295, or 302 of β'.
   b) contacting the complex with core RNA polymerase, or an isolated β' subunit of RNA polymerase or a portion thereof, wherein core RNA polymerase or the isolated β' subunit of RNA polymerase or portion thereof is labeled or binds to a detectable label which is different than the label for σ or portion thereof; and
   c) detecting or determining the proximity of the two labels thereby detecting or determining whether the agent inhibits or prevents the binding of σ to the β' subunit of core RNA polymerase or to the isolated β' subunit of RNA polymerase or portion thereof.

5. The method of claim 1,2,3 or 4 further comprising identifying the agent.

6. The method of claim 1 or 2 wherein the portion of the β' subunit comprises the interaction domain of the β' subunit.

7. The method of claim 6 wherein the portion of β' comprises residues 270 to 309 of β', residues 265 to 309 of β', residues 100 to 309 of β', or residues 260 to 309 of β'.

8. The method of claim 1 or 2 wherein the isolated subunit is a fusion protein.

9. The method of claim 1 or 2 wherein the σ is a homologous σ.

10. The method of claim 1 or 2 wherein the σ is a heterologous σ.

11. The method of claim 1 or 2 wherein the β' subunit of RNA polymerase or a portion thereof has at least one amino acid substitution relative to the native subunit.

12. The method of claim 1 or 2 wherein core RNA polymerase, or an isolated subunit of RNA polymerase or a portion thereof is labeled or binds to a detectable label.

13. The method of claim 12 wherein σ is labeled or binds to a detectable label which is different than the label for core RNA polymerase, an isolated subunit thereof or a portion thereof.

14. The method of claim 1,2,3 or 4 wherein the β' subunit is labeled with IC5 and σ is labeled with Eu.

15. The method of claim 1,2,3 or 4 wherein luminescence resonance energy transfer is employed to detect or determine whether the agent inhibits or prevents binding of σ to core RNA polymerase, or the isolated β' subunit of RNA polymerase or a portion thereof.

16. The method of claim 1,2,3 or 4 wherein fluorescence resonance energy transfer is employed to detect or determine whether the agent inhibits or prevents binding of σ to core RNA polymerase, or the isolated β' subunit of RNA polymerase or a portion thereof.

17. The method of claim 15 which employs europium or terbium.

18. The method of claim 15 which employs IC5, Cy5, allophycocyanin APC, or phalloidin-tetramethylrhodamine.

19. The method of claim 1 or 2 wherein σ or a portion thereof is labeled or binds to a detectable label.

20. The method of claim 19 wherein core RNA polymerase, or an isolated subunit of RNA polymerase or a portion thereof is labeled or binds to a detectable label which is different than the label for σ or a portion thereof.

21. A method for inhibiting or preventing the binding of σ to the β' subunit of core RNA polymerase, comprising contacting, in a sample, an agent identified by the method of claim 5 which inhibits the binding of σ to core RNA polymerase, the isolated β' subunit thereof or a portion thereof, wherein the agent inhibits or prevents the interaction between σ and one or more of residues 266,275,295 or 302 of β', with σ or a portion thereof and core RNA polymerase, the β' subunit of thereof, or a portion thereof, in an amount effective to inhibit or prevent binding of σ to the β' subunit of core RNA polymerase.

22. A method to identify an agent which inhibits or prevents the binding of σ to the β' subunit of core RNA polymerase, comprising:

a) contacting a prokaryotic cell with the agent; and b) detecting or determining whether the agent inhibits or prevents the binding of σ to the β' subunit of RNA polymerase in the cell.

23. The method of claim 22 wherein the cell comprises two different forms of the β' subunit.

24. The method of claim 23 wherein the agent is contacted with the cell under conditions in which one of the forms is not expressed.

25. The method of claim 24 wherein the form that is expressed has at least one amino acid substitution relative to the form which is not expressed.

26. The method of claim 21 wherein the sample includes a prokaryotic cell and wherein the agent inhibits the growth of the prokaryotic cell.

27. The method of claim 22 wherein the agent inhibits or prevents the binding of σ to residues 270 to 309 of β', residues 265 to 309 of β', residues 100 to 309 of β' or residues 260 to 309 of β' subunit.

28. A method to inhibit the growth of a prokaryotic cell, comprising: contacting the cell with an effective amount of the agent identified by the method of claim 5.

29. The method of claim 1 or 2 wherein the portion of the β' subunit is the interaction domain of the β' subunit.

30. The method of claim 29, wherein the portion of β' consists of residues 270 to 309 of β', residues 265 to 309 of β', residues 100 to 309 of β', or residues 260 to 309 of β'.

* * * * *

SEQUENCE LISTING

<160> NUMBER OF SEQ ID NOS: 26

<210> SEQ ID NO 1
<211> LENGTH: 14
<212> TYPE: PRT
<213> ORGANISM: Artificial Sequence
<220> FEATURE:
<223> OTHER INFORMATION: An N-terminal tag

<400> SEQUENCE: 1

Met Ala Arg Arg Ala Ser Val His His His His His His Met
 1               5                   10

<210> SEQ ID NO 2
<211> LENGTH: 13
<212> TYPE: PRT
<213> ORGANISM: Artificial Sequence
<220> FEATURE:
<223> OTHER INFORMATION: An N-terminal tag

```
<400> SEQUENCE: 2

Met Ala Arg Arg Ala Ser Val His His His His His
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: An N-terminal tag

<400> SEQUENCE: 3

Met Ala Arg Arg Ala Ser Val His His His His His
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: An N-terminal tag

<400> SEQUENCE: 4

Met Arg Arg Ala Ser Val His His His His His Ala
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: An N-terminal tag

<400> SEQUENCE: 5

Met His His His His His His Ala Arg Arg Ala Ser Val
 1               5                  10

<210> SEQ ID NO 6
<211> LENGTH: 50
<212> TYPE: PRT
<213> ORGANISM: Escherichia coli

<400> SEQUENCE: 6

Phe Ala Thr Ser Asp Leu Asn Asp Leu Tyr Arg Arg Val Ile Asn Arg
 1               5                  10                  15

Asn Asn Arg Leu Lys Arg Leu Leu Asp Leu Ala Ala Pro Asp Ile Ile
                20                  25                  30

Val Arg Asn Glu Lys Arg Met Leu Gln Glu Ala Val Asp Ala Leu Leu
            35                  40                  45

Asp Asn
    50

<210> SEQ ID NO 7
<211> LENGTH: 50
<212> TYPE: PRT
<213> ORGANISM: Thermus aquaticus

<400> SEQUENCE: 7

Phe Ala Thr Ser Asp Leu Asn Asp Leu Tyr Arg Arg Leu Ile Asn Arg
 1               5                  10                  15

Asn Asn Arg Leu Lys Lys Leu Leu Ala Gln Gly Ala Pro Glu Ile Ile
                20                  25                  30

Ile Arg Asn Glu Lys Arg Met Leu Gln Glu Ala Val Asp Ala Val Ile
```

```
                35                  40                  45
Asp Asn
    50

<210> SEQ ID NO 8
<211> LENGTH: 47
<212> TYPE: PRT
<213> ORGANISM: Escherichia coli

<400> SEQUENCE: 8

Ala Lys Ala Arg Arg Ala Lys Lys Glu Met Val Glu Ala Asn Leu Arg
 1               5                  10                  15

Leu Val Ile Ser Ile Ala Lys Lys Tyr Thr Asn Arg Gly Leu Gln Phe
            20                  25                  30

Leu Asp Leu Ile Gln Glu Gly Asn Ile Gly Leu Met Lys Ala Val
        35                  40                  45

<210> SEQ ID NO 9
<211> LENGTH: 47
<212> TYPE: PRT
<213> ORGANISM: C. crescentus

<400> SEQUENCE: 9

Arg Glu Ala Arg Gln Ala Lys Lys Glu Met Val Glu Ala Asn Leu Arg
 1               5                  10                  15

Leu Val Ile Ser Ile Ala Lys Lys Tyr Thr Asn Arg Gly Leu Gln Phe
            20                  25                  30

Leu Asp Leu Ile Gln Glu Gly Asn Ile Gly Leu Met Lys Ala Val
        35                  40                  45

<210> SEQ ID NO 10
<211> LENGTH: 47
<212> TYPE: PRT
<213> ORGANISM: P. putida

<400> SEQUENCE: 10

Ala Lys Ala Arg Arg Ala Lys Lys Glu Met Val Glu Ala Asn Leu Arg
 1               5                  10                  15

Leu Val Ile Ser Ile Ala Lys Lys Tyr Thr Asn Arg Gly Leu Gln Phe
            20                  25                  30

Leu Asp Leu Ile Gln Glu Gly Asn Ile Gly Leu Met Lys Ala Val
        35                  40                  45

<210> SEQ ID NO 11
<211> LENGTH: 47
<212> TYPE: PRT
<213> ORGANISM: H. influenza

<400> SEQUENCE: 11

Gln Lys Ala Arg Arg Ala Lys Lys Glu Met Val Glu Ala Asn Leu Arg
 1               5                  10                  15

Leu Val Ile Ser Ile Ala Lys Lys Tyr Thr Asn Arg Gly Leu Gln Phe
            20                  25                  30

Leu Asp Leu Ile Gln Glu Gly Asn Ile Gly Leu Met Lys Ala Val
        35                  40                  45

<210> SEQ ID NO 12
<211> LENGTH: 47
<212> TYPE: PRT
<213> ORGANISM: M. xanthus
```

```
<400> SEQUENCE: 12

Arg Arg Ala Glu Arg Ala Lys Ser Glu Leu Val Glu Ala Asn Leu Arg
 1               5                  10                  15

Leu Val Val Ser Ile Ala Lys Lys Tyr Thr Asn Arg Gly Leu Gln Phe
                20                  25                  30

Leu Asp Leu Ile Gln Glu Gly Asn Ile Gly Leu Met Lys Ala Val
            35                  40                  45

<210> SEQ ID NO 13
<211> LENGTH: 47
<212> TYPE: PRT
<213> ORGANISM: S. aureus

<400> SEQUENCE: 13

Gln Gly Asp Glu Val Ala Lys Ser Arg Leu Ala Glu Ala Asn Leu Arg
 1               5                  10                  15

Leu Val Val Ser Ile Ala Lys Arg Tyr Val Gly Arg Gly Met Leu Phe
                20                  25                  30

Leu Asp Leu Ile Gln Glu Gly Asn Met Gly Leu Ile Lys Ala Val
            35                  40                  45

<210> SEQ ID NO 14
<211> LENGTH: 47
<212> TYPE: PRT
<213> ORGANISM: B. subtilis

<400> SEQUENCE: 14

Glu Gly Asp Glu Glu Ser Lys Arg Arg Leu Ala Glu Ala Asn Leu Arg
 1               5                  10                  15

Leu Val Val Ser Ile Ala Lys Arg Tyr Val Gly Arg Gly Met Leu Phe
                20                  25                  30

Leu Asp Leu Ile His Glu Gly Asn Met Gly Leu Met Lys Ala Val
            35                  40                  45

<210> SEQ ID NO 15
<211> LENGTH: 47
<212> TYPE: PRT
<213> ORGANISM: T. maritima

<400> SEQUENCE: 15

Met Gly Asp Lys Lys Ala Lys Glu Lys Leu Ile Thr Ser Asn Leu Arg
 1               5                  10                  15

Leu Val Val Ser Ile Ala Lys Arg Tyr Met Gly Arg Gly Leu Ser Phe
                20                  25                  30

Gln Asp Leu Ile Gln Glu Gly Asn Ile Gly Leu Leu Lys Ala Val
            35                  40                  45

<210> SEQ ID NO 16
<211> LENGTH: 47
<212> TYPE: PRT
<213> ORGANISM: Escherichia coli

<400> SEQUENCE: 16

Ala Lys Ala Arg Arg Ala Lys Lys Glu Met Val Glu Ala Asn Leu Arg
 1               5                  10                  15

Leu Val Ile Ser Ile Ala Lys Lys Tyr Thr Asn Arg Gly Leu Gln Phe
                20                  25                  30

Leu Asp Leu Ile Gln Glu Gly Asn Ile Gly Leu Met Lys Ala Val
            35                  40                  45
```

<210> SEQ ID NO 17
<211> LENGTH: 44
<212> TYPE: PRT
<213> ORGANISM: Escherichia coli

<400> SEQUENCE: 17

Val Ala Ser Arg Arg Arg Met Ile Glu Ser Asn Leu Arg Leu Val Val
 1               5                  10                  15

Lys Ile Ala Arg Arg Tyr Gly Asn Arg Gly Leu Ala Leu Leu Asp Leu
                20                  25                  30

Ile Glu Glu Gly Asn Leu Gly Leu Ile Arg Ala Val
            35                  40

<210> SEQ ID NO 18
<211> LENGTH: 44
<212> TYPE: PRT
<213> ORGANISM: Escherichia coli

<400> SEQUENCE: 18

Leu Glu Ala Ala Lys Thr Leu Ile Leu Ser His Leu Arg Phe Val Val
 1               5                  10                  15

His Ile Ala Arg Asn Tyr Ala Gly Tyr Gly Leu Pro Gln Ala Asp Leu
                20                  25                  30

Ile Gln Glu Gly Asn Ile Gly Leu Met Lys Ala Val
            35                  40

<210> SEQ ID NO 19
<211> LENGTH: 37
<212> TYPE: PRT
<213> ORGANISM: Escherichia coli

<400> SEQUENCE: 19

Tyr Val Pro Leu Val Arg His Glu Ala Leu Arg Leu Gln Val Arg Leu
 1               5                  10                  15

Pro Ala Ser Val Glu Leu Asp Asp Leu Leu Gln Ala Gly Gly Ile Gly
                20                  25                  30

Leu Leu Asn Ala Val
        35

<210> SEQ ID NO 20
<211> LENGTH: 50
<212> TYPE: PRT
<213> ORGANISM: Escherichia coli

<400> SEQUENCE: 20

Phe Ala Thr Ser Asp Leu Asn Asp Leu Tyr Arg Arg Val Ile Asn Arg
 1               5                  10                  15

Asn Asn Arg Leu Lys Arg Leu Leu Asp Leu Ala Ala Pro Asp Ile Ile
                20                  25                  30

Val Arg Asn Glu Lys Arg Met Leu Gln Glu Ala Val Asp Ala Leu Leu
            35                  40                  45

Asp Asn
    50

<210> SEQ ID NO 21
<211> LENGTH: 50
<212> TYPE: PRT
<213> ORGANISM: T. aquaticus

<400> SEQUENCE: 21

Phe Ala Thr Ser Asp Leu Asn Asp Leu Tyr Arg Arg Leu Ile Asn Arg
1               5                   10                  15

Asn Asn Arg Leu Lys Lys Leu Leu Ala Gln Gly Ala Pro Glu Ile Ile
                20                  25                  30

Ile Arg Asn Glu Lys Arg Met Leu Gln Glu Ala Val Asp Ala Val Ile
            35                  40                  45

Asp Asn
    50

<210> SEQ ID NO 22
<211> LENGTH: 50
<212> TYPE: PRT
<213> ORGANISM: P. putida

<400> SEQUENCE: 22

Phe Ala Thr Ser Asp Leu Asn Asp Leu Tyr Arg Arg Val Ile Asn Arg
1               5                   10                  15

Asn Asn Arg Leu Lys Arg Gln Leu Asp Leu Ser Ala Pro Asp Ile Ile
                20                  25                  30

Val Arg Asn Glu Lys Pro Met Leu Gln Glu Ala Val Glu Pro Leu Leu
            35                  40                  45

Asp Asn
    50

<210> SEQ ID NO 23
<211> LENGTH: 50
<212> TYPE: PRT
<213> ORGANISM: H. influenza

<400> SEQUENCE: 23

Phe Ala Thr Ser Asp Leu Asn Asp Leu Tyr Arg Arg Val Ile Asn Arg
1               5                   10                  15

Asn Asn Arg Leu Lys Arg Leu Leu Asp Leu Ile Ala Pro Asp Ile Ile
                20                  25                  30

Val Arg Asn Glu Lys Arg Met Leu Gln Glu Ser Val Asp Ala Leu Leu
            35                  40                  45

Asp Asn
    50

<210> SEQ ID NO 24
<211> LENGTH: 50
<212> TYPE: PRT
<213> ORGANISM: S. aureus

<400> SEQUENCE: 24

Phe Ala Thr Ser Asp Leu Asn Asp Leu Tyr Arg Arg Val Ile Asn Arg
1               5                   10                  15

Asn Asn Arg Leu Lys Arg Leu Leu Asp Leu Gly Ala Pro Gly Ile Ile
                20                  25                  30

Val Gln Asn Glu Lys Arg Met Leu Gln Glu Ala Val Asp Ala Leu Ile
            35                  40                  45

Asp Asn
    50

<210> SEQ ID NO 25
<211> LENGTH: 50
<212> TYPE: PRT
<213> ORGANISM: B. subtilis

<400> SEQUENCE: 25

```
Phe Ala Thr Ser Asp Leu Asn Asp Leu Tyr Arg Arg Val Ile Asn Arg
1               5                   10                  15

Asn Asn Arg Leu Lys Arg Leu Leu Asp Leu Gly Ala Pro Ser Ile Ile
            20                  25                  30

Val Gln Asn Glu Lys Arg Met Leu Gln Glu Ala Val Asp Ala Leu Ile
            35                  40                  45

Asp Asn
    50

<210> SEQ ID NO 26
<211> LENGTH: 50
<212> TYPE: PRT
<213> ORGANISM: T. maritima

<400> SEQUENCE: 26

Phe Ala Thr Thr Asp Leu Asn Glu Leu Tyr Arg Arg Leu Ile Asn Arg
1               5                   10                  15

Asn Asn Arg Leu Lys Lys Leu Leu Glu Leu Gly Ala Pro Glu Ile Ile
            20                  25                  30

Leu Arg Asn Glu Lys Arg Met Leu Gln Glu Ala Val Asp Ala Leu Ile
            35                  40                  45

His Asn
    50
```